US012721897B2

(12) United States Patent
Zhang et al.

(10) Patent No.: US 12,721,897 B2
(45) **Date of Patent: *Sep. 1, 2026**

(54) PHARMACEUTICAL COMPOSITIONS OF POLYPEPTIDE CONJUGATES AND METHODS OF USES THEREOF

(71) Applicant: BEIJING QL BIOPHARMACEUTICAL CO., LTD., Beijing (CN)

(72) Inventors: Yuanyuan Zhang, Beijing (CN); Hongyu Shi, Beijing (CN); Xiaona Dong, Beijing (CN); Peng Zhai, Beijing (CN); Hongzhou Dong, Beijing (CN)

(73) Assignee: BEIJING QL BIOPHARMACEUTICAL CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/501,061

(22) Filed: Nov. 3, 2023

(65) Prior Publication Data

US 2024/0173416 A1 May 30, 2024

Related U.S. Application Data

(63) Continuation of application No. PCT/CN2023/084208, filed on Mar. 27, 2023.

(30) Foreign Application Priority Data

Mar. 25, 2022 (WO) ................ PCT/CN2022/083026
Mar. 23, 2023 (WO) ................ PCT/CN2023/083257

(51) Int. Cl.

*A61K 47/54* (2017.01)
*A61K 9/20* (2006.01)
*A61K 38/26* (2006.01)
*A61P 3/04* (2006.01)
*A61P 25/28* (2006.01)

(52) U.S. Cl.

CPC .......... *A61K 47/542* (2017.08); *A61K 9/2013* (2013.01); *A61K 9/2027* (2013.01); *A61K 9/2054* (2013.01); *A61K 38/26* (2013.01); *A61P 3/04* (2018.01); *A61P 25/28* (2018.01)

(58) Field of Classification Search

CPC ......... A61P 3/00; C07K 14/605; A61K 38/26; A61K 38/00

See application file for complete search history.

(56) References Cited

U.S. PATENT DOCUMENTS 5,208,020 A 5/1993 Chari et al.
6,191,102 B1 2/2001 DiMarchi et al.
6,268,343 B1 7/2001 Knudsen et al.
6,441,163 B1 8/2002 Chari et al.
6,458,924 B2 10/2002 Knudsen et al.
6,737,236 B1 5/2004 Pieken et al.
7,083,970 B2 8/2006 Schultz et al.
7,211,557 B2 5/2007 DiMarchi e
7,226,990 B2 6/2007 Knudsen et al.
7,235,627 B2 6/2007 Knudson et al.
7,576,059 B2 8/2009 Jonassen et al.
7,893,017 B2 2/2011 Lau et al.
8,097,698 B2 1/2012 Knudsen et al.
8,129,343 B2 3/2012 Lau et al.
8,445,433 B2 5/2013 Werbitzky et al.
8,536,122 B2 9/2013 Lau et al.
8,563,521 B2 10/2013 Skerra et al.
8,603,972 B2 12/2013 Lau et al.
8,648,041 B2 2/2014 Garibay et al.
8,673,860 B2 3/2014 Schellenberger et al.
8,895,694 B2 11/2014 Spetzler et al.
8,957,021 B2 2/2015 Schellenberger et al.
9,006,178 B2 4/2015 Kofoed et al.
9,067,977 B2 6/2015 Spetzler et al.
9,278,123 B2 * 3/2016 Sauerberg ............... A61P 15/08
9,498,534 B2 11/2016 Reedtz-Runge et al.
9,527,900 B2 12/2016 Linderoth et al.
9,550,819 B2 1/2017 Lindhout et al.
9,657,079 B2 5/2017 Spetzler et al.
9,708,383 B2 7/2017 Madsen et al.
9,732,137 B2 8/2017 Lau et al.
9,758,560 B2 9/2017 Lau et al.
10,000,542 B2 6/2018 Kofoed et al.
10,005,827 B2 6/2018 Spetzler et al.

(Continued)

FOREIGN PATENT DOCUMENTS

CN 100444898 C 12/2008
CN 101712722 A 5/2010

(Continued)

OTHER PUBLICATIONS

Wang et al., "Expanding the Genetic Code of *Escherichia coli*", Science 292: 498-500, Apr. 20, 2001.
Wang and Schultz et al., "An Expanded Eukaryotic Genetic Code", Science 301: 964-967, Aug. 15, 2003.
Altschul et al., "Basic Local Alignment Search Tool", J. Mol. Biol., 215:403-410 (1990).
Altschul et al., "Gapped BLAST and PSI-BLAST: a new generation of protein database search programs", Nucleic Acids Research, 1997, vol. 25, No. 17, 3389-3402.
Higgins et al., "Using Clustal for Multiple Sequence Alignments", Methods in Enzymology, 266:383-402 (1996).
Larkin et al., "Clustal W and Clustal X version 2.0", Bioinformatics (Oxford, England), 23(21):2947-8 (2007).

(Continued)

*Primary Examiner* — Li N Komatsu
*Assistant Examiner* — Jia-Hai Lee
(74) *Attorney, Agent, or Firm* — Junhe Law Office P.C.; James J. Zhu

(57) ABSTRACT

The present disclosure provides polypeptide conjugates comprising GLP-1 receptor agonist and a peptide linker, and pharmaceutical compositions comprising the same. Methods of using such for treating diseases are also provided.

9 Claims, 13 Drawing Sheets

Specification includes a Sequence Listing.

(56) References Cited

U.S. PATENT DOCUMENTS 10,010,614 B2 7/2018 Reedtz-Runge et al.
10,308,700 B2 6/2019 Lau et al.
10,370,426 B2 8/2019 Oh et al.
10,392,428 B2 8/2019 Kofoed
10,398,782 B2 9/2019 Gao et al.
10,400,020 B2 9/2019 Oh et al.
10,604,554 B2 3/2020 Kofoed et al.
10,689,429 B2 6/2020 Linderoth et al.
10,946,074 B2 3/2021 Kofoed et al.
11,130,794 B2 9/2021 Tornoee et al.
11,529,394 B2 * 12/2022 Zhang ........................ A61P 3/10
2003/0027996 A1 2/2003 Staby
2003/0199672 A1 10/2003 Knudsen et al.
2004/0265952 A1 12/2004 Deiters et al.
2007/0042956 A1 2/2007 Johansen et al.
2007/0093417 A1 4/2007 Hansen et al.
2007/0203058 A1 8/2007 Lau et al.
2007/0203068 A1 8/2007 Nielsen
2008/0081038 A1 4/2008 Cho et al.
2008/0214439 A1 9/2008 Grabstein et al.
2009/0005312 A1 1/2009 Hansen et al.
2009/0092582 A1 4/2009 Bogin et al.
2009/0156478 A1 6/2009 Lau et al.
2010/0239554 A1 9/2010 Schellenberger et al.
2010/0260706 A1 10/2010 Bogin et al.
2010/0317057 A1 12/2010 Lau et al.
2011/0213131 A1 9/2011 Christensen et al.
2011/0312881 A1 12/2011 Silverman et al.
2012/0000418 A1 1/2012 Huang
2013/0244931 A1 9/2013 Lau et al.
2015/0017188 A1 1/2015 Eigenbrot, Jr. et al.
2015/0152157 A1 6/2015 Kofoed et al.
2015/0210745 A1 7/2015 Kofoed et al.
2015/0266943 A1 9/2015 Chhabra et al.
2015/0273069 A1 10/2015 Bjerregaard et al.
2016/0143998 A1 5/2016 Reedtz-Runge et al.
2016/0158321 A1 6/2016 Cleland et al.
2016/0199454 A1 7/2016 Liu et al.
2017/0037088 A1 2/2017 Schellenberger et al.
2017/0058014 A1 3/2017 Wieczorek et al.
2017/0145069 A1 5/2017 Lau et al.
2017/0240614 A1 8/2017 Baldwin et al.
2017/0320927 A1 11/2017 Sauerberg et al.
2018/0051063 A1 2/2018 Cleland et al.
2018/0125988 A1 5/2018 Yang et al.
2018/0127512 A1 5/2018 Doronina et al.
2018/0291076 A1 10/2018 Kjeldsen et al.
2019/0083577 A1 3/2019 Schellenberger et al.
2019/0153115 A1 5/2019 Schellenberger et al.
2020/0087379 A1 3/2020 Schellenberger et al.
2020/0231645 A1 7/2020 Tornoee et al.
2020/0392195 A1 12/2020 Schellenberger et al.
2022/0009989 A1 1/2022 Muenzel et al.

FOREIGN PATENT DOCUMENTS

CN 103619175 A 3/2014
CN 111265654 A 6/2020
WO 1991011457 A1 8/1991
WO 1996029342 A1 9/1996
WO 1998008871 A1 3/1998
WO 1999043341 A1 9/1999
WO 1999043705 A1 9/1999
WO 1999043706 A1 9/1999
WO 1999043707 A1 9/1999
WO 02/46227 A2 6/2002
WO 2007103515 A2 9/2007
WO 2011123813 A2 10/2011
WO 2012080471 A1 6/2012
WO 2012/140117 A1 10/2012
WO 2016131893 A1 8/2016
WO 2018121702 A1 7/2018
WO 2020207477 A1 10/2020
WO PCTCN2020119335 * 11/2020
WO 2021139744 A1 7/2021
WO WO2022068920 A1 * 4/2022 ............. C07K 19/00

OTHER PUBLICATIONS

Lau et al., "The discovery of the once weekly glucagon like peptide 1 (GLP-1) analog semaglutide", J. Med. Chem. 2015, 58, 7370-7380.

Dennis et al., "Albumin Binding as a General Strategy for Improving the Pharmacokinetics of Proteins", J. Biol Chem. 277, 38 (2002) 35035-35043.

Batzer et al., "Enhanced evolutionary PCR using oligonucleotides with inosine at the 3'-terminus", Nucleic Acids Research (1991), vol. 19, No. 18, 5081.

Ohtsuka et al., "An Alternative Approach to Deoxyoligonucleotides as Hybridization Probes by Insertion of Deoxyinosine at Ambiguous Codon Positions", J. Biol. Chem. 260: 2605-2608 (1985).

Rossolini et al., "Use of deoxyinosine-containing primers vs degenerate primers for polymerase chain reaction based on ambiguous sequence information", Mol. Cell. Probes 8:91-98 (1994).

Carter et al., "High Level *Escherichia coli* Expression and Production of a Bivalent Humanized Anitbody Fragment", Bio/Technology 10:163-167 (1992).

Carlsson et al., "Protein Thiolation and Reversible Protein-Protein Conjugation N-Succinimidyl 3-(2-Pyridyldithio)Propionate, a New Heterobifunctional Reagent", Blochem. J. (1978) 173, 723-737.

Kim, Y.et al., "Novel AGLP-1 albumin fusion protein as a long-lasting agent for type 2 diabetes", BMB Reports, Dec. 31, 2013(Dec. 31, 2013) No. 12, vol. 46, 606-610.

Jiang, Y.N.et al., "Application of new fusion sequence in long-term GLP-1 drugs development", Chinese Doctoral Dissertations & Master's Theses Full-text Database (Master) Medicine and Health Sciences, Feb. 15, 2018(Feb. 15, 2018) No. 02.

McBrayer,D.N et al., "Recent Advances in GLP-1 Receptor Agonists for Use in Diabetes Mellitus", Drug Dev Res., Sep. 30, 2017(Sep. 30, 2017) No. 6, vol. 78, abstract, pp. 292-299.

Deiters et al., "Adding Amino Acids with Novel Reactivity to the Genetic Code of Saccharomyces Cerevisiae", J. Am. Chem. Soc. 2003, 125, 11782-11783.

Zhang et al., "A New Strategy for the Synthesis of Glycoproteins", Science 303:371-373, 2004.

Steinert, R.E., et al., "Oral administration of glucagon-like peptide 1 or peptide YY 3-36 affects food intake in healthy male subjects", Am. J. Clin. Nutr., vol. 92, Aug. 18, 2010 (Aug. 18, 2010), p. 810 abstract.

International Search Report of PCT/CN2023/084208, mailed on Jun. 21, 2023.

First Office Action for the counterpart Chinese application 2023800114419, mailed on Jan. 12, 2024.

Maggio E T: "Absorption enhancing excipients in systemic nasal drug delivery", Jun. 1, 2014 (Jun. 1, 2014), XP093245268, Retrieved from the Internet: URL:https://ojs.abo.fi/ojs/index.php/jefc/article/view/756.

Bruce J Aungst: "Absorption Enhancers: Applications and Advances", AAPS Journal, American Association of Pharmaceutical Scientists, US, vol. 14, No. 1, Nov. 22, 2011 (Nov. 22, 2011), pp. 10-18, XP035016737, ISSN: 1550-7416, DOI: 10.1208/S12248-011-9307-4.

EESR for the counterpart European application 23774039.4, mailed on Feb. 10, 2025.

* cited by examiner

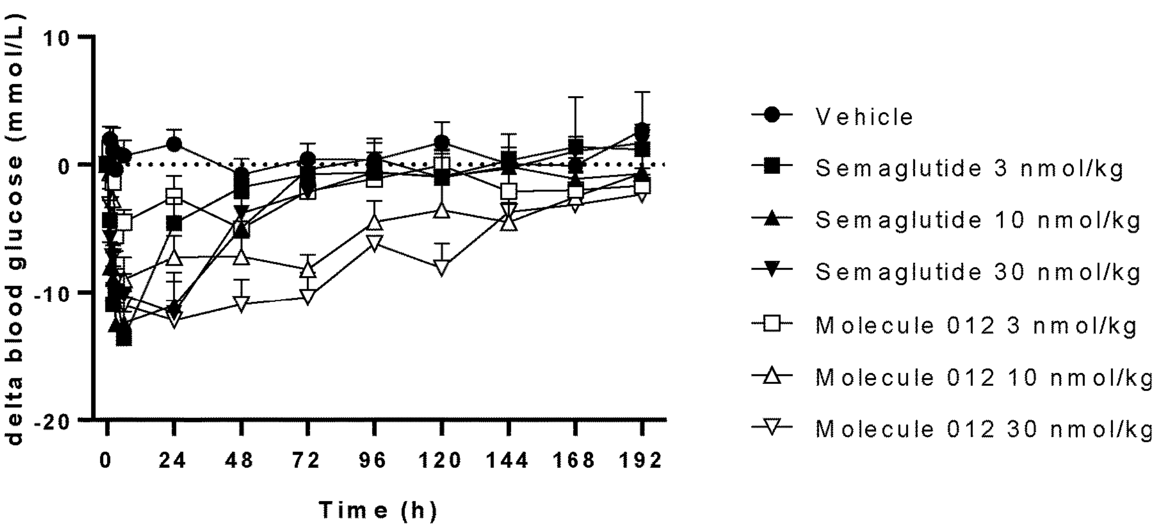
Figure 2C
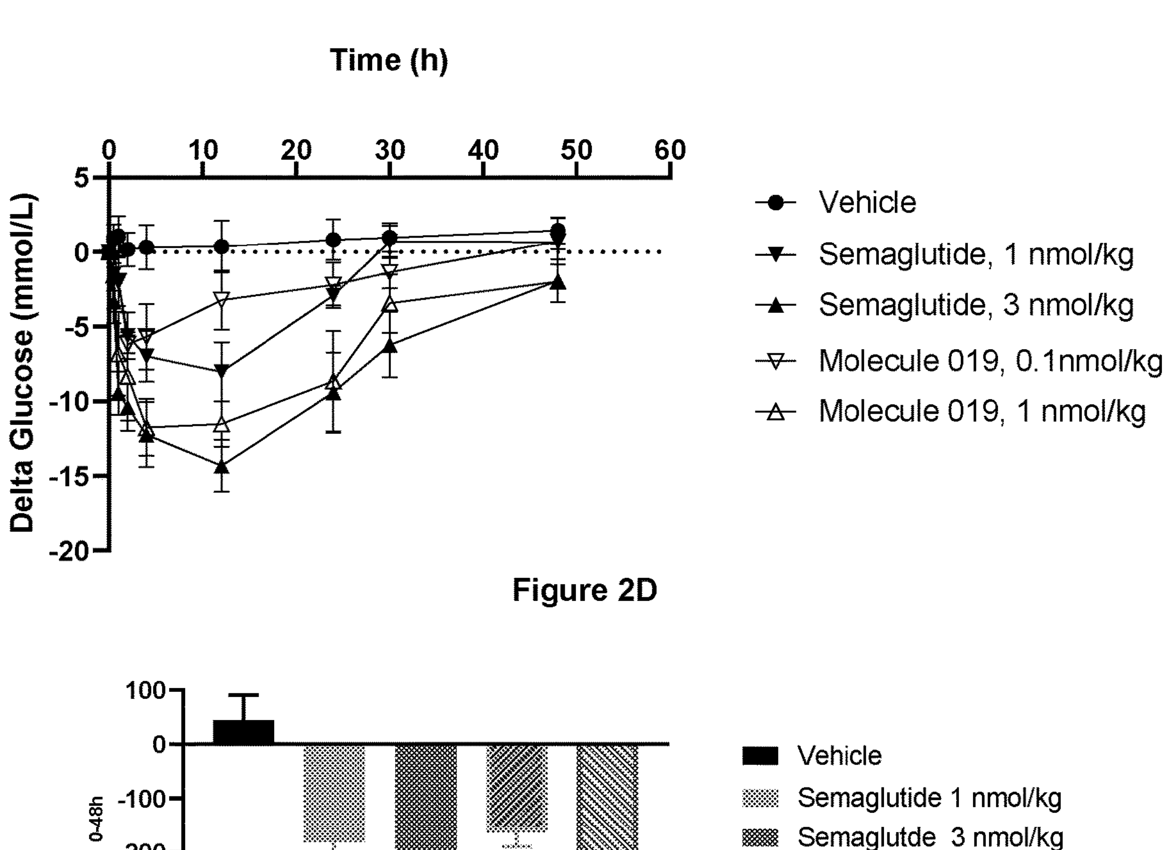
Figure 2D
Figure 2E

SNAC in solution (%)
120
100
80
60
40
20
0
0
5
10
15
20
25
30
35
Time (min)
Test B1
Test B2
Test B8
Test B9
Test B10
Test B12
Test B15
Test B16
Test B18
Test B19

GLP-1 Sequences in the Polypeptide Portion of the Polypeptide Conjugate

| SEQ ID NO | GLP-1 Sequence |
|---|---|
| 1 | HAEGTFTSDVSSYLEGQAAKEFIAWLVKGRG |
| 2 | $X_7X_8$EGTFTSDVSSYLE$X_{22}X_{23}$AA$X_{26}X_{27}$FI$X_{30}$WLV$X_{34}$G$X_{36}$G |
| 3 | HAib-EGTFTSDVSSYLEGQAAKEFIAWLVRGGG |
| 4 | HAib-EGTFTSDVSSYLEGQAACEFIAWLVRGGG |
| 5 | HAib-EGTFTSDVSSYLEGQAAREFIAWLVRGGG |
| 6 | HAib-EGTFTSDVSSYLEEQAAKEFIAWLVRGGG |
| 7 | HAib-EGTFTSDVSSYLEEQAACEFIAWLVRGGG |
| 8 | HAib-EGTFTSDVSSYLEEQAAREFIAWLVRGGG |
| 9 | HGEGTFTSDVSSYLEEQAAREFIAWLVRGGG |

Figure 6A

Repeating Sequences in the Peptide Linker (i.e. Linker Repeats) in the Polypeptide Portion of the Polypeptide Conjugate

| SEQ ID NO | Linker Repeat Sequence |
|---|---|
| 10 | GQEPGAQP |
| 11 | GAQPGAQP |
| 12 | GQEP |
| 13 | GAQP |
| 14 | GAQPGQEPGAQP |
| 15 | GAQPGQEP |
| 16 | GEQP |
| 17 | GPQE |
| 18 | GPEQ |
| 19 | GSEP |
| 20 | GESP |
| 21 | GPSE |
| 22 | GPES |
| 23 | GQAP |

Figure 6B

| | |
|---|---|
| **24** | GPAQ |
| **25** | GPQA |
| **26** | GSQP |
| **27** | GASP |
| **28** | GPAS |
| **29** | GPSA |
| **30** | GGGS |
| **31** | GSGS |
| **32** | GGGGS |
| **33** | GQEPGQAP |
| **34** | GQAPGQEP |
| **35** | SEPATSGSETPGTSESATPESGPGTSTEPSEG |
| **36** | SEPATS |
| **37** | GSETPG |
| **38** | TSESAT |
| **39** | PESGPG |
| **40** | TSTEPS |

Figure 6B(Continue)

Other Sequences in the Peptide Linker in the Polypeptide Portion of the Polypeptide Conjugate (underlined residues representing the CRM residue)

| **SEQ ID NO** | Sequence |
|---|---|
| **41** | GQKP |
| **42** | GQCP |

Figure 6C

Peptide Linker Sequences (i.e. Linker Sequences) in the Polypeptide Portion of the Polypeptide Conjugate

| **SEQ ID NO** | **Linker Sequence** |
|---|---|
| **43** | GAQPGAQPGAQPGAQPGAQPGAQPGAQPGAQPGAQPGQKP |
| **44** | GAQPGAQPGAQPGAQPGAQPGAQPGAQPGAQPGAQPGAQPGAQPGQKP |

Figure 6D

| | |
|---|---|
| **45** | GAQPGAQPGAQPGAQPGAQPGAQPGAQPGQKP |
| **46** | GAQPGAQPGAQPGAQPGAQPGQKP |
| **47** | GAQPGAQPGAQPGAQPGAQPGAQPGAQPGAQPGAQPGQCP |
| **48** | GAQPGAQPGAQPGAQPGAQPGAQPGAQPGAQPGAQPGAQPGAQPGQCP |
| **49** | GAQPGAQPGAQPGAQPGAQPGAQPGAQPGQCP |
| **50** | GAQPGAQPGAQPGAQPGAQPGQCP |
| **82** | GAQPGAQPGAQPGAQPGAQPGAQPGAQPGAQPGAQPGAQPGAQPGAQP GAQPGAQPGQKP |
| **83** | GAQPGAQPGAQPGAQPGAQPGQKP |
| **84** | GAQPGAQPGQKP |

Figure 6D(Continue)

Polypeptide Portion Sequences (i.e. Fusion Polypeptide Sequences) of the Polypeptide Conjugate

| SEQ ID NO | Fusion Polypeptide Sequence |
|---|---|
| **51** | HAib-EGTFTSDVSSYLEGQAAKEFIAWLVRGGGGAQPGAQPGAQPGAQPGAQP GAQPGAQPGAQPGAQPGQKP |
| **52** | HAib-EGTFTSDVSSYLEGQAAREFIAWLVRGGGGAQPGAQPGAQPGAQPGAQP GAQPGAQPGAQPGAQPGQKP |
| **53** | HAib-EGTFTSDVSSYLEGQAAKEFIAWLVRGGGGAQPGAQPGAQPGAQPGAQP GAQPGAQPGAQPGAQPGAQPGAQPGQKP |
| **54** | HAib-EGTFTSDVSSYLEGQAAKEFIAWLVRGGGGAQPGAQPGAQPGAQPGAQP GAQPGAQPGQKP |
| **55** | HAib-EGTFTSDVSSYLEGQAAREFIAWLVRGGGGAQPGAQPGAQPGAQPGAQP GAQPGAQPGQKP |
| **56** | HAib-EGTFTSDVSSYLEGQAAREFIAWLVRGGGGAQPGAQPGAQPGAQPGAQP GQKP |
| **57** | HAib-EGTFTSDVSSYLEEQAAKEFIAWLVRGGGGAQPGAQPGAQPGAQPGAQP GAQPGAQPGAQPGAQPGQKP |
| **58** | HAib-EGTFTSDVSSYLEEQAAKEFIAWLVRGGGGAQPGAQPGAQPGAQPGAQP GAQPGAQPGAQPGAQPGAQPGAQPGQKP |

Figure 6E

| | |
|---|---|
| **59** | HAib-EGTFTSDVSSYLEEQAAKEFIAWLVRGGGGAQPGAQPGAQPGAQPGAQPGAQPGAQPGQKP |
| **60** | HAib-EGTFTSDVSSYLEEQAAREFIAWLVRGGGGAQPGAQPGAQPGAQPGAQPGAQPGAQPGAQPGAQPGQKP |
| **61** | HAib-EGTFTSDVSSYLEEQAAREFIAWLVRGGGGAQPGAQPGAQPGAQPGAQPGAQPGAQPGQKP |
| **62** | HAib-EGTFTSDVSSYLEEQAAREFIAWLVRGGGGAQPGAQPGAQPGAQPGAQPGQKP |
| **63** | HAib-EGTFTSDVSSYLEGQAACEFIAWLVRGGGGAQPGAQPGAQPGAQPGAQPGAQPGAQPGAQPGAQPGAQPGAQPGQCP |
| **64** | HAib-EGTFTSDVSSYLEGQAACEFIAWLVRGGGGAQPGAQPGAQPGAQPGAQPGAQPGAQPGAQPGAQPGQCP |
| **65** | HAib-EGTFTSDVSSYLEGQAACEFIAWLVRGGGGAQPGAQPGAQPGAQPGAQPGAQPGAQPGQCP |
| **66** | HAib-EGTFTSDVSSYLEGQAAREFIAWLVRGGGGAQPGAQPGAQPGAQPGAQPGAQPGAQPGAQPGAQPGQCP |
| **67** | HAib-EGTFTSDVSSYLEGQAAREFIAWLVRGGGGAQPGAQPGAQPGAQPGAQPGAQPGAQPGQCP |
| **68** | HAib-EGTFTSDVSSYLEGQAAREFIAWLVRGGGGAQPGAQPGAQPGAQPGAQPGQCP |
| **69** | HGEGTFTSDVSSYLEEQAAREFIAWLVRGGGGAQPGAQPGAQPGAQPGAQPGAQPGAQPGAQPGAQPGQCP |
| **70** | HGEGTFTSDVSSYLEEQAAREFIAWLVRGGGGAQPGAQPGAQPGAQPGAQPGAQPGAQPGQCP |
| **71** | HGEGTFTSDVSSYLEEQAAREFIAWLVRGGGGAQPGAQPGAQPGAQPGAQPGQCP |
| **72** | HAib-EGTFTSDVSSYLEEQAACEFIAWLVRGGGGAQPGAQPGAQPGAQPGAQPGAQPGAQPGAQPGAQPGAQPGAQPGQCP |
| **73** | HAib-EGTFTSDVSSYLEEQAACEFIAWLVRGGGGAQPGAQPGAQPGAQPGAQPGAQPGAQPGAQPGAQPGQCP |

Figure 6E(Continue)

| | |
|---|---|
| **74** | HAib-EGTFTSDVSSYLEEQAACEFIAWLVRGGGGAQPGAQPGAQPGAQPGAQPGAQPGAQPGQCP |
| **75** | HAib-EGTFTSDVSSYLEGQAAKEFIAWLVRGGGGAQPGAQPGAQPGAQPGAQPGAQPGAQPGAQPGAQPGQCP |
| **76** | HAib-EGTFTSDVSSYLEGQAAKEFIAWLVRGGGGAQPGAQPGAQPGAQPGAQPGAQPGAQPGQCP |
| **77** | HAib-EGTFTSDVSSYLEGQAAKEFIAWLVRGGGGAQPGAQPGAQPGAQPGAQPGQCP |
| **78** | HAib-EGTFTSDVSSYLEEQAAKEFIAWLVRGGGGAQPGAQPGAQPGAQPGAQPGAQPGAQPGAQPGAQPGQCP |
| **79** | HAib-EGTFTSDVSSYLEEQAAKEFIAWLVRGGGGAQPGAQPGAQPGAQPGAQPGAQPGAQPGQCP |
| **80** | HAib-EGTFTSDVSSYLEEQAAKEFIAWLVRGGGGAQPGAQPGAQPGAQPGAQPGQCP |
| **85** | HAib-EGTFTSDVSSYLEGQAAKEFIAWLVRGGGGAQPGAQPGAQPGAQPGAQPGAQPGAQPGAQPGAQPGAQPGAQPGAQPGAQPGAQPGQKP |
| **86** | HAib-EGTFTSDVSSYLEGQAAKEFIAWLVRGGGGAQPGAQPGAQPGAQPGAQPGQKP |
| **87** | HAib-EGTFTSDVSSYLEGQAAKEFIAWLVRGGGGAQPGAQPGQKP |
| **88** | HAib-EGTFTSDVSSYLEGQAAREFIAWLVRGGGGAQPGAQPGQKP |

Figure 6E(Continue)

SEQUENCE LISTING

```
Sequence total quantity: 88
SEQ ID NO: 1             moltype = AA  length = 31
FEATURE                  Location/Qualifiers
REGION                   1..31
                         note = Synthetic
source                   1..31
                         mol_type = protein
                         organism = synthetic construct
SEQUENCE: 1
HAEGTFTSDV SSYLEGQAAK EFIAWLVKGR G                          31
```

-continued

```
SEQ ID NO: 2            moltype = AA  length = 31
FEATURE                 Location/Qualifiers
REGION                  1..31
                        note = Synthetic
SITE                    1
                        note = MISC_FEATURE - X is H, imidazole-4-acetate (IA), or
                         imidazolepropionic acid (IPA)
SITE                    2
                        note = MISC_FEATURE - X is A, G, S, V, Aib, T, I, or L
SITE                    16
                        note = MISC_FEATURE - X is G, or E
SITE                    17
                        note = MISC_FEATURE - X is Q, C or K
SITE                    20
                        note = MISC_FEATURE - X is K, R, or C
SITE                    21
                        note = MISC_FEATURE - X is E, K, or C
SITE                    24
                        note = MISC_FEATURE - X is A, C or K
SITE                    28
                        note = MISC_FEATURE - X is R, K, or C
SITE                    30
                        note = MISC_FEATURE - X is R or G
source                  1..31
                        mol_type = protein
                        organism = synthetic construct
SEQUENCE: 2
XXEGTFTSDV SSYLEXXAAX XFIXWLVXGX G                                 31

SEQ ID NO: 3            moltype = AA  length = 31
FEATURE                 Location/Qualifiers
REGION                  1..31
                        note = Synthetic
SITE                    2
                        note = MISC_FEATURE - X is Aib
source                  1..31
                        mol_type = protein
                        organism = synthetic construct
SEQUENCE: 3
HXEGTFTSDV SSYLEGQAAK EFIAWLVRGG G                                 31

SEQ ID NO: 4            moltype = AA  length = 31
FEATURE                 Location/Qualifiers
REGION                  1..31
                        note = Synthetic
SITE                    2
                        note = MISC_FEATURE - X is Aib
source                  1..31
                        mol_type = protein
                        organism = synthetic construct
SEQUENCE: 4
HXEGTFTSDV SSYLEGQAAC EFIAWLVRGG G                                 31

SEQ ID NO: 5            moltype = AA  length = 31
FEATURE                 Location/Qualifiers
REGION                  1..31
                        note = Synthetic
SITE                    2
                        note = MISC_FEATURE - X is Aib
source                  1..31
                        mol_type = protein
                        organism = synthetic construct
SEQUENCE: 5
HXEGTFTSDV SSYLEGQAAR EFIAWLVRGG G                                 31

SEQ ID NO: 6            moltype = AA  length = 31
FEATURE                 Location/Qualifiers
REGION                  1..31
                        note = Synthetic
SITE                    2
                        note = MISC_FEATURE - X is Aib
source                  1..31
                        mol_type = protein
                        organism = synthetic construct
SEQUENCE: 6
HXEGTFTSDV SSYLEEQAAK EFIAWLVRGG G                                 31

SEQ ID NO: 7            moltype = AA  length = 31
FEATURE                 Location/Qualifiers
```

-continued

```
REGION                  1..31
                        note = Synthetic
SITE                    2
                        note = MISC_FEATURE - X is Aib
source                  1..31
                        mol_type = protein
                        organism = synthetic construct
SEQUENCE: 7
HXEGTFTSDV SSYLEEQAAC EFIAWLVRGG G                                  31

SEQ ID NO: 8            moltype = AA  length = 31
FEATURE                 Location/Qualifiers
REGION                  1..31
                        note = Synthetic
SITE                    2
                        note = MISC_FEATURE - X is Aib
source                  1..31
                        mol_type = protein
                        organism = synthetic construct
SEQUENCE: 8
HXEGTFTSDV SSYLEEQAAR EFIAWLVRGG G                                  31

SEQ ID NO: 9            moltype = AA  length = 31
FEATURE                 Location/Qualifiers
REGION                  1..31
                        note = Synthetic
source                  1..31
                        mol_type = protein
                        organism = synthetic construct
SEQUENCE: 9
HGEGTFTSDV SSYLEEQAAR EFIAWLVRGG G                                  31

SEQ ID NO: 10           moltype = AA  length = 8
FEATURE                 Location/Qualifiers
REGION                  1..8
                        note = Synthetic
source                  1..8
                        mol_type = protein
                        organism = synthetic construct
SEQUENCE: 10
GQEPGAQP                                                            8

SEQ ID NO: 11           moltype = AA  length = 8
FEATURE                 Location/Qualifiers
REGION                  1..8
                        note = Synthetic
source                  1..8
                        mol_type = protein
                        organism = synthetic construct
SEQUENCE: 11
GAQPGAQP                                                            8

SEQ ID NO: 12           moltype = AA  length = 4
FEATURE                 Location/Qualifiers
REGION                  1..4
                        note = Synthetic
source                  1..4
                        mol_type = protein
                        organism = synthetic construct
SEQUENCE: 12
GQEP                                                                4

SEQ ID NO: 13           moltype = AA  length = 4
FEATURE                 Location/Qualifiers
REGION                  1..4
                        note = Synthetic
source                  1..4
                        mol_type = protein
                        organism = synthetic construct
SEQUENCE: 13
GAQP                                                                4

SEQ ID NO: 14           moltype = AA  length = 12
FEATURE                 Location/Qualifiers
REGION                  1..12
                        note = Synthetic
source                  1..12
                        mol_type = protein
                        organism = synthetic construct
```

-continued

```
SEQUENCE: 14
GAQPGQEPGA QP                                                    12

SEQ ID NO: 15           moltype = AA  length = 8
FEATURE                 Location/Qualifiers
REGION                  1..8
                        note = Synthetic
source                  1..8
                        mol_type = protein
                        organism = synthetic construct
SEQUENCE: 15
GAQPGQEP                                                         8

SEQ ID NO: 16           moltype = AA  length = 4
FEATURE                 Location/Qualifiers
REGION                  1..4
                        note = Synthetic
source                  1..4
                        mol_type = protein
                        organism = synthetic construct
SEQUENCE: 16
GEQP                                                             4

SEQ ID NO: 17           moltype = AA  length = 4
FEATURE                 Location/Qualifiers
REGION                  1..4
                        note = Synthetic
source                  1..4
                        mol_type = protein
                        organism = synthetic construct
SEQUENCE: 17
GPQE                                                             4

SEQ ID NO: 18           moltype = AA  length = 4
FEATURE                 Location/Qualifiers
REGION                  1..4
                        note = Synthetic
source                  1..4
                        mol_type = protein
                        organism = synthetic construct
SEQUENCE: 18
GPEQ                                                             4

SEQ ID NO: 19           moltype = AA  length = 4
FEATURE                 Location/Qualifiers
REGION                  1..4
                        note = Synthetic
source                  1..4
                        mol_type = protein
                        organism = synthetic construct
SEQUENCE: 19
GSEP                                                             4

SEQ ID NO: 20           moltype = AA  length = 4
FEATURE                 Location/Qualifiers
REGION                  1..4
                        note = Synthetic
source                  1..4
                        mol_type = protein
                        organism = synthetic construct
SEQUENCE: 20
GESP                                                             4

SEQ ID NO: 21           moltype = AA  length = 4
FEATURE                 Location/Qualifiers
REGION                  1..4
                        note = Synthetic
source                  1..4
                        mol_type = protein
                        organism = synthetic construct
SEQUENCE: 21
GPSE                                                             4

SEQ ID NO: 22           moltype = AA  length = 4
FEATURE                 Location/Qualifiers
REGION                  1..4
                        note = Synthetic
source                  1..4
                        mol_type = protein
```

-continued

```
                        organism = synthetic construct
SEQUENCE: 22
GPES                                                                        4

SEQ ID NO: 23           moltype = AA  length = 4
FEATURE                 Location/Qualifiers
REGION                  1..4
                        note = Synthetic
source                  1..4
                        mol_type = protein
                        organism = synthetic construct
SEQUENCE: 23
GQAP                                                                        4

SEQ ID NO: 24           moltype = AA  length = 4
FEATURE                 Location/Qualifiers
REGION                  1..4
                        note = Synthetic
source                  1..4
                        mol_type = protein
                        organism = synthetic construct
SEQUENCE: 24
GPAQ                                                                        4

SEQ ID NO: 25           moltype = AA  length = 4
FEATURE                 Location/Qualifiers
REGION                  1..4
                        note = Synthetic
source                  1..4
                        mol_type = protein
                        organism = synthetic construct
SEQUENCE: 25
GPQA                                                                        4

SEQ ID NO: 26           moltype = AA  length = 4
FEATURE                 Location/Qualifiers
REGION                  1..4
                        note = Synthetic
source                  1..4
                        mol_type = protein
                        organism = synthetic construct
SEQUENCE: 26
GSQP                                                                        4

SEQ ID NO: 27           moltype = AA  length = 4
FEATURE                 Location/Qualifiers
REGION                  1..4
                        note = Synthetic
source                  1..4
                        mol_type = protein
                        organism = synthetic construct
SEQUENCE: 27
GASP                                                                        4

SEQ ID NO: 28           moltype = AA  length = 4
FEATURE                 Location/Qualifiers
REGION                  1..4
                        note = Synthetic
source                  1..4
                        mol_type = protein
                        organism = synthetic construct
SEQUENCE: 28
GPAS                                                                        4

SEQ ID NO: 29           moltype = AA  length = 4
FEATURE                 Location/Qualifiers
REGION                  1..4
                        note = Synthetic
source                  1..4
                        mol_type = protein
                        organism = synthetic construct
SEQUENCE: 29
GPSA                                                                        4

SEQ ID NO: 30           moltype = AA  length = 4
FEATURE                 Location/Qualifiers
REGION                  1..4
                        note = Synthetic
source                  1..4
```

```
                      mol_type = protein
                      organism = synthetic construct
SEQUENCE: 30
GGGS                                                                4

SEQ ID NO: 31         moltype = AA  length = 4
FEATURE               Location/Qualifiers
REGION                1..4
                      note = Synthetic
source                1..4
                      mol_type = protein
                      organism = synthetic construct
SEQUENCE: 31
GSGS                                                                4

SEQ ID NO: 32         moltype = AA  length = 5
FEATURE               Location/Qualifiers
REGION                1..5
                      note = Synthetic
source                1..5
                      mol_type = protein
                      organism = synthetic construct
SEQUENCE: 32
GGGGS                                                               5

SEQ ID NO: 33         moltype = AA  length = 8
FEATURE               Location/Qualifiers
REGION                1..8
                      note = Synthetic
source                1..8
                      mol_type = protein
                      organism = synthetic construct
SEQUENCE: 33
GQEPGQAP                                                            8

SEQ ID NO: 34         moltype = AA  length = 8
FEATURE               Location/Qualifiers
REGION                1..8
                      note = Synthetic
source                1..8
                      mol_type = protein
                      organism = synthetic construct
SEQUENCE: 34
GQAPGQEP                                                            8

SEQ ID NO: 35         moltype = AA  length = 32
FEATURE               Location/Qualifiers
REGION                1..32
                      note = Synthetic
source                1..32
                      mol_type = protein
                      organism = synthetic construct
SEQUENCE: 35
SEPATSGSET PGTSESATPE SGPGTSTEPS EG                                 32

SEQ ID NO: 36         moltype = AA  length = 6
FEATURE               Location/Qualifiers
REGION                1..6
                      note = Synthetic
source                1..6
                      mol_type = protein
                      organism = synthetic construct
SEQUENCE: 36
SEPATS                                                              6

SEQ ID NO: 37         moltype = AA  length = 6
FEATURE               Location/Qualifiers
REGION                1..6
                      note = Synthetic
source                1..6
                      mol_type = protein
                      organism = synthetic construct
SEQUENCE: 37
GSETPG                                                              6

SEQ ID NO: 38         moltype = AA  length = 6
FEATURE               Location/Qualifiers
REGION                1..6
                      note = Synthetic
```

```
source                1..6
                      mol_type = protein
                      organism = synthetic construct
SEQUENCE: 38
TSESAT                                                                  6

SEQ ID NO: 39         moltype = AA  length = 6
FEATURE               Location/Qualifiers
REGION                1..6
                      note = Synthetic
source                1..6
                      mol_type = protein
                      organism = synthetic construct
SEQUENCE: 39
PESGPG                                                                  6

SEQ ID NO: 40         moltype = AA  length = 6
FEATURE               Location/Qualifiers
REGION                1..6
                      note = Synthetic
source                1..6
                      mol_type = protein
                      organism = synthetic construct
SEQUENCE: 40
TSTEPS                                                                  6

SEQ ID NO: 41         moltype = AA  length = 4
FEATURE               Location/Qualifiers
source                1..4
                      mol_type = protein
                      organism = synthetic construct
SEQUENCE: 41
GQKP                                                                    4

SEQ ID NO: 42         moltype = AA  length = 4
FEATURE               Location/Qualifiers
source                1..4
                      mol_type = protein
                      organism = synthetic construct
SEQUENCE: 42
GQCP                                                                    4

SEQ ID NO: 43         moltype = AA  length = 40
FEATURE               Location/Qualifiers
REGION                1..40
                      note = Synthetic
source                1..40
                      mol_type = protein
                      organism = synthetic construct
SEQUENCE: 43
GAQPGAQPGA QPGAQPGAQP GAQPGAQPGA QPGAQPGQKP                             40

SEQ ID NO: 44         moltype = AA  length = 48
FEATURE               Location/Qualifiers
REGION                1..48
                      note = Synthetic
source                1..48
                      mol_type = protein
                      organism = synthetic construct
SEQUENCE: 44
GAQPGAQPGA QPGAQPGAQP GAQPGAQPGA QPGAQPGAQP GAQPGQKP                    48

SEQ ID NO: 45         moltype = AA  length = 32
FEATURE               Location/Qualifiers
REGION                1..32
                      note = Synthetic
source                1..32
                      mol_type = protein
                      organism = synthetic construct
SEQUENCE: 45
GAQPGAQPGA QPGAQPGAQP GAQPGAQPGQ KP                                     32

SEQ ID NO: 46         moltype = AA  length = 24
FEATURE               Location/Qualifiers
source                1..24
                      mol_type = protein
                      organism = synthetic construct
SEQUENCE: 46
GAQPGAQPGA QPGAQPGAQP GQKP                                              24
```

```
SEQ ID NO: 47           moltype = AA  length = 40
FEATURE                 Location/Qualifiers
REGION                  1..40
                        note = Synthetic
source                  1..40
                        mol_type = protein
                        organism = synthetic construct
SEQUENCE: 47
GAQPGAQPGA QPGAQPGAQP GAQPGAQPGA QPGAQPGQCP                        40

SEQ ID NO: 48           moltype = AA  length = 48
FEATURE                 Location/Qualifiers
REGION                  1..48
                        note = Synthetic
source                  1..48
                        mol_type = protein
                        organism = synthetic construct
SEQUENCE: 48
GAQPGAQPGA QPGAQPGAQP GAQPGAQPGA QPGAQPGAQP GAQPGQCP               48

SEQ ID NO: 49           moltype = AA  length = 32
FEATURE                 Location/Qualifiers
REGION                  1..32
                        note = Synthetic
source                  1..32
                        mol_type = protein
                        organism = synthetic construct
SEQUENCE: 49
GAQPGAQPGA QPGAQPGAQP GAQPGAQPGQ CP                                32

SEQ ID NO: 50           moltype = AA  length = 24
FEATURE                 Location/Qualifiers
REGION                  1..24
                        note = Synthetic
source                  1..24
                        mol_type = protein
                        organism = synthetic construct
SEQUENCE: 50
GAQPGAQPGA QPGAQPGAQP GQCP                                         24

SEQ ID NO: 51           moltype = AA  length = 71
FEATURE                 Location/Qualifiers
REGION                  1..71
                        note = Synthetic
SITE                    2
                        note = MISC_FEATURE - X is Aib
source                  1..71
                        mol_type = protein
                        organism = synthetic construct
SEQUENCE: 51
HXEGTFTSDV SSYLEGQAAK EFIAWLVRGG GGAQPGAQPG AQPGAQPGAQ PGAQPGAQPG  60
AQPGAQPGQK P                                                       71

SEQ ID NO: 52           moltype = AA  length = 71
FEATURE                 Location/Qualifiers
REGION                  1..71
                        note = Synthetic
SITE                    2
                        note = MISC_FEATURE - X is Aib
source                  1..71
                        mol_type = protein
                        organism = synthetic construct
SEQUENCE: 52
HXEGTFTSDV SSYLEGQAAR EFIAWLVRGG GGAQPGAQPG AQPGAQPGAQ PGAQPGAQPG  60
AQPGAQPGQK P                                                       71

SEQ ID NO: 53           moltype = AA  length = 79
FEATURE                 Location/Qualifiers
REGION                  1..79
                        note = Synthetic
SITE                    2
                        note = MISC_FEATURE - X is Aib
source                  1..79
                        mol_type = protein
                        organism = synthetic construct
SEQUENCE: 53
HXEGTFTSDV SSYLEGQAAK EFIAWLVRGG GGAQPGAQPG AQPGAQPGAQ PGAQPGAQPG  60
AQPGAQPGAQ PGAQPGQKP                                               79
```

```
SEQ ID NO: 54           moltype = AA  length = 63
FEATURE                 Location/Qualifiers
REGION                  1..63
                        note = Synthetic
SITE                    2
                        note = MISC_FEATURE - X is Aib
source                  1..63
                        mol_type = protein
                        organism = synthetic construct
SEQUENCE: 54
HXEGTFTSDV SSYLEGQAAK EFIAWLVRGG GGAQPGAQPG AQPGAQPGAQ PGAQPGAQPG  60
QKP                                                                63

SEQ ID NO: 55           moltype = AA  length = 63
FEATURE                 Location/Qualifiers
REGION                  1..63
                        note = Synthetic
SITE                    2
                        note = MISC_FEATURE - X is Aib
source                  1..63
                        mol_type = protein
                        organism = synthetic construct
SEQUENCE: 55
HXEGTFTSDV SSYLEGQAAR EFIAWLVRGG GGAQPGAQPG AQPGAQPGAQ PGAQPGAQPG  60
QKP                                                                63

SEQ ID NO: 56           moltype = AA  length = 55
FEATURE                 Location/Qualifiers
REGION                  1..55
                        note = Synthetic
SITE                    2
                        note = MISC_FEATURE - X is Aib
source                  1..55
                        mol_type = protein
                        organism = synthetic construct
SEQUENCE: 56
HXEGTFTSDV SSYLEGQAAR EFIAWLVRGG GGAQPGAQPG AQPGAQPGAQ PGQKP       55

SEQ ID NO: 57           moltype = AA  length = 71
FEATURE                 Location/Qualifiers
REGION                  1..71
                        note = Synthetic
SITE                    2
                        note = MISC_FEATURE - X is Aib
source                  1..71
                        mol_type = protein
                        organism = synthetic construct
SEQUENCE: 57
HXEGTFTSDV SSYLEEQAAK EFIAWLVRGG GGAQPGAQPG AQPGAQPGAQ PGAQPGAQPG  60
AQPGAQPGQK P                                                       71

SEQ ID NO: 58           moltype = AA  length = 79
FEATURE                 Location/Qualifiers
REGION                  1..79
                        note = Synthetic
SITE                    2
                        note = MISC_FEATURE - X is Aib
source                  1..79
                        mol_type = protein
                        organism = synthetic construct
SEQUENCE: 58
HXEGTFTSDV SSYLEEQAAK EFIAWLVRGG GGAQPGAQPG AQPGAQPGAQ PGAQPGAQPG  60
AQPGAQPGAQ PGAQPGQKP                                               79

SEQ ID NO: 59           moltype = AA  length = 63
FEATURE                 Location/Qualifiers
REGION                  1..63
                        note = Synthetic
SITE                    2
                        note = MISC_FEATURE - X is Aib
source                  1..63
                        mol_type = protein
                        organism = synthetic construct
SEQUENCE: 59
HXEGTFTSDV SSYLEEQAAK EFIAWLVRGG GGAQPGAQPG AQPGAQPGAQ PGAQPGAQPG  60
QKP                                                                63

SEQ ID NO: 60           moltype = AA  length = 71
```

-continued

```
FEATURE                Location/Qualifiers
REGION                 1..71
                       note = Synthetic
SITE                   2
                       note = MISC_FEATURE - X is Aib
source                 1..71
                       mol_type = protein
                       organism = synthetic construct
SEQUENCE: 60
HXEGTFTSDV SSYLEEQAAR EFIAWLVRGG GGAQPGAQPG AQPGAQPGAQ PGAQPGAQPG  60
AQPGAQPGQK P                                                       71

SEQ ID NO: 61          moltype = AA  length = 63
FEATURE                Location/Qualifiers
REGION                 1..63
                       note = Synthetic
SITE                   2
                       note = MISC_FEATURE - X is Aib
source                 1..63
                       mol_type = protein
                       organism = synthetic construct
SEQUENCE: 61
HXEGTFTSDV SSYLEEQAAR EFIAWLVRGG GGAQPGAQPG AQPGAQPGAQ PGAQPGAQPG  60
QKP                                                                63

SEQ ID NO: 62          moltype = AA  length = 55
FEATURE                Location/Qualifiers
REGION                 1..55
                       note = Synthetic
SITE                   2
                       note = MISC_FEATURE - X is Aib
source                 1..55
                       mol_type = protein
                       organism = synthetic construct
SEQUENCE: 62
HXEGTFTSDV SSYLEEQAAR EFIAWLVRGG GGAQPGAQPG AQPGAQPGAQ PGQKP       55

SEQ ID NO: 63          moltype = AA  length = 79
FEATURE                Location/Qualifiers
REGION                 1..79
                       note = Synthetic
SITE                   2
                       note = MISC_FEATURE - X is Aib
source                 1..79
                       mol_type = protein
                       organism = synthetic construct
SEQUENCE: 63
HXEGTFTSDV SSYLEGQAAC EFIAWLVRGG GGAQPGAQPG AQPGAQPGAQ PGAQPGAQPG  60
AQPGAQPGAQ PGAQPGQCP                                               79

SEQ ID NO: 64          moltype = AA  length = 71
FEATURE                Location/Qualifiers
REGION                 1..71
                       note = Synthetic
SITE                   2
                       note = MISC_FEATURE - X is Aib
source                 1..71
                       mol_type = protein
                       organism = synthetic construct
SEQUENCE: 64
HXEGTFTSDV SSYLEGQAAC EFIAWLVRGG GGAQPGAQPG AQPGAQPGAQ PGAQPGAQPG  60
AQPGAQPGQC P                                                       71

SEQ ID NO: 65          moltype = AA  length = 63
FEATURE                Location/Qualifiers
REGION                 1..63
                       note = Synthetic
SITE                   2
                       note = MISC_FEATURE - X is Aib
source                 1..63
                       mol_type = protein
                       organism = synthetic construct
SEQUENCE: 65
HXEGTFTSDV SSYLEGQAAC EFIAWLVRGG GGAQPGAQPG AQPGAQPGAQ PGAQPGAQPG  60
QCP                                                                63

SEQ ID NO: 66          moltype = AA  length = 71
FEATURE                Location/Qualifiers
REGION                 1..71
```

-continued

```
                        note = Synthetic
SITE                    2
                        note = MISC_FEATURE - X is Aib
source                  1..71
                        mol_type = protein
                        organism = synthetic construct
SEQUENCE: 66
HXEGTFTSDV SSYLEGQAAR EFIAWLVRGG GGAQPGAQPG AQPGAQPGAQ PGAQPGAQPG  60
AQPGAQPGQC P                                                       71

SEQ ID NO: 67           moltype = AA  length = 63
FEATURE                 Location/Qualifiers
REGION                  1..63
                        note = Synthetic
SITE                    2
                        note = MISC_FEATURE - X is Aib
source                  1..63
                        mol_type = protein
                        organism = synthetic construct
SEQUENCE: 67
HXEGTFTSDV SSYLEGQAAR EFIAWLVRGG GGAQPGAQPG AQPGAQPGAQ PGAQPGAQPG  60
QCP                                                                63

SEQ ID NO: 68           moltype = AA  length = 55
FEATURE                 Location/Qualifiers
REGION                  1..55
                        note = Synthetic
SITE                    2
                        note = MISC_FEATURE - X is Aib
source                  1..55
                        mol_type = protein
                        organism = synthetic construct
SEQUENCE: 68
HXEGTFTSDV SSYLEGQAAR EFIAWLVRGG GGAQPGAQPG AQPGAQPGAQ PGQCP       55

SEQ ID NO: 69           moltype = AA  length = 71
FEATURE                 Location/Qualifiers
REGION                  1..71
                        note = Synthetic
source                  1..71
                        mol_type = protein
                        organism = synthetic construct
SEQUENCE: 69
HGEGTFTSDV SSYLEEQAAR EFIAWLVRGG GGAQPGAQPG AQPGAQPGAQ PGAQPGAQPG  60
AQPGAQPGQC P                                                       71

SEQ ID NO: 70           moltype = AA  length = 63
FEATURE                 Location/Qualifiers
REGION                  1..63
                        note = Synthetic
source                  1..63
                        mol_type = protein
                        organism = synthetic construct
SEQUENCE: 70
HGEGTFTSDV SSYLEEQAAR EFIAWLVRGG GGAQPGAQPG AQPGAQPGAQ PGAQPGAQPG  60
QCP                                                                63

SEQ ID NO: 71           moltype = AA  length = 55
FEATURE                 Location/Qualifiers
REGION                  1..55
                        note = Synthetic
source                  1..55
                        mol_type = protein
                        organism = synthetic construct
SEQUENCE: 71
HGEGTFTSDV SSYLEEQAAR EFIAWLVRGG GGAQPGAQPG AQPGAQPGAQ PGQCP       55

SEQ ID NO: 72           moltype = AA  length = 79
FEATURE                 Location/Qualifiers
REGION                  1..79
                        note = Synthetic
SITE                    2
                        note = MISC_FEATURE - X is Aib
source                  1..79
                        mol_type = protein
                        organism = synthetic construct
SEQUENCE: 72
HXEGTFTSDV SSYLEEQAAC EFIAWLVRGG GGAQPGAQPG AQPGAQPGAQ PGAQPGAQPG  60
AQPGAQPGAQ PGAQPGQCP                                               79
```

```
SEQ ID NO: 73          moltype = AA  length = 71
FEATURE                Location/Qualifiers
REGION                 1..71
                       note = Synthetic
SITE                   2
                       note = MISC_FEATURE - X is Aib
source                 1..71
                       mol_type = protein
                       organism = synthetic construct
SEQUENCE: 73
HXEGTFTSDV SSYLEEQAAC EFIAWLVRGG GGAQPGAQPG AQPGAQPGAQ PGAQPGAQPG  60
AQPGAQPGQC P                                                       71

SEQ ID NO: 74          moltype = AA  length = 63
FEATURE                Location/Qualifiers
REGION                 1..63
                       note = Synthetic
SITE                   2
                       note = MISC_FEATURE - X is Aib
source                 1..63
                       mol_type = protein
                       organism = synthetic construct
SEQUENCE: 74
HXEGTFTSDV SSYLEEQAAC EFIAWLVRGG GGAQPGAQPG AQPGAQPGAQ PGAQPGAQPG  60
QCP                                                                63

SEQ ID NO: 75          moltype = AA  length = 71
FEATURE                Location/Qualifiers
REGION                 1..71
                       note = Synthetic
SITE                   2
                       note = MISC_FEATURE - X is Aib
source                 1..71
                       mol_type = protein
                       organism = synthetic construct
SEQUENCE: 75
HXEGTFTSDV SSYLEGQAAK EFIAWLVRGG GGAQPGAQPG AQPGAQPGAQ PGAQPGAQPG  60
AQPGAQPGQC P                                                       71

SEQ ID NO: 76          moltype = AA  length = 63
FEATURE                Location/Qualifiers
REGION                 1..63
                       note = Synthetic
SITE                   2
                       note = MISC_FEATURE - X is Aib
source                 1..63
                       mol_type = protein
                       organism = synthetic construct
SEQUENCE: 76
HXEGTFTSDV SSYLEGQAAK EFIAWLVRGG GGAQPGAQPG AQPGAQPGAQ PGAQPGAQPG  60
QCP                                                                63

SEQ ID NO: 77          moltype = AA  length = 55
FEATURE                Location/Qualifiers
REGION                 1..55
                       note = Synthetic
SITE                   2
                       note = MISC_FEATURE - X is Aib
source                 1..55
                       mol_type = protein
                       organism = synthetic construct
SEQUENCE: 77
HXEGTFTSDV SSYLEGQAAK EFIAWLVRGG GGAQPGAQPG AQPGAQPGAQ PGQCP       55

SEQ ID NO: 78          moltype = AA  length = 71
FEATURE                Location/Qualifiers
REGION                 1..71
                       note = Synthetic
SITE                   2
                       note = MISC_FEATURE - X is Aib
source                 1..71
                       mol_type = protein
                       organism = synthetic construct
SEQUENCE: 78
HXEGTFTSDV SSYLEEQAAK EFIAWLVRGG GGAQPGAQPG AQPGAQPGAQ PGAQPGAQPG  60
AQPGAQPGQC P                                                       71

SEQ ID NO: 79          moltype = AA  length = 63
```

-continued

```
FEATURE               Location/Qualifiers
REGION                1..63
                      note = Synthetic
SITE                  2
                      note = MISC_FEATURE - X is Aib
source                1..63
                      mol_type = protein
                      organism = synthetic construct
SEQUENCE: 79
HXEGTFTSDV SSYLEEQAAK EFIAWLVRGG GGAQPGAQPG AQPGAQPGAQ PGAQPGAQPG  60
QCP                                                                63

SEQ ID NO: 80         moltype = AA  length = 55
FEATURE               Location/Qualifiers
REGION                1..55
                      note = Synthetic
SITE                  2
                      note = MISC_FEATURE - X is Aib
source                1..55
                      mol_type = protein
                      organism = synthetic construct
SEQUENCE: 80
HXEGTFTSDV SSYLEEQAAK EFIAWLVRGG GGAQPGAQPG AQPGAQPGAQ PGQCP       55

SEQ ID NO: 81         moltype = AA  length = 11
FEATURE               Location/Qualifiers
source                1..11
                      mol_type = protein
                      organism = Peptostreptococcus magnus
SEQUENCE: 81
DICLPRWGCL W                                                       11

SEQ ID NO: 82         moltype = AA  length = 60
FEATURE               Location/Qualifiers
REGION                1..60
                      note = Synthetic
source                1..60
                      mol_type = protein
                      organism = synthetic construct
SEQUENCE: 82
GAQPGAQPGA QPGAQPGAQP GAQPGAQPGA QPGAQPGAQP GAQPGAQPGA QPGAQPGQKP  60

SEQ ID NO: 83         moltype = AA  length = 24
FEATURE               Location/Qualifiers
REGION                1..24
                      note = Synthetic
source                1..24
                      mol_type = protein
                      organism = synthetic construct
SEQUENCE: 83
GAQPGAQPGA QPGAQPGAQP GQKP                                         24

SEQ ID NO: 84         moltype = AA  length = 12
FEATURE               Location/Qualifiers
REGION                1..12
                      note = Synthetic
source                1..12
                      mol_type = protein
                      organism = synthetic construct
SEQUENCE: 84
GAQPGAQPGQ KP                                                      12
```

-continued

```
SEQ ID NO: 85           moltype = AA  length = 91
FEATURE                 Location/Qualifiers
REGION                  1..91
                        note = Synthetic
SITE                    2
                        note = MISC_FEATURE - X is Aib
source                  1..91
                        mol_type = protein
                        organism = synthetic construct
SEQUENCE: 85
HXEGTFTSDV SSYLEGQAAK EFIAWLVRGG GGAQPGAQPG AQPGAQPGAQ PGAQPGAQPG  60
AQPGAQPGAQ PGAQPGAQPG AQPGAQPGQK P                                 91

SEQ ID NO: 86           moltype = AA  length = 55
FEATURE                 Location/Qualifiers
REGION                  1..55
                        note = Synthetic
SITE                    2
                        note = MISC_FEATURE - X is Aib
source                  1..55
                        mol_type = protein
                        organism = synthetic construct
SEQUENCE: 86
HXEGTFTSDV SSYLEGQAAK EFIAWLVRGG GGAQPGAQPG AQPGAQPGAQ PGQKP       55

SEQ ID NO: 87           moltype = AA  length = 43
FEATURE                 Location/Qualifiers
REGION                  1..43
                        note = Synthetic
SITE                    2
                        note = MISC_FEATURE - X is Aib
source                  1..43
                        mol_type = protein
                        organism = synthetic construct
SEQUENCE: 87
HXEGTFTSDV SSYLEGQAAK EFIAWLVRGG GGAQPGAQPG QKP                    43

SEQ ID NO: 88           moltype = AA  length = 43
FEATURE                 Location/Qualifiers
REGION                  1..43
                        note = Synthetic
SITE                    2
                        note = MISC_FEATURE - X is Aib
source                  1..43
                        mol_type = protein
                        organism = synthetic construct
SEQUENCE: 88
HXEGTFTSDV SSYLEGQAAR EFIAWLVRGG GGAQPGAQPG QKP                    43
```

PHARMACEUTICAL COMPOSITIONS OF POLYPEPTIDE CONJUGATES AND METHODS OF USES THEREOF

SEQUENCE LISTING

The instant application contains a Sequence Listing which has been submitted electronically in XML format and is hereby incorporated by reference in its entirety. Said XML copy, created on Oct. 26, 2023, is named 074585-8009US01.xml and is 127,746 bytes in size.

FIELD OF THE INVENTION

The present disclosure relates generally to the field of therapeutic peptides, and more specifically relates to polypeptide conjugates, i.e. glucagon-like peptide 1 (GLP-1) compounds, their pharmaceutical compositions, and methods of using such to prevent and/or treat metabolic disorders such as diabetes.

BACKGROUND

Metabolic disorders or metabolic disease are a group of conditions characterized by the inability of the body to properly transform foods into energy, and to utilize and/or store energy, with the most prominent metabolic disorder being diabetes. Metabolic disorders are commonly associated with insulin resistance, visceral adiposity, atherogenic dyslipidemia, etc., which pose major and escalating public health and clinical challenge worldwide.

Glucagon-like-peptide-1 (GLP-1) is a proglucagon-derived peptide that is secreted from intestinal L-cells in response to nutrient ingestion. GLP-1 primarily acts as an incretin, i.e. an endocrine hormone, to increase the insulin response following oral intake of food, by generally regulating the concentrations of glucagons, slowing down gastric emptying, stimulating the biosynthesis of (Pro-)insulin, increasing the sensitivity toward insulin, and stimulating the insulin-independent biosynthesis of glycogen, etc. Because GLP-1 can rapidly lower glucose levels in both normal and diabetic subjects, there has been considerable interest in developing GLP-1 based pharmaceutical agents (i.e. referred to as GLP-1 compounds hereinafter) for preventing and/or treating type 2 diabetes.

Currently, it is known that human GLP-1 in its native form (having 37 amino acid residues) is poorly active, and the two major naturally-occurring and biologically active truncated versions of the native GLP-1 include a 30- and 31-amino acid peptide fragment, i.e. GLP-1(7-36) or GLP-1 (7-37), which derive from the posttranslational processing of the proglucagon peptide, have extremely short in vivo half-lives due primarily to the N-terminal cleavage and inactivation by the dipeptidyl peptidase DPP-IV. Although tremendous efforts have been invested in developing newer and better GLP-1 compounds with more favorable administration regimens, existing GLP-1 compounds and their pharmaceutical compositions still have far from ideal half-lives, efficacy, and/or dosing frequency.

Therefore, there is a need for an improved design for GLP-1 compounds and for an improved pharmaceutical compositions thereof.

SUMMARY OF THE INVENTION

Provided herein include pharmaceutical compositions and methods of use thereof for treating/preventing metabolic disorders.

In a first aspect, the present disclosure provides a pharmaceutical composition, which comprises a polypeptide conjugate and an absorption enhancing excipient.

The polypeptide conjugate substantially comprises a polypeptide portion and a conjugate portion. The polypeptide portion comprises a single biologically active peptide and a peptide linker. The biologically active peptide is attached to N-terminus of the peptide linker and comprises a GLP-1 receptor agonist. The conjugate portion comprises a first clearance-reducing moiety (CRM) conjugated to a first CRM residue in the peptide linker.

In some embodiments, the first CRM residue is at least 5 amino acid residues (exclusive of the CRM residue), e.g. 5, 6, 7, 8, 9, 10, 11, 12, 13, 14, 15, 16, 17, 18, 19, 20, 21, 22, 23, 24, 25, 26, 27, 28, 29, 30, 33, 35, 38, 40, 43, 45, 48, 50, 53, 55, 58, 60, 63, 65, 68, 70, 73, 75, or 78 amino acid residues, away from the C-terminal amino acid residue of the biologically active peptide (e.g. the GLP-1 receptor agonist).

In some embodiments, the GLP-1 receptor agonist comprises GLP-1. As used herein, the term "GLP-1" refers to a molecule having the following characteristics: the molecule has substantially the biological activity of a wildtype human GLP-1 (SEQ ID NO: 1), and the molecule comprises a polypeptide fragment having an amino acid sequence of at least 50% identity to the wildtype human GLP-1.

In some embodiments, the GLP-1 comprises an amino acid sequence having at least 70% sequence identity to SEQ ID NO: 1 while retaining substantial biological activity of SEQ ID NO: 1.

In some embodiments, the GLP-1 comprises an amino acid sequence of $X_7X_8EGTFTSDVSSYLEX_{22}X_{23}AAX_{26}X_{27}FIX_{30}WLVX_{34}GX_{36}G$ (SEQ ID NO: 2), where the $X_7$ is H, imidazole-4-acetate (IA), or imidazolepropionic acid (IPA); the $X_8$ is A, G, S, V, Aib, T, I, or L; the $X_{22}$ is G, or E; the $X_{23}$ is Q, C or K; the $X_{26}$ is K, R, or C; the $X_{27}$ is E, K, or C; the $X_{30}$ is A, C or K; the $X_{34}$ is R, K, or C; and the $X_{36}$ is R or G.

In some embodiments of the GLP-1, the $X_7$ is H; and $X_8$ is G or Aib.

In some embodiments, the GLP-1 comprises or consists of one or more mutations at a position selected from the group consisting of: A8, G22, K26, K34, and R36, or any combination thereof, relative to SEQ ID NO: 1.

In some embodiments, the GLP-1 comprises or consists of one or more substitutions selected from the group consisting of: A8Aib, G22E, K26R, K34R and R36G, or any combination thereof.

In some embodiments, the GLP-1 comprises an amino acid sequence selected from the group consisting of: SEQ ID NOS: 3-9.

In any embodiment of the polypeptide conjugate as mentioned above, the peptide linker can have a length of at least 10 amino acid residues, at least 12, 24, 32, 40, 48, 50, 60, 70, or 80 amino acid residues.

In some embodiments, the peptide linker consists of amino acid residues selected from the group consisting of G, Q, A, E, P, S, and T, except for the first CRM residue.

In some embodiments, the peptide linker comprises a first sequence and a second sequence. The first sequence consists of one or more repeats of a repeating sequence, and is connected to N-terminus of the second sequence. The first CRM residue is in the second sequence, and is lysine residue or cysteine residue.

In some embodiments, the repeating sequence in the first sequence of the peptide linker has an amino acid sequence selected from a group consisting of SEQ ID NO: 10 (GQEP- GAQP), SEQ ID NO: 11 (GAQPGAQP), SEQ ID NO: 12(GQEP), SEQ ID NO: 13 (GAQP), SEQ ID NO: 14 (GAQPGQEPGAQP), SEQ ID NO: 15 (GAQPGQEP), SEQ ID NO: 16 (GEQP), SEQ ID NO: 17 (GPQE), SEQ ID NO: 18 (GPEQ), SEQ ID NO: 19 (GSEP), SEQ ID NO: 20 (GESP), SEQ ID NO: 21 (GPSE), SEQ ID NO: 22 (GPES), SEQ ID NO: 23 (GQAP), SEQ ID NO: 24 (GPAQ), SEQ ID NO: 25 (GPQA), SEQ ID NO: 26 (GSQP), SEQ ID NO: 27 (GASP), SEQ ID NO: 28 (GPAS), SEQ ID NO: 29 (GPSA), SEQ ID NO: 30 (GGGS), SEQ ID NO: 31 (GSGS), SEQ ID NO: 32 (GGGGS), SEQ ID NO: 33 (GQEPGQAP), SEQ ID NO: 34 (GQAPGQEP), SEQ ID NO: 35 (SEPATSG-SETPGTSESATPESGPGTSTEPSEG), SEQ ID NO: 36 (SEPATS), SEQ ID NO: 37 (GSETPG), SEQ ID NO: 38 (TSESAT), SEQ ID NO: 39 (PESGPG), SEQ ID NO: 40 (TSTEPS) and GS.

In some embodiments, the repeating sequence in the first sequence of the peptide linker has a sequence of SEQ ID NO: 13 (GAQP). Herein optionally, the number of the one or more repeats of the repeating sequence is an integer between 1 and 30. In certain embodiments, the number of the one or more repeats of the repeating sequence is selected from a group consisting of 5, 7, 9 and 11.

In certain embodiments, the second sequence of the peptide linker has a sequence of SEQ ID NO: 41 (GQKP) or SEQ ID NO: 42 (GQCP).

In certain embodiments, the polypeptide linker comprises an amino acid sequence selected from the group consisting of: SEQ ID NOS: 43-50, and 82-84.

In any embodiment of the polypeptide conjugate as mentioned above, the first CRM may comprise a plasma protein-binding moiety, a polymer, Fc, HSA (albumin), Xten sequence, or PAS sequence.

In some embodiments, the first CRM comprises an albumin-binding moiety.

In some embodiments, the albumin-binding moiety comprising a structure of: *-A-B-C-D-E, wherein A, B, C, D and E are interconnected via amide bonds, and the * end of A is connected to a reactive group of the conjugatable residue on the polypeptide complex.

Herein, A is selected from a bond,

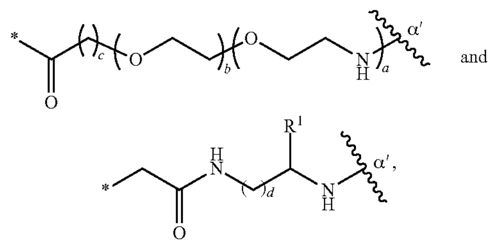

where a, b, c and d are independently an integer from 0 to 4, $R^1$ is hydrogen or —COOH.

Herein, B is selected from a bond,

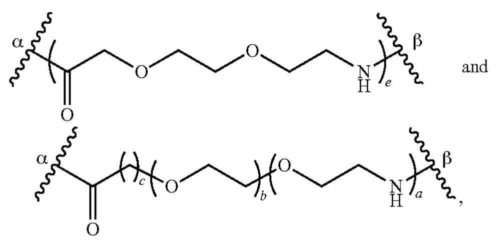

where e is an integer from 1 to 4, wherein position α is linked to position α'.

Herein, C is a bond or

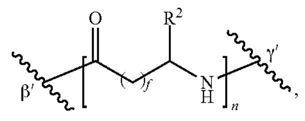

where $R^2$ is $—CH_2SO_3H$ or —COOH, f is an integer from 1 to 4, n is an integer from 1 to 25, wherein when B is not bond, then position β' is linked to position β, or when B is bond, then position β' is linked to position α~.

Herein, D is selected from a bond,

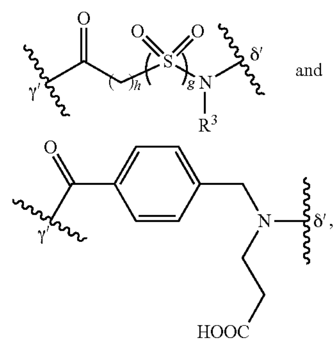

where g and h are independently 0 or 1, and $R^3$ is H or $—CH_2COOH$. Herein, when B is not a bond and C is a bond, then position γ' is linked to position β; when C is not a bond, then position γ' is linked to position γ; and when B is a bond and C is a bond, then position γ' is linked to position α'.

Herein, E is an acidic group having a formula:

(I)

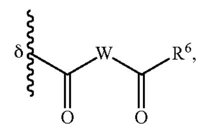

where W represents $—(CR^4R^5)_l—$, where $R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide, $R^6$ is selected from hydroxyl or $NR^7R^8$, where $R^7$ and $R^8$ are independently selected from the group consisting of hydrogen, alkyl, hydroxyl, and

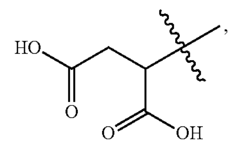 [SMILES: *C(CC(=O)O)C(=O)O]

and I is an integer from 10 to 20. Herein, when D is not a bond, then position δ is linked to position δ', when C is not a bond and D is a bond, then position δ is linked to position γ, when B is not a bond, C is a bond and D is a bond, then position δ is linked to position β, when A is not a bond, and all of B, C, and D are bond, then position δ is linked to position α'.

In some embodiments of the first CRM, A is a bond or

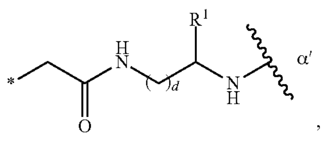

where d is an integer from 1 to 4, $R^1$ is hydrogen; B is a bond or

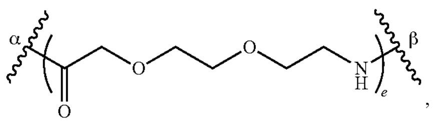

where e is an integer from 1 to 4, wherein position α is linked to position α'; C is

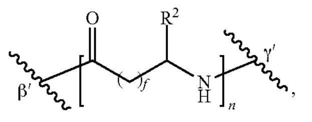

where $R^2$ is —COOH, f is an integer from 1 to 4, n is an integer from 1 to 25, and when B is not bond, then position β' is linked to position β, or when B is bond, then position β' is linked to position α'; D is a bond; regarding E, each of $R^4$ and $R^5$ is hydrogen, $R^6$ is hydroxyl, I is an integer from 10 to 20, and position δ is linked to position γ.

In some embodiments of the first CRM, d is 1, e is 2, f is 1, n is 1, and I is an integer from 14 to 20.

In some embodiments of the first CRM, I is 16.

In some embodiments of the polypeptide conjugate, the first CRM residue is lysine residue, wherein: A is a bond and B is

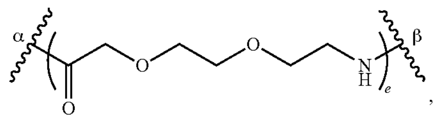

In some embodiments, the first CRM comprises Moiety A (HOOC-(CH2)16-CO-gGlu-2XADO), the Moiety A having the structure of below formula:

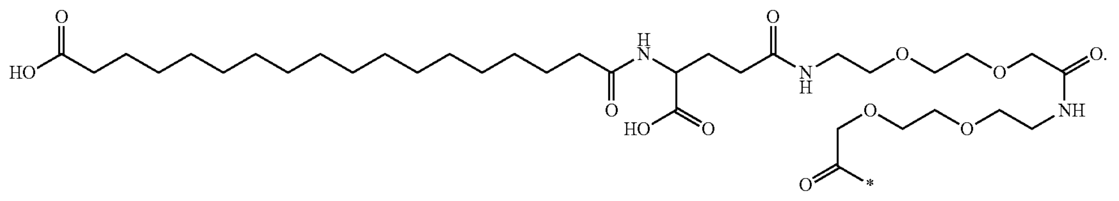 [SMILES: *C(=O)COCCOCCNC(=O)COCCOCCNC(=O)CCC(NC(=O)CCCCCCCCCCCCCCCCC(=O)O)C(=O)O]

In some embodiments of the polypeptide conjugate, the first CRM residue is cysteine residue, wherein A is

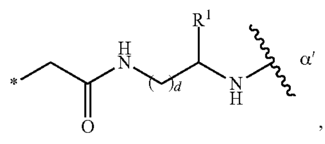

and B is

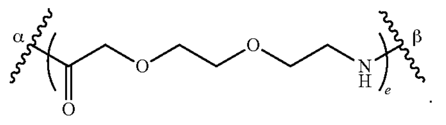

In some embodiments, the first CRM comprises Moiety B (HOOC-(CH2)16-CO-gGlu-2XADO-EDA-CO-CH2), the Moiety B having the structure of below formula:

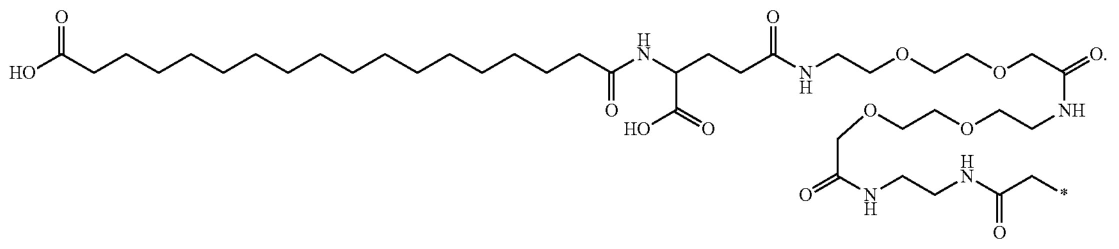 [SMILES: *CC(=O)NCCNC(=O)COCCOCCNC(=O)COCCOCCNC(=O)CCC(NC(=O)CCCCCCCCCCCCCCCCC(=O)O)C(=O)O]

In certain embodiments, the polypeptide conjugate provided herein is mono-conjugated, and has the CRM conjugated to the peptide linker but not to the biologically active peptide (e.g. GLP-1).

In some embodiments of the mono-conjugated polypeptide conjugate, the first CRM residue is lysine residue, and the polypeptide conjugate comprises only one lysine residue.

In some embodiments of the mono-conjugated polypeptide conjugate, the first CRM residue is cysteine residue, and the polypeptide conjugate comprises only one cysteine residue.

In some embodiments, the GLP-1 comprises an amino acid sequence selected from the group consisting of: SEQ ID NOS: 3, 5, 6, 8, and 9.

Herein, in some embodiments, the polypeptide portion comprises an amino acid sequence selected from the group consisting of SEQ ID NO: 52, 55, 56, 60-62, 66-71, and 75-80; and the first CRM residue is lysine residue or cysteine residue at a position selected from the group consisting of 60, 68, and 76.

The following lists certain embodiments of the mono-conjugated polypeptide conjugate disclosed herein:

- the polypeptide portion comprises an amino acid sequence of SEQ ID NO: 52, and is conjugated with the first CRM at 76K;
- the polypeptide portion comprises an amino acid sequence of SEQ ID NO: 55, and is conjugated with the first CRM at 68K;
- the polypeptide portion comprises an amino acid sequence of SEQ ID NO: 56, and is conjugated with the first CRM at 60K;
- the polypeptide portion comprises an amino acid sequence of SEQ ID NO: 60, and is conjugated with the first CRM at 76K;
- the polypeptide portion comprises an amino acid sequence of SEQ ID NO: 61, and is conjugated with the first CRM at 68K;
- the polypeptide portion comprises an amino acid sequence of SEQ ID NO: 62, and is conjugated with the first CRM at 60K;
- the polypeptide portion comprises an amino acid sequence of SEQ ID NO: 66, and is conjugated with the first CRM at 76C;
- the polypeptide portion comprises an amino acid sequence of SEQ ID NO: 67, and is conjugated with the first CRM at 68C;
- the polypeptide portion comprises an amino acid sequence of SEQ ID NO: 68, and is conjugated with the first CRM at 60C;
- the polypeptide portion comprises an amino acid sequence of SEQ ID NO: 69, and is conjugated with the first CRM at 76C;
- the polypeptide portion comprises an amino acid sequence of SEQ ID NO: 70, and is conjugated with the first CRM at 68C;
- the polypeptide portion comprises an amino acid sequence of SEQ ID NO: 71, and the first CRM is conjugated with the polypeptide portion at 60C;
- the polypeptide portion comprises an amino acid sequence of SEQ ID NO: 75, and is conjugated with the first CRM at 76C;
- the polypeptide portion comprises an amino acid sequence of SEQ ID NO: 76, and is conjugated with the first CRM at 68C;
- the polypeptide portion comprises an amino acid sequence of SEQ ID NO: 77, and is conjugated with the first CRM at 60C;
- the polypeptide portion comprises an amino acid sequence of SEQ ID NO: 78, and is conjugated with the first CRM at 76C;
- the polypeptide portion comprises an amino acid sequence of SEQ ID NO: 79, and is conjugated with the first CRM at 68C; or
- the polypeptide portion comprises an amino acid sequence of SEQ ID NO: 80, and is conjugated with the first CRM at 60C.

In certain embodiment of the polypeptide conjugate, the polypeptide portion comprises an amino acid sequence of SEQ ID NO: 52, and the first CRM residue is 76K. More specifically, certain embodiment of the polypeptide conjugate has the structure shown below:

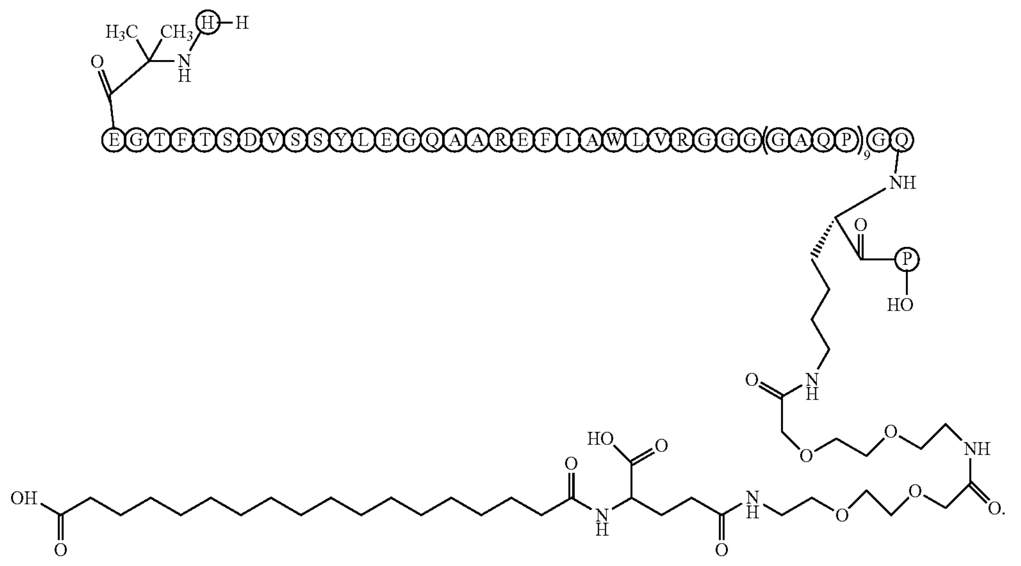

In certain embodiment of the polypeptide conjugate, the polypeptide portion comprises an amino acid sequence of SEQ ID NO: 60, and the first CRM residue is 76K. More specifically, certain embodiment of the polypeptide conjugate has the structure shown below:

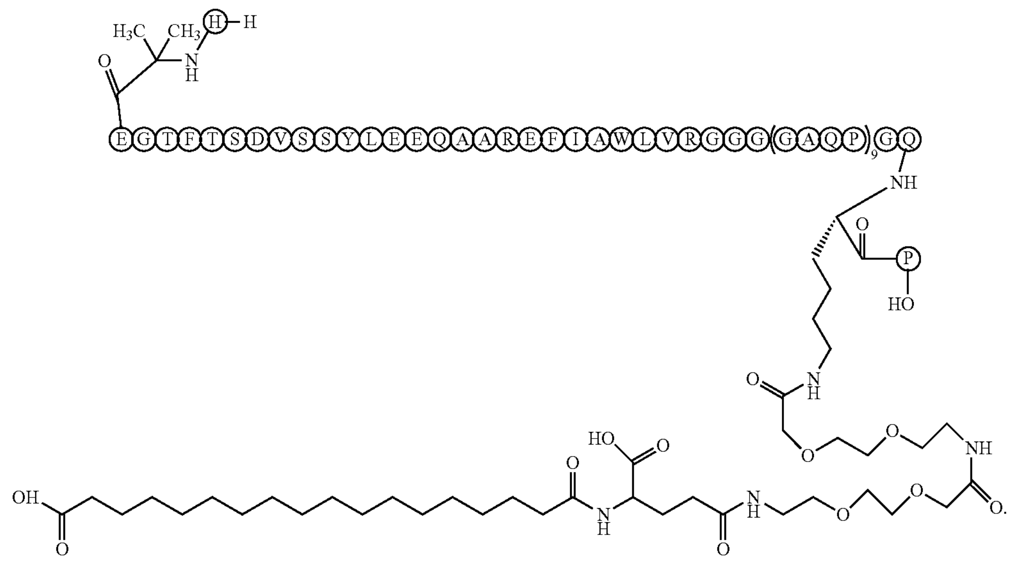

In some embodiments, the polypeptide conjugate is a double-conjugated polypeptide conjugate and further comprises a second CRM conjugated to a second CRM residue.

In some embodiments of the double-conjugated polypeptide conjugate, the first CRM residue and the second CRM residue are both lysine residues, and the polypeptide conjugate comprises only two lysine residues.

Herein optionally, the second CRM residue is in the GLP-1, and is optionally selected from the group consisting of K23, K26, K27, K30 and K34.

In some embodiments, the second CRM residue is K26.

In some embodiments of the double-conjugated polypeptide conjugate, the first CRM residue and the second CRM residues are both cysteine residues, and the polypeptide conjugate comprises only two cysteine residues.

Herein optionally, the second CRM residue is in the GLP-1, and is optionally selected from the group consisting of C23, C26, C27, C30 and C34.

In some embodiments, the second CRM residue is C26.

Herein, the positions as described above (i.e. 23, 26, 27, 30 and 34, either as K or C) are referenced relative to the wildtype human GLP-1 (SEQ ID NO: 1) and starts from the N-terminus thereof.

Herein, according to some embodiments, the second CRM is identical to the first CRM. In some embodiments, the second CRM residue and the first CRM residue are both lysine residues or both cysteine residues.

In some embodiments of the double-conjugated polypeptide conjugate, the GLP-1 comprises an amino acid sequence selected from the group consisting of: SEQ ID NOS: 3, 4, 6 and 7.

In some embodiments, the polypeptide portion comprises an amino acid sequence selected from the group consisting of SEQ ID NO: 51, 53, 54, 57-59, 63-65, and 72-74, 85 and 86; the first CRM residue is lysine residue or cysteine residue at a position selected from the group consisting of 68, 76, and 84; and the second CRM residue is lysine residue or cysteine residue at position 26.

The following list certain embodiments of double-conjugated polypeptide conjugate as disclosed herein:

- the polypeptide portion comprises an amino acid sequence of SEQ ID NO: 51, and is conjugated with the first CRM and the second CRM respectively at 26K and 76K;
- the polypeptide portion comprises an amino acid sequence of SEQ ID NO: 53, and is conjugated with the first CRM and the second CRM respectively at 26K and 84K;
- the polypeptide portion comprises an amino acid sequence of SEQ ID NO: 54, and is conjugated with the first CRM and the second CRM respectively at 26K and 68K;
- the polypeptide portion comprises an amino acid sequence of SEQ ID NO: 57, and is conjugated with the first CRM and the second CRM respectively at 26K and 76K;
- the polypeptide portion comprises an amino acid sequence of SEQ ID NO: 58, and is conjugated with the first CRM and the second CRM respectively at 26K and 84K;
- the polypeptide portion comprises an amino acid sequence of SEQ ID NO: 59, and is conjugated with the first CRM and the second CRM respectively at 26K and 68K;
- the polypeptide portion comprises an amino acid sequence of SEQ ID NO: 85, and is conjugated with the first CRM and the second CRM respectively at 26K and 96K;
- the polypeptide portion comprises an amino acid sequence of SEQ ID NO: 86, and is conjugated with the first CRM and the second CRM respectively at 26K and 60K;
- the polypeptide portion comprises an amino acid sequence of SEQ ID NO: 63, and is conjugated with the first CRM and the second CRM respectively at 26C and 84C;

the polypeptide portion comprises an amino acid sequence of SEQ ID NO: 64, and is conjugated with the first CRM and the second CRM respectively at 26C and 76C;

the polypeptide portion comprises an amino acid sequence of SEQ ID NO: 65, and is conjugated with the first CRM and the second CRM respectively at 26C and 68C;

the polypeptide portion comprises an amino acid sequence of SEQ ID NO: 72, and is conjugated with the first CRM and the second CRM respectively at 26C and 84C;

the polypeptide portion comprises an amino acid sequence of SEQ ID NO: 73, and is conjugated with the first CRM and the second CRM respectively at 26C and 76C; or the polypeptide portion comprises an amino acid sequence of SEQ ID NO: 74, and is conjugated with the first CRM and the second CRM respectively at 26C and 68C.

In certain embodiments, the polypeptide portion comprises an amino acid sequence of SEQ ID NO: 57, and is conjugated with the first CRM and the second CRM respectively at 26K and 76K. More specifically, certain embodiment of the polypeptide conjugate has the structure shown below:

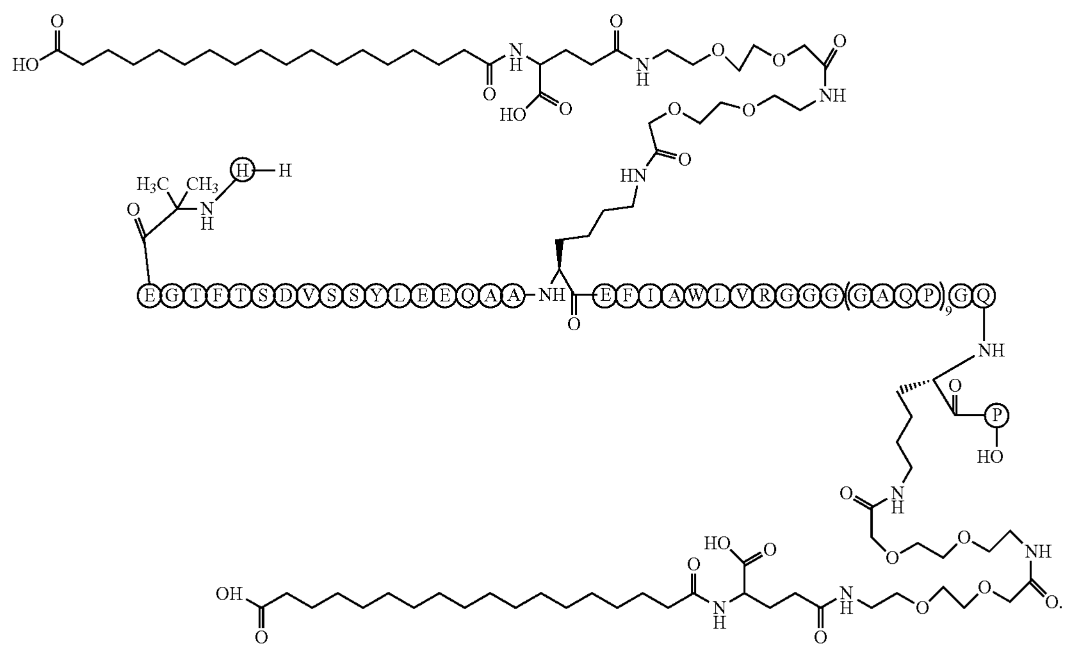

polypeptide portion to thereby obtain the single-conjugated or double-conjugated polypeptide conjugate.

In certain embodiments of the pharmaceutical composition provided herein, the absorption enhancing excipient comprises a salt of N-(8-(2-hydroxybenzoyl) amino) caprylic acid.

Herein the salt can be selected from the group consisting of a sodium salt, a potassium salt, and an ammonium salt.

In certain embodiments, the salt is a sodium salt, i.e. the pharmaceutical composition substantially comprises sodium N-(8-(2-hydroxybenzoyl) amino) caprylic acid (SNAC) as the absorption enhancing excipient.

Optionally, the pharmaceutical composition further includes other pharmaceutically acceptable excipients.

In certain embodiments, the pharmaceutical composition further comprises at least one lubricant, each selected from the group consisting of magnesium stearate, calcium stearate, zinc stearate, colloidal silica, glyceryl behenate, polyethylene oxide polymers, sodium lauryl sulfate, magnesium lauryl sulfate, sodium oleate, sodium stearyl fumarate, stearic acid, hydrogenated vegetable oil, light mineral oil, silicon dioxide, alkyl sulfate, sodium benzoate, polyethylene glycol, talc, wax, and glyceride.

In certain embodiments, the at least one lubricant comprises or consists of magnesium stearate.

Herein, in order to obtain the polypeptide conjugate in the pharmaceutical composition provided in the first aspect, a polynucleotide encoding the polypeptide portion (or fragment thereof) of the polypeptide conjugate can be designed, which can be operably arranged in a vector. The vector can be transferred in a host cell, such as a prokaryotic cell or eukaryotic cell, and the host cell can be cultured under a condition that allows expression of the polynucleotide, thereby obtaining the polypeptide portion of the polypeptide conjugate. Herein optionally, the polypeptide portion is expressed as soluble proteins. After obtaining the polypeptide portion, the CRM can be further conjugated to the In certain embodiments, the pharmaceutical composition further comprises at least one filler, each selected from the group consisting of microcrystalline cellulose (MCC), cellulose powder, hydroxymethylcellulose, hydroxyethylcellulose, hydroxypropylcellulose, hydroxy-propylmethylcellulose, dibasic calcium phosphate, corn starch, and pregelatinized starch.

Optionally, the pharmaceutical composition may further comprise at least one binder, each selected from the group consisting of povidone, lactose, hydroxypropylcellulose, L-hydroxypropylcellulose, hypromellose (HPMC), methylcellulose polymers, hydroxyethylcellulose, ethylcellulose, sodium carboxymethylcellulose, other cellulose derivatives, sucrose, dextrins, maltodextrins, starches, calcium lactate, calcium carbonate, acacia, sodium alginate, agar, carrageenan, gelatin, guar gum, pectin, PEG.

In certain embodiments, the pharmaceutical composition comprises no filler or binder.

In certain embodiments, the pharmaceutical composition consists of the polypeptide conjugate, sodium N-(8-(2-hydroxybenzoyl) amino) caprylic acid (SNAC), and magnesium stearate.

In certain embodiments, the polypeptide conjugate is single-conjugated, and the first CRM is the only one CRM in the conjugate portion of the polypeptide conjugate. Optionally, the first CRM residue is lysine residue, and further optionally, and the first CRM comprises Moiety A (HOOC-(CH2)16-CO-gGlu-2XADO), the Moiety A having the structure of below formula:

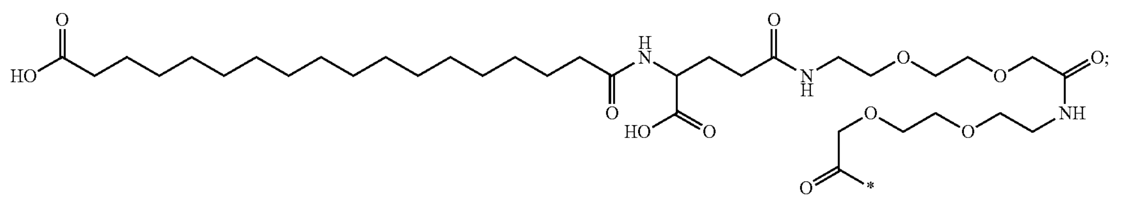 [SMILES: *C(=O)COCCOCCNC(=O)COCCOCCNC(=O)CCC(NC(=O)CCCCCCCCCCCCCCCCC(=O)O)C(=O)O]

wherein the dosage form comprises: approximately 0.5-50 mg (0.5-50 mg (e.g. 0.5-10 mg, 0.5-2.5 mg, 2.5-5 mg, 5-10 mg, 10-20 mg, or 20-50 mg) of the polypeptide conjugate; and approximately 50-300 mg (e.g. 100-300 mg) of SNAC.

In certain embodiments, the pharmaceutical composition further comprises 1-10 mg lubricant.

In certain embodiments of the pharmaceutical composition, the polypeptide portion of the polypeptide conjugate comprises an amino acid sequence of SEQ ID NO: 60, and is conjugated with the first CRM at 76K.

In certain embodiments of the pharmaceutical composition, the polypeptide portion of the polypeptide conjugate comprises an amino acid sequence of SEQ ID NO: 52, and is conjugated with the first CRM at 76K.

In certain embodiments, the SNAC constitutes from about 80% to about 98%, about 81% to about 98%, about 82% to about 98%, about 83% to about 98%, about 84% to about 98%, about 85% to about 98%, about 86% to about 98%, about 87% to about 98%, about 88% to about 98%, about 89% to about 98%, about 90% to about 98% w/w of the unit dosage form.

In certain embodiments, the unit dosage form thereof comprises up to 300 mg, up to 250 mg, up to 200 mg, up to 150 mg, up to 100 mg, or up to 50 mg SNAC.

In certain embodiments, the unit dosage form thereof comprises about 50 mg to about 300 mg, about 75 mg to about 300 mg, about 100 mg to about 300 mg, about 100 mg to 500 mg, about 150 mg to about 300 mg, about 200 mg to about 300 mg SNAC.

In certain embodiments, the SNAC constitutes from about 91% to about 98% w/w of the excipients in the unit dosage form.

In certain embodiments, the polypeptide conjugate constitutes from about 0.1% w/w to about 20% w/w of the unit dosage form.

In certain embodiments, the unit dosage form thereof comprises up to 50 mg, up to 40 mg, up to 30 mg, up to 20 mg, or up to 10 mg of the polypeptide conjugate.

In certain embodiments, the unit dosage form thereof comprises 0.5-50 mg, 0.5-40 mg, 0.5-30 mg, 0.5-20 mg, 0.5-10 mg, 0.5-5 mg, 0.5-2.5 mg, 2.5-5 mg, 2.5-10 mg, 2.5-15 mg, 2.5-20 mg, 5-10 mg, 10-20 mg, 10-30 mg, or 20-50 mg of the polypeptide conjugate.

In certain embodiments, the unit dosage form comprises 1-10 mg magnesium stearate.

In certain embodiments, the unit dosage form comprises approximately 0.5-50 mg of the polypeptide conjugate, approximately 50-300 mg of SNAC, and approximately 1-10 mg magnesium stearate.

In certain embodiments, the unit dosage form comprises: approximately 0.5-10 mg of the polypeptide conjugate, approximately 50-300 mg of SNAC, and approximately 1-10 mg magnesium stearate.

In certain embodiments, the unit dosage form comprises: approximately 10-20 mg of the polypeptide conjugate, approximately 100-300 mg of SNAC, and approximately 1-10 mg magnesium stearate; or In certain embodiments, the unit dosage form comprises: approximately 20-50 mg of the polypeptide conjugate, approximately 200-300 mg of SNAC, and approximately 1-10 mg magnesium stearate.

In certain embodiments of the pharmaceutical composition, the polypeptide conjugate is double-conjugated, and the conjugate portion of the polypeptide conjugate further comprises a second CRM conjugated to a second CRM residue in the polypeptide portion. Optionally, the second CRM residue is lysine residue, and further optionally, each of the first CRM and the second CRM comprises Moiety A (HOOC-(CH2)16-CO-gGlu-2XADO), the Moiety A having the structure of below formula:

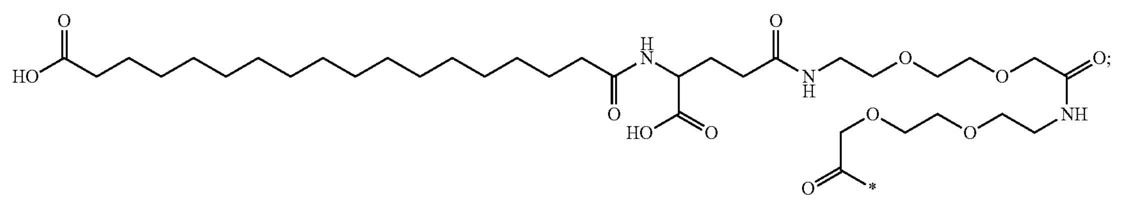 [SMILES: *C(=O)COCCOCCNC(=O)COCCOCCNC(=O)CCC(NC(=O)CCCCCCCCCCCCCCCCC(=O)O)C(=O)O]

wherein a dosage form of the pharmaceutical composition comprises: approximately 10-100 mg (e.g. 10-20 mg, 10-50 mg, 20-30 mg, 20-40 mg, 20-50 mg, 40-50 mg, 50-70 mg, or 80-100 mg, etc.) of the polypeptide conjugate; and approximately 50-500 mg (e.g. 50-100 mg, 100-200 mg, 250-500 mg, etc.) of SNAC. In some embodiments, the pharmaceutical composition further comprises 1-20 mg lubricant.

In some embodiments of the pharmaceutical composition, the polypeptide portion of the polypeptide conjugate comprises an amino acid sequence of SEQ ID NO: 57, and is conjugated with the first CRM and the second CRM respectively at 26K and 76K.

In certain embodiments, the SNAC constitutes from about 60% to about 96%, about 62% to about 96%, about 65% to about 96%, about 66% to about 96%, about 67% to about 96%, about 68% to about 96%, about 70% to about 96%, about 72% to about 96%, about 75% to about 96%, about 78% to about 96%, about 80% to about 96%, about 86% to about 96%, about 87% to about 96%, w/w of the unit dosage form.

In certain embodiments, the unit dosage form thereof comprises up to 500 mg, up to 450 mg, up to 400 mg, up to 350 mg, up to 300 mg, up to 250 mg, up to 200 mg, up to 150 mg, up to 100 mg SNAC.

In certain embodiments, the unit dosage form thereof comprises about 100 mg to about 500 mg, about 100 mg to about 450 mg, about 100 mg to about 400 mg, about 100 mg to about 350 mg, about 100 mg to about 300 mg SNAC.

In certain embodiments, the SNAC constitutes from about 91% to about 98% w/w of the excipients in the unit dosage form.

In certain embodiments, the polypeptide conjugate constitutes at least 1% w/w and at most 32% w/w of the unit dosage form.

In certain embodiments, the unit dosage form thereof comprises up to 100 mg, up to 90 mg, up to 80 mg, up to 70 mg, up to 60 mg, up to 50 mg, up to 40 mg, up to 30 mg, up to 20 mg, up to 10 mg of the polypeptide conjugate.

In certain embodiments, the unit dosage form thereof comprises 10-100 mg, 10-90 mg, 10-80 mg, 10-70 mg, 10-60 mg, 10-50 mg, 10-40 mg, 20-100 mg, 20-90 mg, 20-80 mg, 20-70 mg, 20-60 mg, 20-50 mg, 20-40 mg, of the polypeptide conjugate.

In certain embodiments, the the unit dosage form comprises 1-20 mg magnesium stearate.

In certain embodiments, the unit dosage form thereof comprises: approximately 10-100 mg of the polypeptide conjugate; approximately 100-500 mg of SNAC, and approximately 1-20 mg magnesium stearate.

In certain embodiments, the unit dosage form comprises: a) approximately 10-20 mg of the polypeptide conjugate, approximately 100-300 mg of SNAC, and approximately 1-20 mg magnesium stearate.

In certain embodiments, the unit dosage form comprises: approximately 20-40 mg of the polypeptide conjugate, approximately 200-300 mg of SNAC, and approximately 1-20 mg magnesium stearate.

In certain embodiments, the unit dosage form comprises: approximately 20-50 mg of the polypeptide conjugate, approximately 200-300 mg of SNAC, and approximately 1-20 mg magnesium stearate.

In certain embodiments, the unit dosage form comprises: approximately 40-50 mg of the polypeptide conjugate, approximately 200-300 mg of SNAC, and approximately 1-20 mg magnesium stearate.

In certain embodiments, the unit dosage form comprises: approximately 50-100 mg of the polypeptide conjugate, approximately 300-500 mg of SNAC, and approximately 1-20 mg magnesium stearate.

In certain embodiments, the unit dosage form comprises approximately 0.5 mg, 1 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, or 100 mg of the polypeptide conjugate.

In any of the embodiments of the pharmaceutical composition as mentioned above, the dosage form thereof can be in a form selected from the group consisting of tablets, capsules, sachets, chewing gums, and powders.

In certain embodiments, the dosage of the pharmaceutical composition is in a form of tablets.

In a second aspect, the present disclosure provides a method of preventing or treating a metabolic disorder in a subject in need thereof, comprising administering a therapeutically effective amount of the polypeptide conjugate of the first aspect.

In certain embodiments, the metabolic disorder is diabetes, obesity, overweight, non-alcoholic steatohepatitis (NASH), cardiovascular like dyslipidemia, atherosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC), or Alzheimer's disease.

In certain embodiments, the diabetes can be any form of diabetes, including without limitation, hyperglycemia, type 2 diabetes, impaired glucose tolerance, type 1 diabetes, non-insulin dependent diabetes, MODY (maturity onset diabetes of the young), gestational diabetes, and elevated level of HbA1C.

In certain embodiments, the metabolic disorder is Alzheimer's disease. In certain embodiments, the present disclosure provides a method of preventing or treating Alzheimer's disease in a subject in need thereof, comprising administering a therapeutically effective amount of the polypeptide conjugate or a pharmaceutical composition provided herein.

In a third aspect, the present disclosure provides a method of managing body weight in a subject in need thereof, comprising administering a therapeutically effective amount of the polypeptide conjugate provided herein, thereby managing body weight of the subject.

In a fourth aspect, the present disclosure provides a method of reducing food intake in a subject in need thereof, comprising administering a therapeutically effective amount of the polypeptide conjugate provided herein, thereby reducing food intake of the subject.

In a fifth aspect, the present disclosure provides a method of reducing body weight in a subject in need thereof, comprising administering a therapeutically effective amount of the polypeptide conjugate provided herein, thereby reducing body weight of the subject.

In any of the method as mentioned above in the second through fifth aspect, the subject can be human.

In certain embodiments, the subject has a fasting blood glucose level of 125 mg/dL or greater.

In certain embodiments, the subject has a body mass index (BMI) of at least or higher than 25.

In certain embodiments, the pharmaceutical composition is administered at a dosing regimen that is, or is no more frequently than, twice daily, once daily, once every 2 days, once every 3 days, or once weekly, once every two weeks, once every three weeks, or once monthly.

In certain embodiments, the pharmaceutical composition is administered twice daily, once daily, twice-weekly, once-weekly, once bi-weekly, once every three weeks, once monthly, or once every two months.

In certain embodiments, the dosing regimen has a dosing interval ranging from about once every 3 days to about once per month, or from about once weekly to about once per month.

In certain embodiments, the pharmaceutical composition is administered orally.

Throughout the present disclosure, the articles "a," "an," and "the" are used herein to refer to one or to more than one (i.e., to at least one) of the grammatical object of the article. By way of example, "a fusion polypeptide" means one fusion polypeptide or more than one fusion polypeptides.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Similarly, ranges delimited by "at least" are understood to include the lower value provided and all higher numbers.

As used herein, "about" or "approximately" is understood to include within three standard deviations of the mean or within standard ranges of tolerance in the specific art. In certain embodiments, about is understood a variation of no more than 0.5.

The articles "a" and "an" are used herein to refer to one or more than one (i.e. to at least one) of the grammatical object of the article. By way of example, "an element" means one element or more than one element.

The term "including" is used herein to mean, and is used interchangeably with, the phrase "including but not limited to". Similarly, "such as" is used herein to mean, and is used interchangeably, with the phrase "such as but not limited to".

The term "or" is used inclusively herein to mean, and is used interchangeably with, the term "and/or," unless context clearly indicates otherwise.

BRIEF DESCRIPTION OF THE FIGURES

FIG. 1A shows body weight loss after Molecule 012 or Molecule 001 treatment from Day1 to Day 8. FIG. 1B shows body weight loss after Molecules 007, 008, 012 and 016 treatment from Day1 to Day 8. Data are indicated as mean values and standard error (SEM). Semaglutide was tested in parallel as a comparative control.

FIGS. 2A, 2B, 2C, 2D and 2E show in vivo activities of Molecules 001, 002, 012 and 019 in db/db mice. FIG. 2A shows fasting glucose after Molecule 001 single dose treatment. FIG. 2B shows fasting glucose after Molecule 002 single dose treatment. Data are indicated as mean values and standard error (SEM). FIG. 2C shows non-fasting glucose after Molecule 012 single dose treatment. FIG. 2D shows non-fasting glucose after Molecule 019 single dose treatment, and FIG. 2E shows area under the curve for 0-48 hours for non-fasting glucose after Molecule 019 single dose treatment. To evaluate the glucose, 10-week old male db/db mice were administered subcutaneously with the designated GLP-1 polypeptide conjugates at the indicated dosage. Fasting glucose (FIGS. 2A and 2B) or non-fasting glucose (FIGS. 2C and 2D) was measured on different times and five animals were used for each group. Delta blood glucose is glucose subtracted by baseline level. Data are indicated as mean values and standard error (SEM).

FIG. 3A shows body weight change with dose titrations of Molecule 012 at 10, 30 and 100 nmol/kg. FIG. 3B shows fasting glucose change upon treatment. Data are expressed as mean values and standard error (SEM).

FIGS. 4C and 4D respectively how the dissolution profiles of the GLP-1 (FIG. 4C) and SNAC (FIG. 4D) of different pharmaceutical compositions for Molecule 012.

FIG. 5A shows quadrant occupancy change with Molecule 012 at 30 and 100 nmol/kg, respectively. FIG. 5B shows alternation percentage change with Molecule 012 at 30 and 100 nmol/kg, respectively. FIG. 5C shows Ap plaque deposition in cortex change with Molecule 012 at 30 and 100 nmol/kg, respectively. FIG. 5D shows Ap plaque deposition in hippocampus change with Molecule 012 at 30 and 100 nmol/kg, respectively. FIG. 5E shows the number of neuron in hippocampus change with Molecule 012 at 30 and 100 nmol/kg, respectively. Data are expressed as mean values and standard error (SEM). Wild type mice treated with vehicle was used as control. Alzheimer' disease (APP/PS1) mice treated with vehicle was also used as control. Alzheimer' disease (APP/PS1) mice treated with semaglutide was also used as control.

FIGS. 6A-6E shows all the sequences disclosed in the present disclosure (except for SEQ ID NO: 81).

DETAILED DESCRIPTION

Figure 1A:
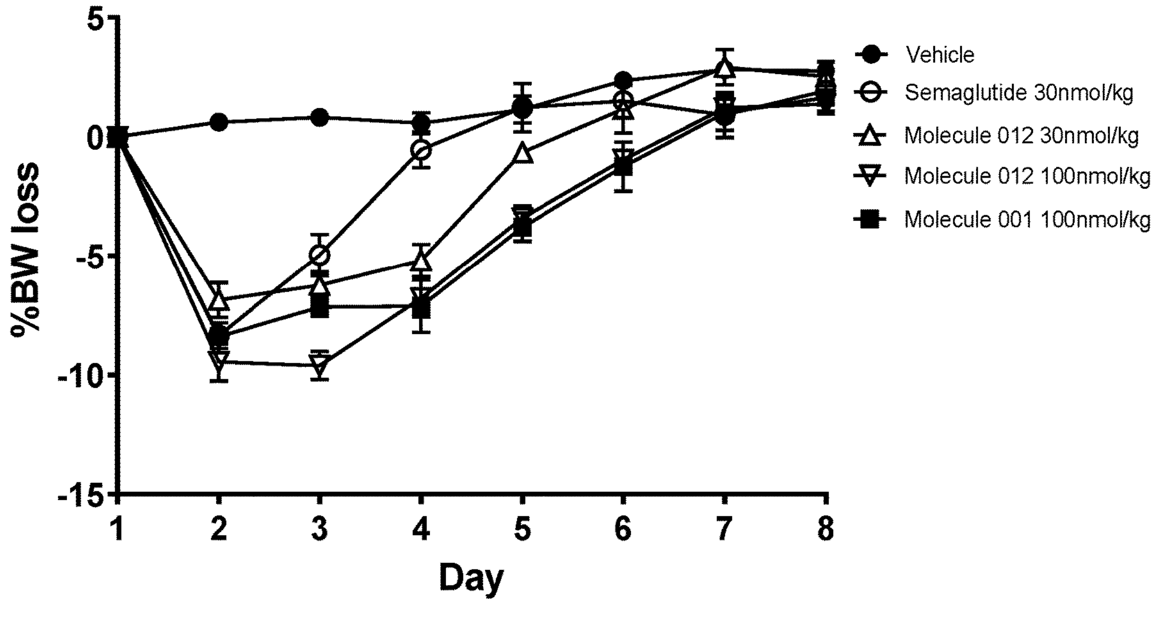
FIGS. 1A to 1B show in vivo activities of test Molecules in C57BL/6 mice. To evaluate the body weight, 10-week old male C57BL/6 mice were dosed subcutaneously with testing drug substances once.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein, including publications, patents and patent applications are incorporated herein by reference in their entirety.

Definitions

The term "amino acid" as used herein refers to an organic compound containing amine ($—NH_2$) and carboxyl (—COOH) functional groups, along with a side chain specific to each amino acid.

The term "naturally occurring" amino acid residue, as used herein, refers to an amino acid residue found in native proteins or peptides, all in their D and L stereoisomers if their structure allows such stereoisomeric forms. Examples of naturally occurring amino acid residues include, but not limited to, 20 standard amino acids, including, glycine (Gly or G), alanine (Ala or A), valine (Val or V), leucine (Leu or L), isoleucine (Ile or I), serine (Ser or S), cysteine (Cys or C), threonine (Thr or T), methionine (Met or M), proline (Pro or P), phenylalanine (Phe or F), tyrosine (Tyr or Y), tryptophan (Trp or W), histidine (His or H), lysine (Lys or K), arginine (Arg or R), aspartate (Asp or D), glutamate (Glu or E), asparagine (Asn or N), and glutamine (Gln or Q), and their natural analogs, such as canavanine, pyrrolysine (PYL), selenocysteine, pyrroline-carboxy-lysine (PCL), Sarcosine, beta-Alanine, phosphoserine, -carboxyglutamate, and ornithine. Examples of naturally occurring amino acid residues in their D stereoisomer include, for example, D-aspartate, D-Serine, D-Cysteine, D-Alanine, D-glutamate and so on.

An "amino acid analog" is a compound that has the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

A "non-natural" amino acid residue, as used herein, refers to any amino acid residues that are not found in nature, including without limitation, a modified amino acid residue, and/or an amino acid mimetic, which is not one of the known naturally occurring amino acids, yet functions in a manner similar to the naturally occurring amino acids. Modified amino acid or a mimetic can be generated by addition of a chemical entity such as a carbohydrate group, a phosphate group, a farnesyl group, an isofamesyl group, a fatty acid group, a linker for conjugation, functionalization, or other modification, etc. A non-natural amino acid can also refer to an amino acid manufactured by chemical synthesis. Exemplary non-natural amino acids include, but not limited to, 2-Aminoisobutyric acid (Aib), imidazole-4-acetate (IA), imidazolepropionic acid (IPA), a-aminobutyric acid (Abu), tert-butylglycine (Tle), b-alanine, 3-aminomethyl benzoic acid, anthranilic acid, des-amino-histidine (abbreviated DesaminoHis, alternative name imidazopropionic acid, abbreviated Impr), the beta analogues of amino acids such as β-alanine, 2-amino-histidine, β-hydroxy-histidine, homohistidine, Nα-acetyl-histidine, α-fluoro-methyl-histidine, α-methyl-histidine, α,α-dimethyl-glutamic acid, m-CF3-phenylalanine, α,β-diaminopropionic acid (abbreviated Dap), 3-pyridylalanine, 2-pyridylalanine or 4-pyridylalanine, (1-aminocyclopropyl)carboxylic acid, (1-aminocyclobutyl)-carboxylic acid, (1-aminocyclopentyl)carboxylic acid, (1-aminocyclohexyl)carboxylic acid, (1-aminocycloheptyl)carboxylic acid, and (1-aminocyclooctyl)carboxylic acid.

Introduction of non-natural amino acids into a polypeptide may be realized by the technology described in Wang et al., Science 292:498-500, 2001; Deiters et al., J Am Chem Soc 125:1 1782-1 1783, 2003; Wang and Schultz, Science 301:964-967, 2003; Zhang et al., Science 303:371-373, 2004 or in U.S. Pat. No. 7,083,970. Briefly, some of these expression systems involve site-directed mutagenesis to introduce a stop codon, such as an amber (UAG), ochre (UAA), and opal (UGA) codons) into the open reading frame encoding a fusion polypeptide of the present disclosure. Other codons, such as a four-base codon (e.g. AGGA, AGGU, CGGU, CGCU, CGAU, CCCU, CUCU, CUAU, and GGGU), a five-base codon, a six-base codon, etc. can also be introduced into the expression systems for non-natural amino acids. Such expression vectors are then introduced into a host that can utilize a tRNA specific for the introduced stop codon or other codons and carried with the non-natural amino acid of choice. For another example, non-natural amino acid can be chemically synthesized and inserted into or attached to a polypeptide by chemical reaction such as acylation.

"Percent (%) sequence identity" is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues is not considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "functional form" as used herein, refers to different forms (such as variants, fragments, fusions, derivatives and mimetics) of the parent molecule, which, despite of having difference in amino acid sequences or in chemical structures, still retains substantial biological activity of the parent molecule. The expression "retain substantial biological activity", as used herein, means exhibiting at least part of (for example, no less than about 20%, 30%, 40%, 50%, 60%, 70%, 80%, or 90%) or all of the biological activity of the parent molecule. A functional form of a parent polypeptide may include both naturally-occurring variant forms and non-naturally occurring forms such as those obtained by recombinant methods or chemical synthesis. The functional forms may contain non-natural amino acid residues.

The term "variant" as used herein refers to a polypeptide having at least 70% sequence identity to the parent polypeptide. A variant may differ from the parent peptide by one or more amino acid residues. For example, a variant may have substitutions, additions, deletions, insertions, or truncations of one more amino acid residue of the parent polypeptide.

The term "fragment" as used herein refers to partial sequence of the parent polypeptide of any length. A fragment can still retain at least partial function of the parent polypeptide.

The term "derivative" as used herein refers to a chemically modified polypeptide or fusion polypeptide, in which one or more well-defined number of substituent groups have been covalently attached to one or more specific amino acid residues of the polypeptide or fusion polypeptide. Exemplary chemical modification can be, e.g. alkylation, acylation, esterification, amidation, phosphorylation, glycosylation, labeling, methylation of one or more amino acids, or conjugation with one or more moieties.

The term "mimetics" as used herein refers to molecular structures that serve as substitutes for amino acids, peptides, polypeptides, or fusion polypeptide. For example, amino acid mimetics, as used herein, can be synthetic structures (either known or yet unknown), which may or may not be an amino acid, but retain the functional features of the parent amino acids while the structure of the amino acid mimetic is different from the structure of the parent amino acid. Examples include a methacryloyl or acryloyl derivative of an amide, β-, γ-, δ-imino acids (such as piperidine-4-carboxylic acid) and the like.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the fusion polypeptide, at least one promoter (e.g., SV40, CMV, EF-1 a) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBl, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on.

Polypeptide Conjugates

In one aspect, the present disclosure provides a polypeptide conjugate, which comprises a polypeptide portion and a conjugate portion. The polypeptide portion comprises a single biologically active peptide and a peptide linker. The biologically active peptide is attached to N-terminus of the peptide linker and comprises a GLP-1 receptor agonist. The conjugate portion comprises a first clearance-reducing moiety (CRM) conjugated to a first CRM residue in the peptide linker. Herein, the first CRM residue is at least 5 amino acid residues (exclusive of the CRM residue) away from the C-terminal amino acid residue of the biologically active peptide (e.g. the GLP-1 receptor agonist).

The term "peptide" and "polypeptide" are used interchangeably herein and refer a polymer of amino acid residues linked by covalent bonds such as peptide bonds. A peptide or polypeptide as provided herein can comprise naturally occurring or non-natural amino acid residues, or both. Polypeptides and peptides provided herein can comprise any suitable length of amino acid residues, for example, from at least 5, 10, 20, 30, 40, 50, 60, 70, 80, 90, 100, 200, 300, 400, 500, 600, 700, 800, 900, 1000, or more amino acid residues in length.

The polypeptide conjugate comprises a single, i.e., only one, biologically active peptide. "Single" with respect to biologically active peptide is intended to mean that the polypeptide conjugate does not contain two or more different biologically active peptides which are attached respectively to the peptide linker. The single biologically active peptide, however, can include fragments or portions from different biologically active peptides fused together, for example, as a hybrid or chimera, as long as these portions are integrated as one peptide and are not respectively attached to the linker. If, however, two different biologically active peptides are attached respectively to the N-terminus and the C-terminus of the linker, then that is not a single biologically active peptide as used in the present disclosure.

The term "biologically active peptide" as used herein means a peptide having a biological function or activity, for example, a physiological function, or a therapeutic function. In certain embodiments, the biologically active peptide is therapeutically active. A peptide which, when stand alone, does not have biological function is not a biologically active peptide. For example, a peptide linker is not a biologically active peptide unless it has its own biological function or activity, for example when used alone.

The biologically active peptide comprises a Glucagon-like peptide-1 (GLP-1) receptor agonist.

The term "Glucagon-like peptide-1 (GLP-1) receptor" (also referred to as GLP1R) is a receptor protein found on beta cells on the pancreas and on neurons of the brain, comprising one extracellular domain and one transmembrane domain. The extracellular domain can bind to the C-terminal helix of GLP-1, and the transmembrane domain can bind to the N-terminal regions of GLP-1. The GLP-1 receptor is involved in the control of blood sugar level by enhancing insulin secretion. When expressed in the brain, the GLP-1 receptor can also be involved in the control of appetite.

The term "Glucagon-like peptide-1 (GLP-1) receptor agonist" or "GLP-1 receptor agonist" as used herein refers to a molecule which is capable of binding to and activating the GLP-1 receptor. A GLP-1 receptor agonist may elicit a magnitude of GLP-1 receptor response that is similar to or partial of a natural ligand.

The term "clearance-modifying moiety" or "CRM" as used herein refers to moiety that can alter one or more pharmacokinetic (PK) properties (for example, to increase the half-life in vivo). Examples of CRMs can include, without limitation, fatty acid, polyethylene glycol (PEG), glucuronic acid or other sugar based linkers, polar, positively or negatively charged groups that can increase the rates of hydrolysis of a succinimidyl ring and reduce or minimize the rate of reverse Michael reaction, therefore reduce or minimize the rate of loss of drug and the linker group from the biologically active peptide to other thiol-containing proteins and small molecules.

"CRM residue" as used herein refers to the amino acid residue that is conjugated to a CRM.

The term "conjugate" as used herein refers to a compound as a result of two or more molecules joined together to form one physical entity. For example, the conjugate of the present disclosure means a compound as a result of the polypeptide and one or more clearance-modifying moieties joined together. The molecules may attach together by covalent, non-covalent bonds, linkers, chemical modification, or protein fusion or by any means known to one skilled in the art. Preferably, the molecules may attach together by covalent bonds. The joining may be permanent or reversible. In some embodiments, certain cleavable or non-cleavable linkages may be included.

While conjugation of a CRM to a GLP-1 receptor agonist may extend half-life of the GLP-1 receptor agonist, it could also adversely affect the biological activity of the GLP-1 receptor agonist, rendering it less active than the unconjugated counterpart. For example, semaglutide, a conjugated GLP-1 derivative, has a significantly extended half-life, but suffers from a 939-fold loss in GLP-1 receptor binding in presence of human serum albumin (HSA) relative to its unconjugated counterpart (J. Med. Chem. 2015, 58, 7370-7380).

It is unexpectedly found by the inventors that, certain CRM-conjugated polypeptide comprising GLP-1 receptor agonist can have both an extended half-life and retained biological activity, if the CRM is conjugated outside of the GLP-1 receptor agonist on a peptide linker attached to its C-terminus. Interestingly, the distance between the C-terminus of the GLP-1 receptor agonist and the conjugation site has been found by the inventors to be of particular importance. If the CRM conjugation on the peptide linker is at a position close to the C-terminus of the GLP-1 receptor agonist, it would significantly reduce biological activity, which could be even much lower than conjugation on the GLP-1 receptor agonist itself. However, if the conjugation is at a position sufficiently farther away from the C-terminus of the GLP-1 receptor agonist, then the CRM-conjugated GLP-1 receptor agonist could have both extended half-life and retained biological activity. Such unexpected effects are found with certain GLP-1 receptor agonists and certain CRMs.

Herein, according to some embodiments of the polypeptide conjugate, the first CRM residue is at least 5 amino acid residues (exclusive of the CRM residue), e.g. 5, 6, 7, 8, 9, 10, 11, 12, 13, 14, 15, 16, 17, 18, 19, 20, 21, 22, 23, 24, 25, 26, 27, 28, 29, 30, 33, 35, 38, 40, 43, 45, 48, 50, 53, 55, 58, 60, 63, 65, 68, 70, 73, 75, or 78, etc. amino acid residues, away from the C-terminal amino acid residue of the biologically active peptide (e.g. the GLP-1 receptor agonist). In some embodiments of the polypeptide conjugate, the peptide linker can have a length of at least 10 amino acid residues, e.g. at least 12, 24, 32, 40, 48, 50, 60, 70, or 80 amino acid residues.

In certain embodiments, the first CRM residue is arranged in the peptide linker at a position close to the C-terminus of the peptide linker, which can be between 20 and 50 amino acid residues away from the C-terminal amino acid residue of the biologically active peptide (e.g. the GLP-1 receptor agonist). More details will be provided below.

According to some embodiments, the polypeptide conjugate is mono-conjugated, i.e., the first CRM is the only conjugate and the polypeptide conjugate is conjugated only at the first CRM residue (in the peptide linker) with the first CRM.

According to some other embodiments, the polypeptide conjugate is double-conjugated, i.e., the polypeptide conjugate is conjugated with two conjugates. One such conjugate is the first CRM, which is conjugated to the polypeptide conjugate at the first CRM residue (in the peptide linker). The other such conjugate is a second CRM, which is conjugated to the polypeptide conjugate at a second CRM residue, which is arranged in the biologically active peptide (i.e. GLP-1 receptor agonist such as GLP).

More details for the GLP-1 receptor agonist, the CRM and CRM residues, and polypeptide conjugates are provided below.

GLP-1 Receptor Agonist

In certain embodiments, the GLP-1 receptor agonist comprises GLP-1. The term "Glucagon-like peptide-1" or "GLP-1" as used herein is intended to broadly encompass native GLP-1 peptide and all its functional forms such as its functional variants, fragments, fusions, derivatives and mimetics.

The term "native GLP-1 peptide" as used herein refers to the native human Glucagon-Like Peptide-1 (GLP-1 (7-37)), the sequence of which is set forth in SEQ ID NO:1. As used herein, when referring to a particular amino acid residue in SEQ ID NO: 1 (i.e. GLP-1 (7-37)), the numbering of the GLP-1 (1-37) is followed. In other words, SEQ ID NO: 1 corresponds to GLP-1 (7-37), and therefore the $1^{st}$ residue (which is Histidine (H)) in SEQ ID NO: 1 is referred to as 7H, meaning that it corresponds to the $7^{th}$ residue in GLP (1-37); and the $31^{st}$ residue (which is Glycine (G)) in SEQ ID NO: 1 is referred to as 37G, meaning corresponds to the $37^{th}$ residue in GLP(1-37).

A functional form of the native GLP-1 peptide is capable of activating the GLP-1 receptor at a level comparable to, or no less than about 20% (or no less than 30%, 40%, 50%, 60%, 70%, 80%, 90%) of, that of the native GLP-1 peptide. Activation of the GLP-1 receptor typically initiates signal transduction pathway resulting in insulinotropic action or other physiological effects as is known in the art. Functional forms of the native GLP-1 peptide can contain one or more substitutions, additions, or deletions relative to SEQ ID NO: 1. Many functional forms of native GLP-1 peptide are known in the art, for example, without limitation, liraglutide, semaglutide, dulaglutide, albiglutide, and those disclosed in WO2000055203A1, WO 98/08871, WO 2006/097537, the disclosure of which is incorporated herein to its entirety.

In certain embodiments, the GLP-1 provided herein comprises an amino acid sequence having at least 70% (e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%) sequence identity to SEQ ID NO: 1 while retaining substantial biological activity of SEQ ID NO: 1.

In certain embodiments, the GLP-1 comprises no more than 9, 8, 7, 6, 5, 4, 3, or 2 mutations (e.g. addition, deletion, substitution) relative to SEQ ID NO: 1 while retaining substantial biological activity of SEQ ID NO: 1. In certain embodiments, the GLP-1 comprises at least 2, 3, 4, 5, 6, 7, 8, or 9 mutations (e.g. addition, deletion, substitution) relative to SEQ ID NO: 1 while retaining substantial biological activity of SEQ ID NO: 1.

One of ordinary skill in the art will appreciate that various amino acid substitutions, e.g., conservative amino acid substitutions, may be made in the sequence of any of the polypeptide fragment described herein, without necessarily decreasing its activity. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-national amino acids having an amino containing side chain, or substituting an alanine for norvaline or the like.

Various substitutions have been introduced to native GLP-1 peptide, and have been shown to be capable of retaining or even improving its biological activities. In some embodiments of the polypeptide conjugate provided herein, the GLP-1 comprises or consists of one or more mutations at a position selected from the group consisting of: A8, G22, K26, K34, and R36, or any combination thereof, relative to SEQ ID NO: 1. For example, it is believed that substitution at A8 is useful to prevent DPP4 enzymatic cleavage at the residue, substitution at G22 is desirable to improve activity and solubility, and substitution at R36 is useful to reduce immunogenicity. Examples of substitutions at these positions include, without limitation, A8G, A8Aib, A8T, G22E, K34R, R36G, as well as the substitutions described in U.S. Pat. No. 8,273,854, which are incorporated herein by its entirety.

In some embodiments of the polypeptide conjugate, the GLP-1 comprises or consists of one or more substitutions selected from the group consisting of: A8Aib, G22E, K26R, K34R and R36G, or any combination thereof.

In some embodiments of the polypeptide conjugate, the GLP-1 is a molecule which has substantially the biological activity of a wildtype human GLP-1 (SEQ ID NO: 1), and comprises a polypeptide fragment having an amino acid sequence of at least 50% (e.g. at least 60%, 65%, 70%, 75%, 80%, 85%, 90% or 95%) sequence identity to the wildtype human GLP-1.

In some embodiments, the GLP-1 comprises an amino acid sequence having at least 70% (e.g. at least 70%, 75%, 80%, 85%, 90% or 95%) sequence identity to SEQ ID NO: 1 while retaining substantial biological activity of SEQ ID NO: 1.

In some embodiments, the GLP-1 comprises an amino acid sequence of $X_7X_8EGTFTSDVSSYLEX_{22}X_{23}AAX_{26}X_{27}FIX_{30}WLVX_{34}GX_{36}G$ (SEQ ID NO: 2), where the $X_7$ is H, imidazole-4-acetate (IA), or imidazolepropionic acid (IPA); the $X_8$ is A, G, S, V, Aib, T, I, or L; the $X_{22}$ is G, or E; the $X_{23}$ is Q, C or K; the $X_{26}$ is K, R, or C; the $X_{27}$ is E, K, or C; the $X_{30}$ is A, C or K; the $X_{34}$ is R, K, or C; and the $X_{36}$ is R or G.

In some embodiments of the GLP-1, the $X_7$ is H; and $X_8$ is G or Aib.

In certain embodiments, the GLP-1 comprises an amino acid sequence selected from the group consisting of SEQ ID NOs: 1, and 3-9, which are listed in the following (genotypes are indicated following the Sequence Identification number):

SEQ ID NO: 1 (WT GLP-1)
SEQ ID NO: 3 (8Aib, 34R, 36G),
SEQ ID NO: 4 (8Aib, 26C, 34R, 36G),
SEQ ID NO: 5 (8Aib, 26R, 34R, 36G),
SEQ ID NO: 6 (8Aib, 22E, 34R, 36G),
SEQ ID NO: 7 (8Aib, 22E, 26C, 34R, 36G),
SEQ ID NO: 8 (8Aib, 22E, 26R, 34R, 36G),
SEQ ID NO: 9 (8G, 22E, 26R, 34R, 36G).

In certain embodiments, the GLP-1 receptor agonist in the polypeptide conjugate comprises or is GLP-1 as provided in the present disclosure. In some embodiments, the GLP-1 in the polypeptide conjugates provided herein comprises an amino acid sequence selected from the group consisting of: SEQ ID NOs: 3-9.

Peptide Linker

In the polypeptide conjugate disclosed herein, the biologically active peptide, i.e. GLP-1 receptor agonist (e.g. GLP-1), is attached to the N-terminus of the peptide linker.

Herein, the GLP-1 receptor agonist can optionally be attached to the peptide linker via a direct linkage (e.g., a covalent bond such as a peptide bond), and the peptide linker can optionally be made up of amino acid residues linked together by peptide bonds. Optionally, the peptide linker can further comprise one or more non-natural amino acids.

In some embodiments of the polypeptide conjugate, the peptide linker can have a length of at least 10 amino acid residues, e.g. at least 12, 24, 32, 40, 48, 50, 60, 70, or 80 amino acid residues.

Any suitable polypeptide linkers can be used. For example, the polypeptide linker may comprise or consist of amino acid residues selected from the amino acids glycine (G), serine (S), alanine (A), methionine (M), asparagine (N), glutamine (Q), cysteine (C) and lysine (K). In some embodiments, the polypeptide linker can be made up of a majority of amino acids that are sterically unhindered, such as glycine and alanine. In some embodiments, linkers are polyglycines, polyalanines, combinations of glycine and alanine (such as poly (Gly-Ala)), or combinations of glycine and serine (such as poly (Gly-Ser)).

In some embodiments, the peptide linker consists of amino acid residues selected from the group consisting of G, Q, A, E, P, S, and T, except for the first CRM residue.

In some embodiments, the peptide linker comprises a first sequence and a second sequence. The first sequence consists of one or more repeats of a repeating sequence, and is connected to N-terminus of the second sequence. The first CRM residue is in the second sequence, and can optionally be lysine residue or cysteine residue.

In certain embodiments, the repeating sequence comprises or consists of a sequence selected from the group consisting of: SEQ ID NOs: 10-40, and GS.

In some embodiments, the repeating sequence has a sequence of SEQ ID NO: 13 (GAQP).

Herein optionally, the number of the one or more repeats of the repeating sequence is an integer between 1 and 30. In certain embodiments, the number of the one or more repeats of the repeating sequence is selected from a group consisting of 5, 7, 9 and 11.

In certain embodiments, the second sequence of the peptide linker has a sequence of SEQ ID NO: 41 (GQKP) or SEQ ID NO: 42 (GQCP).

In certain embodiments, the polypeptide linker comprises an amino acid sequence selected from the group consisting of: SEQ ID NOS: 43-50, and 82-84.

It is noted that in addition to the above arrangement where the peptide linker comprises a first sequence and a second sequence, where the first sequence consists of one or more repeats of a repeating sequence, there can be other arrangements as well. In certain instances, the peptide linker may comprise or consist of more than one repeating sequence. For example, the polypeptide linker comprises or consists of 2, 3, or 4 different repeating sequences. In certain embodiments, the polypeptide linker comprises or consists of sequential or tandem repeats of the different repeating sequences.

CRM Residue

Without wishing to be bound by any theory, it is believed that CRM (or fatty acid) conjugation to GLP-1 can reduce its activity in the presence of HSA. For example, the reduction in GLP-1 activity has been reported for semaglutide, which has a fatty acid conjugated to K26 of GLP-1 (8Aib, 36R) and showed significant reduction in activity compared to its non-conjugated counterpart in the presence of HSA. Since HSA is present in human blood and is unavoidable under physiological conditions, reduction in GLP-1 receptor agonist activity in the presence of HSA is believed to compromise therapeutic activity of the protein conjugates. However, some of the polypeptide conjugates provided herein can retain most of the GLP-1 activity in the presence of HSA despite of CRM conjugation. In such embodiments, the polypeptide conjugates provided herein is mono-conjugated, and has the CRM conjugated to the peptide linker but not to the biologically active peptide (e.g. GLP-1).

In some of these embodiments, such mono-conjugated polypeptide conjugates provided herein has increased GLP-1 receptor agonist activity in the presence of human serum albumin (HSA), compared to a comparative polypeptide conjugate without the peptide linker and having a CRM conjugated on the GLP-1. In certain embodiments, the GLP-1 receptor agonist activity in the presence of HSA can be determined in an in vitro assay for GLP-1 receptor activation, either in a cell free assay such as cAMP assay or in a cell-based assay such as reporter cell assay, as known in the art. In certain embodiments, the comparative polypeptide conjugate is semaglutide. In certain embodiments, the mono-conjugated polypeptide conjugates provided herein activates GLP-1 receptor in the presence of human serum albumin (HSA) at an EC50 no more than 50% (or no more than 40%, 30%, 20%, 10%, 5%, or 3%) than that of semaglutide in the presence of HSA, as determined in the same or comparable assay. In certain embodiments, the mono-conjugated polypeptide conjugates provided herein activates GLP-1 receptor in the absence of HSA at an EC50 comparable to (e.g. from 20% to 300% of) that of semaglutide in the absence of HSA, as determined in the same or comparable assay. In certain embodiments, the amount of human serum albumin (HSA) allows assessment of impact of HSA binding to the GLP-1 receptor activation. In certain embodiments, the in vitro assay for GLP-1 receptor activation is conducted in the presence of at least 0.5%, 1%, 1.2%, 1.5%, 1.8% or 2% HSA.

In certain embodiments, the mono-conjugated polypeptide conjugates provided herein binds to HSA at a binding affinity (KD) comparable to (e.g. from about 70% to about 500% of) that of semaglutide, as determined in the same or comparable assay.

In certain embodiments, the mono-conjugated polypeptide conjugates provided herein has at least comparable terminal half life compared to a comparative polypeptide conjugate without the peptide linker and having a CRM conjugated on the GLP-1, such as semaglutide, as determined under comparable in vivo study conditions and in the same type of experimental animals. Suitable animals for terminal half life determination include for example mice, rats, minipigs, or monkeys. In certain embodiments, the terminal half-life is determined in a suitable animal after a single dose intravenous administration or subcutaneous administration or oral administration at a dose suitable for providing therapeutic efficacy.

In certain embodiments, the polypeptide conjugates further comprise a second CRM conjugated to a second CRM residue. In other words, the present disclosure also provides double-conjugated polypeptide conjugate. It is unexpectedly found by the inventors that a second CRM conjugation can further extend the half-life of the polypeptide conjugate. In certain embodiments, the double-conjugated polypeptide conjugate having both the first and the second CRM conjugations can have an extended half-life that is at least 1-fold, 2-fold, 3-fold, 4-fold, 5-fold, 6-fold or even longer than a corresponding polypeptide conjugate (e.g. semaglutide) having only one CRM conjugation.

The second CRM residue can be at any suitable position. In certain embodiments, the second CRM residue is in the GLP-1 receptor agonist or in the peptide linker.

In certain embodiments, the second CRM residue is at K26 of the GLP-1 peptide. It has been reported that conjugation with two fatty acid moieties on a GLP-1 peptide can significantly reduce the activity or even render the conjugated GLP-1 peptide ineffective. It is therefore unexpectedly found by the present inventors that, conjugation both on GLP-1 (e.g. K26) and on the peptide linker at a position sufficiently away from the C-terminus of the GLP-1 peptide, can minimize the negative impact of fatty acid conjugation to the biological activity of GLP-1 polypeptide in the presence of HSA.

In some of these embodiments, such double-conjugated polypeptide conjugates provided herein has a comparable or acceptable GLP-1 receptor agonist activity in the presence of HSA, compared to a comparative polypeptide conjugate without the peptide linker and having a CRM conjugated on the GLP-1. In certain embodiments, the double-conjugated polypeptide conjugates provided herein activates GLP-1 receptor in the presence of HSA at an EC50 of no more than 2000% (or no more than 1500%, 1000%, 900%, 800%, 700%, 600%, or 500%) than that of a comparative polypeptide conjugate without the peptide linker and having a CRM conjugated on the GLP-1, such as semaglutide in the presence of HSA, as determined in the same or comparable assay. In certain embodiments, the double-conjugated polypeptide conjugates provided herein activates GLP-1 receptor in the absence of HSA at an EC50 comparable to (e.g. no more than 500%, 400%, 300%, or 200% of, or even less than) that of a comparative polypeptide conjugate without the peptide linker and having a CRM conjugated on the GLP-1, such as semaglutide, as determined in the same or comparable assay. In certain embodiments, the double-conjugated polypeptide conjugates provided herein activates GLP-1 receptor at a first EC50 in the presence HSA, and at a second EC50 in the absence of HSA, and the first EC50 is higher than the second EC50 but is no more than 1000-fold of that of the second EC50, for example, the first EC50 (in the presence of HSA) is no more than 900-fold, 800-fold, 700-fold, 600-fold, or 500-fold of the second EC50 (in the absence of HSA). In certain embodiments, HSA is present in the in vitro assay for GLP-1 receptor activation at a suitable amount that allows assessment of impact of HSA binding to the GLP-1 receptor activation. In certain embodiments, the in vitro assay for GLP-1 receptor activation is conducted in the presence of a suitable amount of human serum albumin (HSA) that allows assessment of impact of HSA binding to the GLP-1 receptor activation. In certain embodiments, the in vitro assay for GLP-1 receptor activation is conducted in the presence of at least 0.5%, 1%, 1.2%, 1.5%, 1.8% or 2% HSA.

In certain embodiments, the double-conjugated polypeptide conjugates provided herein binds to HSA at a higher binding affinity, represented by a KD value significantly lower than (e.g. no more than 50%, 40%, 30%, or 20% of) that of a comparative polypeptide conjugate without the peptide linker and having a CRM conjugated on the GLP-1, such as semaglutide, as determined in the same or comparable assay.

In certain embodiments, double-conjugated polypeptide conjugates provided herein has enhanced pharmacokinetic properties in comparison to a comparative polypeptide conjugate without the peptide linker and having a CRM conjugated on the biologically active peptide (e.g. GLP-1), wherein the pharmacokinetic properties are determined by measuring blood concentration of the polypeptide conjugate after administration of a therapeutically effective dose to a subject.

In certain embodiments, the double-conjugated polypeptide conjugates provided herein has an increase in terminal half-life by at least 50%, 60%, 70%, 80%, 90%, 100%, 120%, 150%, 180%, 200%, 300%, or 400% than that of a comparative polypeptide conjugate without the peptide linker and having a CRM conjugated on the GLP-1, such as semaglutide, as determined under comparable in vivo study conditions and in the same type of experimental animals. Suitable animals for terminal half life determination include for example mice, rats, minipigs, or monkeys. In certain embodiments, the terminal half-life is determined in a suitable animal after a single dose intravenous administration or subcutaneous administration at a dose suitable for providing therapeutic efficacy.

In certain embodiments, the double-conjugated polypeptide conjugates provided herein has blood or plasma or serum concentrations that remain within therapeutic window for the polypeptide conjugate for a period at least about 50% longer (60%, 70%, 80%, 90%, 100%, 120%, 150%, 180%, 200%, 300%, or 400% longer) that of a comparative polypeptide conjugate without the peptide linker and having a CRM conjugated on the GLP-1, such as semaglutide, as determined under comparable in vivo study conditions and in the same type of experimental animals. The term "therapeutic window" as used herein means that the range of concentration level of the polypeptide conjugates in the blood or plasma or serum that provides for therapeutic benefit or efficacy for the condition to be treated without unacceptable toxicity. The range of concentration level can be from the minimal concentration that results in a therapeutic response to the maximal concentration that provides for therapeutic response yet without inducing unacceptable toxicity.

In certain embodiments, the double-conjugated polypeptide conjugates provided herein provides for an extended duration of therapeutic efficacy in comparison with a comparative polypeptide conjugate without the peptide linker and having a CRM conjugated on the GLP-1, such as semaglutide, as determined under comparable in vivo study conditions and in the same type of experimental animals. Such an extended therapeutic efficacy can be characterized by area under curve (AUC) for time-response curve, which can be plotted after a single dose or after repeated doses that are suitable for providing an intended therapeutic effect in a subject having a metabolic condition (e.g. a disease model animal). The extended therapeutic efficacy duration can also be characterized by the duration of the therapeutic response.

In certain embodiments, the therapeutic response comprises reduction in body weight, reduction in food intake, or reduction in glucose level (fasting glucose level or non-fasting glucose level). In certain embodiments, the double-conjugated polypeptide conjugates provided herein has an increase in the AUC for the time-response curve by at least 50%, 60%, 70%, 80%, 90%, 100%, 120%, 150%, 180%, 200% than that of a comparative polypeptide conjugate without the peptide linker and having a CRM conjugated on the GLP-1, such as semaglutide, as determined under comparable in vivo study conditions and in the same type of experimental animals. In certain embodiments, the double-conjugated polypeptide conjugates provided herein has an increase in duration of the therapeutic response by at least 50%, 60%, 70%, 80%, 90%, 100%, 120%, 150%, 180%, 200%, 300%, or 400% than that of a comparative polypeptide conjugate without the peptide linker and having a CRM conjugated on the GLP-1, such as semaglutide, as determined under comparable in vivo study conditions and in the same type of experimental animals. In certain embodiments, the experimental animals for therapeutic response are disease model animals such as db/db mice, or diet-induced obese (DIO) animals.

CRM Residue

Within the scope of the present disclosure provided herein, different CRM residues may be used in the polypeptide conjugate depending on the different CRM used, and there can be one or two CRM residues in the polypeptide conjugate that mediate(s) the conjugation of the CRM to the polypeptide conjugate.

In certain embodiments, the polypeptide conjugate can be mono-conjugated with a CRM.

In certain embodiments, the peptide linker-residing first CRM residue is lysine residue, and the polypeptide conjugate comprises only one lysine residue. In such embodiments, the peptide linker comprises only one lysine residue, and the GLP-1 receptor agonist comprises no lysine residue, and in accordance, the naturally occurring residue found in the native GLP-1 (1-37) sequence, namely K26 and K34, can optionally be substituted to non-lysine residues (e.g. R, Q, A, G, H, S, and T, etc.). In certain embodiments, the GLP-1 comprises substitutions of K26R and K34R.

It is noted that throughout the specification, when the CRM residue (e.g. K or C) is present in GLP-1, the position of the CRM residue is identified in reference to the amino acid sequence of GLP-1 (1-37). For example, K26 indicates that the $26^{th}$ position in reference to the amino acid sequence of GLP-1 (1-37) (which corresponds to the $20^{th}$position in reference to the amino acid sequence of GLP-1 (7-37), i.e. SEQ ID NO: 1) is K. Similarly, K34 indicates that the $34^{th}$ position in reference to the amino acid sequence of GLP-1 (1-37) (which corresponds to the $28^{th}$ position in reference to the amino acid sequence of GLP-1 (7-37), i.e. SEQ ID NO: 1) is K.

In certain embodiments, the peptide linker-residing first CRM residue is cysteine residue, and the polypeptide conjugate comprises only one cysteine residue. In such embodiments, the peptide linker comprises only one cysteine residue, and the GLP-1 receptor agonist comprises no cysteine residue. In certain embodiments, the single biologically active peptide polypeptide in the polypeptide conjugate comprises GLP-1. Native GLP-1 does not contain any cysteine residue, and therefore any GLP-1 derivative (including those provided herein) may be used as long as it does not contain a cysteine residue.

In certain embodiments, the first CRM residue is a non-natural amino acid residue, and the polypeptide conjugate comprises only one non-natural amino acid residue as the CRM residue. Non-natural amino acid can contain a variety of functional groups or reactive groups, which can provide for additional functions and/or reactivity. Particular non-natural amino acids that are beneficial for purpose of conjugating moieties to the fusion polypeptides of the present disclosure include those with a side chain having azide, alkyne, alkene, cycloalkyne or halide.

In the mono-conjugated polypeptide conjugate, when the peptide linker-residing first CRM residue is lysine residue, the GLP-1 can comprise an amino acid sequence of SEQ ID NO: 5 or SEQ ID NO: 8. Herein, the peptide linker can optionally comprise an amino acid sequence selected from the group consisting of: SEQ ID NO: 43, SEQ ID NO: 45, and SEQ ID NO: 46. In certain embodiments, the polypeptide conjugate comprises an amino acid sequence selected from the group consisting of SEQ ID NOs: 52, 55, 56, and 60-62, which are listed in the following (the first CRM residues are indicated following the Sequence Identification number):

SEQ ID NO: 52 (76K),
SEQ ID NO: 55 (68K),
SEQ ID NO: 56 (60K),
SEQ ID NO: 60 (76K),
SEQ ID NO: 61 (68K), or
SEQ ID NO: 62 (60K).

In the mono-conjugated polypeptide conjugate, when the peptide linker-residing first CRM residue is cysteine residue, the GLP-1 can comprise an amino acid sequence selected from the group consisting of: SEQ ID NOs: 3, 5, 6, and 9. Herein, the peptide linker can optionally comprise an amino acid sequence selected from the group consisting of: SEQ ID NO: 47, SEQ ID NO: 49, and SEQ ID NO: 50. In certain embodiments, the polypeptide conjugate comprises an amino acid sequence selected from the group consisting of SEQ ID NOs: 66-71, and 75-80, which are listed in the following (the first CRM residues are indicated following the Sequence Identification number):

SEQ ID NO: 66 (76C),
SEQ ID NO: 67 (68C),
SEQ ID NO: 68 (60C),
SEQ ID NO: 69 (76C),
SEQ ID NO: 70 (68C),
SEQ ID NO: 71 (60C),
SEQ ID NO: 75 (76C),
SEQ ID NO: 76 (68C),
SEQ ID NO: 77 (60C),
SEQ ID NO: 78 (76C),
SEQ ID NO: 79 (68C),
SEQ ID NO: 80 (60C).

In certain embodiments, the polypeptide conjugate further comprises a second CRM residue, i.e. the polypeptide conjugate is double-conjugated, having two CRMs (i.e. the first CRM and the second CRM) respectively conjugated at the two CRM residues (i.e. the first CRM residue and second CRM residue).

In certain embodiments, the second CRM residue is in the peptide linker, just like the first CRM residue. In such embodiments, the second CRM residues can be at any suitable distance from the first CRM residue, as long as both CRM residues can be properly conjugated.

In certain embodiments, the second CRM residue is in the GLP-1 receptor agonist, for example, GLP-1. In certain embodiments, the second CRM residue is a naturally occurring residue found in the native GLP-1 sequence, or an introduced residue, for example, by substitution of a naturally occurring residue, or by insertion of a new residue.

In certain embodiments, the first and the second CRM residues are both lysine residues, and the polypeptide conjugate comprises only two lysine residues. In certain embodiments, the second lysine residue is in the GLP-1, and is selected from the group consisting of K23, K26, K27, K30, and K34. In certain embodiments, the second CRM residue is a naturally occurring residue found in the native GLP-1 sequence, for example, K26 or K34. In certain embodiments, the second CRM residue is an introduced residue. The CRM residue can be introduced into GLP-1 sequence at any suitable position, for example by substitution, as long as such substitution does not substantially diminish the GLP-1R agonist activity of the GLP-1. The second CRM residue can be introduced, for example, by substitution of Q23K, E27K, or A30K. In certain embodiments, all lysine residue(s) other than the CRM residue(s) in the GLP-1 are substituted to a non-lysine residue, so that the polypeptide conjugate comprises no additional lysine residue except for the CRM residues. For example, if K26 is the second CRM residue, then K34 is substituted to a non-lysine residue, or vice versa. Non-lysine residue can be selected by a skilled person in the art, and examples include Arginine (R), Glutamine (Q), Alanine (A), Glycine (G), Histidine (H), Serine (S), or Threonine (T).

In the double-conjugated polypeptide conjugate, when both the first and the second CRM residues are lysine residue, the GLP-1 can comprise an amino acid sequence of SEQ ID NO: 3 or SEQ ID NO: 6. Herein, the peptide linker can optionally comprise an amino acid sequence selected from the group consisting of: SEQ ID NOS: 43-45, or 83. In certain embodiments, the polypeptide conjugate comprises an amino acid sequence selected from the group consisting of SEQ ID NOs: 51, 53, 54, 57-59, 85 and 86, which are listed in the following (the first and second CRM residues are indicated following the Sequence Identification number):

SEQ ID NO: 51 (26K, 76K),
SEQ ID NO: 53 (26K, 84K),
SEQ ID NO: 54 (26K, 68K),
SEQ ID NO: 57 (26K, 76K),
SEQ ID NO: 58 (26K, 84K),
SEQ ID NO: 59 (26K, 68K),
SEQ ID NO: 85 (26K, 96K) or
SEQ ID NO: 86 (26K, 60K).

In certain embodiments, the first and the second CRM residues are both cysteine residues, and the polypeptide conjugate comprises only two cysteine residues. In certain embodiments, the second cysteine residue is in the GLP-1. In certain embodiments, the second cysteine residue is in the peptide linker.

In certain embodiments, the first and the second CRM residues are both non-natural amino acid residues, and the polypeptide conjugate comprises only two non-natural amino acid residues as the CRM residues.

In certain embodiments, the cysteine residue or the non-natural amino acid residue in the GLP-1 is introduced by a substitution at the position selected from the group consisting of: Q23, K26, E27, A30, and K34, relative to SEQ ID NO: 1. In certain embodiments, the cysteine residue or the NNAA in the GLP-1 is introduced by a substitution at the position of K26 or E27, relative to SEQ ID NO: 1. In certain embodiments, the second CRM residue in the GLP-1 is cysteine and is introduced by a substitution at a position selected from the group consisting of: Q23C, K26C, E27C, A30C and K34C.

In the double-conjugated polypeptide conjugate, when both the first and the second CRM residues are cysteine residue, the GLP-1 can comprise an amino acid sequence of SEQ ID NO: 4 or SEQ ID NO: 7. Herein, the peptide linker can optionally comprise an amino acid sequence selected from the group consisting of: SEQ ID NOS: 47-49. In certain embodiments, the polypeptide conjugate comprises an amino acid sequence selected from the group consisting of SEQ ID NOs: 63-65 and 72-74, which are listed in the following (the first and second CRM residues are indicated following the Sequence Identification number):

SEQ ID NO: 63 (26C, 84C),
SEQ ID NO: 64 (26C, 76C),
SEQ ID NO: 65 (26C, 68C),
SEQ ID NO: 72 (26C, 84C),
SEQ ID NO: 73 (26C, 76C),
SEQ ID NO: 74 (26C, 68C).

CRM

In certain embodiments, each of the first CRM and/or the second CRM (or generally CRM) comprises a plasma protein-binding moiety, a polymer, Fc, human serum albumin (HSA) and functional fragments thereof, Xten sequence, or PAS sequence. In certain embodiments, the Xten sequence is an extended recombinant polypeptide sequence with an amino acid sequence described in WO2007103515, WO2009023270, WO2010091122, WO2011123813, WO2013130683, WO2017146979, WO2011084808, WO2013040093, WO2013122617, WO2014011819, WO2013184216, WO2014164568, WO2015023891, WO2016077505 and WO2017040344, disclosures of which have been incorporated by their entirety. In certain embodiments, the term "PAS", which can also be used interchangeable with the term "APS", refers to an amino acid repeats consisting of Ala, Ser, and Pro residues, as described in U.S. Pat. No. 8,563,521 B2, disclosure of which has been incorporated by its entirety.

In certain embodiments, the CRM comprises an albumin-binding moiety. The term "albumin-binding moiety" refers to any functional moiety that is capable of binding albumin (e.g. human serum albumin) or any functional fragment thereof with sufficient specificity, preferably non-covalently. The albumin-binding moiety attached to a therapeutic fusion polypeptide, polypeptide, or polypeptide complex typically has an affinity below 10 M to human serum albumin and preferably below 1 pM. The albumin-binding moiety can include, without limitation, an albumin-binding domain, an albumin-binding sequences from synthetic peptides, and an albumin-binding chemical moiety. For example, the albumin-binding moiety is selected from an albumin-binding domain from streptococcal protein G, an albumin-binding domain from *Peptostreptococcus magnus* protein PAB, an albumin-binding peptide having the core sequence DICLPRWGCLW (SEQ ID NO: 81). A number of small peptides which are albumin binding moieties have been described in J. Biol Chem. 277, 38 (2002) 35035-35043. For another example, the albumin-binding moiety is selected from linear and branched lipohophillic moieties containing 4-40 carbon atoms, compounds with a cyclopentanophenanthrene skeleton etc. For example, the albumin-binding moiety is a group of the formula $CH_3(CH_2)_vCO—NHCH(COOH)(CH_2)_2CO—$, wherein v is an integer of from 10 to 24.

In certain embodiments, the albumin-binding moiety comprises a structure of: *-A-B-C-D-E, wherein A, B, C, D and E are interconnected via amide bonds, and the * end of A is connected to a reactive group of the conjugatable residue on the polypeptide complex, and wherein:

A is selected from a bond,

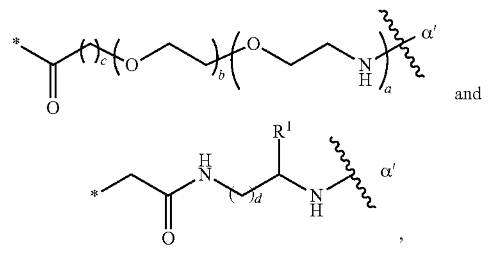

and

, where a, b, c and d are independently an integer from 0 to 4, $R^1$ is hydrogen or —COOH; B is selected from a bond,

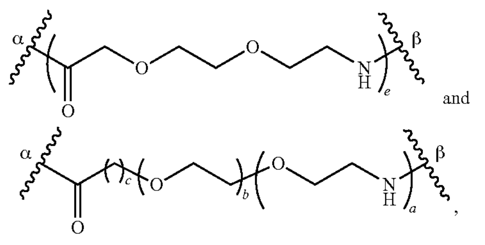

where e is an integer from 1 to 4, wherein position α is linked to position α';

C is a bond or

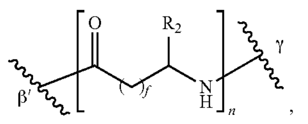

where $R^2$ is —$CH_2SO_3H$ or —COOH, f is an integer from 1 to 4, n is an integer from 1 to 25, wherein when B is not bond, then position β' is linked to position β, or when B is bond, then position β' is linked to position α';

D is selected from a bond,

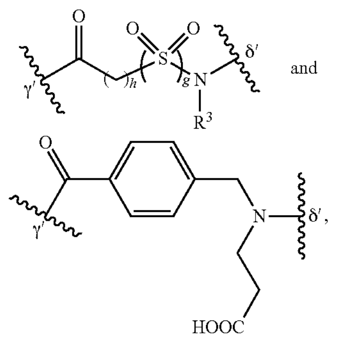

where g and h are independently 0 or 1, and $R^3$ is H or —$CH_2COOH$, wherein:

when B is not a bond and C is a bond, then position γ' is linked to position β;

when C is not a bond, then position γ' is linked to position γ; and when B is a bond and C is a bond, then position γ' is linked to position α';

E is an acidic group having a formula:

(I)

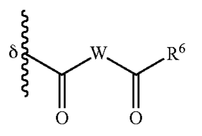

wherein W represents —$(CR^4R^5)_I$—, where $R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide, $R^6$ is selected from hydroxyl or $NR^7R^8$, where $R^7$ and $R^8$ are independently selected from the group consisting of hydrogen, alkyl, hydroxyl, and

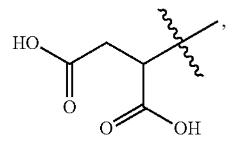 [SMILES: *C(CC(=O)O)C(=O)O]

and I is an integer from 10 to 20, and wherein:

when D is not a bond, then position δ is linked to position δ', when C is not a bond and D is a bond, then position δ is linked to position γ, when B is not a bond, C is a bond and D is a bond, then position δ is linked to position β, when A is not a bond, and all of B, C, and D are bond, then position δ is linked to position α'.

In certain embodiments,

A is a bond or

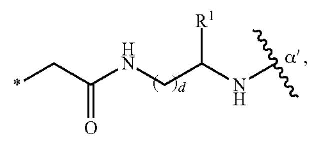

where d is an integer from 1 to 4, $R^1$ is hydrogen;

B is a bond or

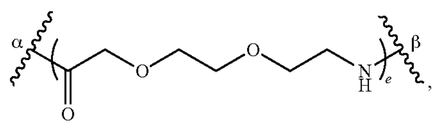

where e is an integer from 1 to 4, wherein position α is linked to position α';

C is

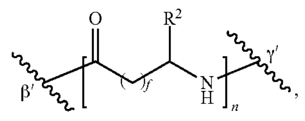

where $R^2$ is —COOH, f is an integer from 1 to 4, and n is an integer from 1 to 25, wherein: when B is not bond, then position β' is linked to position β, or when B is bond, then position β' is linked to position α';

D is a bond;

regarding E, each of $R^4$ and $R^5$ is hydrogen, $R^6$ is hydroxyl, I is an integer from 10 to 20, and position δ is linked to position γ.

Further optionally, d is 1, e is 2, f is 1, n is 1, and I is an integer from 14 to 20.

In certain embodiments, the CRM is conjugated to a lysine residue, optionally the lysine residue is in the peptide linker or in the GLP-1. Herein, A can be a bond and B can be

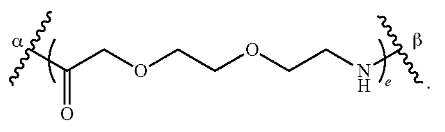

In such embodiments, the CRM comprises the structure of below formula (also referred to as —HOOC-(CH2)16-CO-gGlu-2XADO, where 2XADO means two consecutive ADO moieties, and ADO is short for 8-amino-3,6-dioxaoctanoic acid):

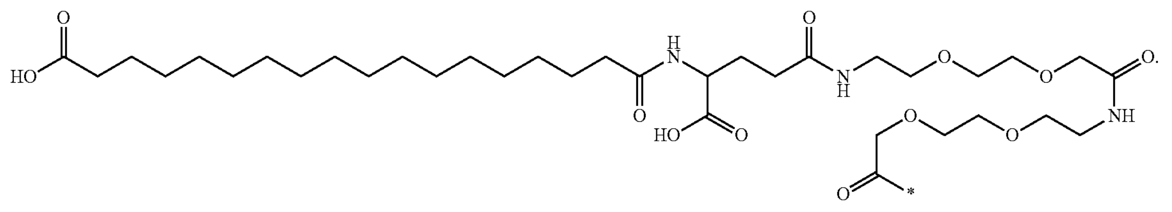 [SMILES: *C(=O)COCCOCCNC(=O)COCCOCCNC(=O)CCC(NC(=O)CCCCCCCCCCCCCCCCC(=O)O)C(=O)O]

In certain embodiments, the CRM is conjugated to a cysteine residue, optionally the cysteine residue is in the peptide linker or in the GLP-1. Herein, A can be

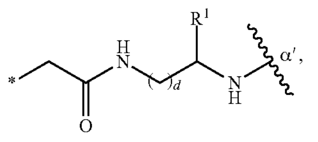

and B can be

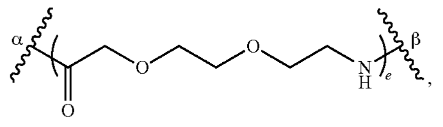

wherein position α is linked to position α'.

In such embodiments, the CRM comprises the structure of below formula (also referred to as HOOC-(CH2)16-CO-gGlu-2XADO-EDA-CO-CH2) or HOOC-(CH2)20-CO-gGlu-2XADO-EDA-CO-CH2):

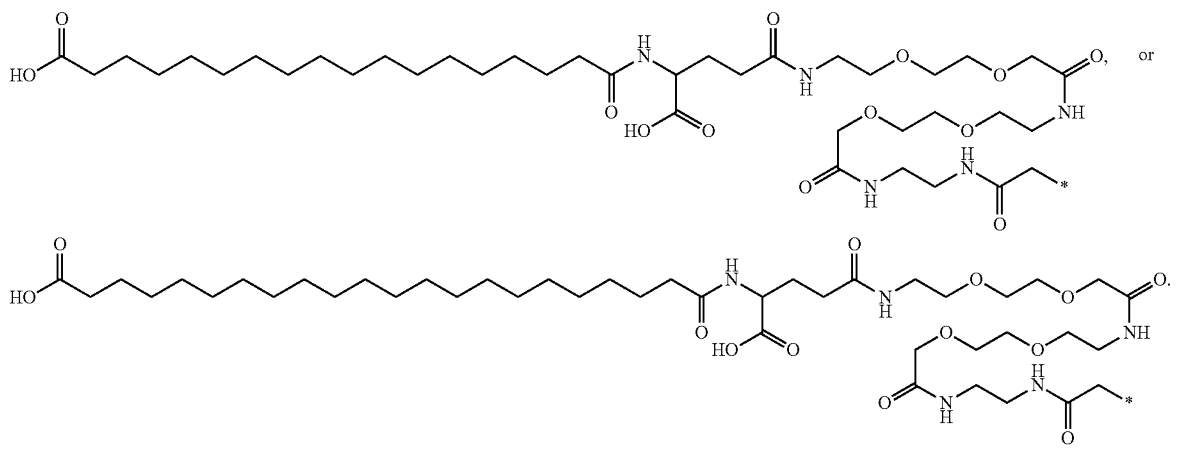

Further according to some embodiments, the CRM comprises the structure of below formula (also referred to as HOOC-(CH2)16-CO-gGlu-2XADO-EDA-CO-CH2):

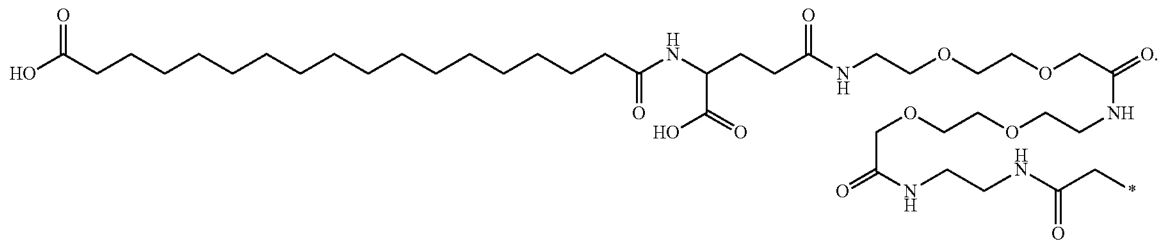 [SMILES: *CC(=O)NCCNC(=O)COCCOCCNC(=O)COCCOCCNC(=O)CCC(NC(=O)CCCCCCCCCCCCCCCCC(=O)O)C(=O)O]

Polypeptide Conjugates

In certain embodiments, the polypeptide conjugate provided herein comprises or consists of an amino acid sequence selected from the group consisting of SEQ ID NOs: 51-80, and 85-88.

In certain embodiments, the polypeptide conjugate provided herein is mono-conjugated, i.e. a single CRM is conjugated at a single CRM residue in the polypeptide portion of the polypeptide conjugate. Herein, the GLP-1 comprises an amino acid sequence selected from the group consisting of: SEQ ID NOS: 3, 5, 6, 8, and 9. Herein, the polypeptide portion of the polypeptide conjugate can comprise or consist of an amino acid sequence selected from the group consisting of SEQ ID NOs: 52, 55, 56, 60-62, 66-71, and 75-80, the CRM residue can be lysine residue or cysteine residue in the peptide linker of the polypeptide portion at a position selected from a group consisting of 60, 68, and 76, and the CRM can comprise the structure of Moiety A (HOOC-(CH2)16-CO-gGlu-2XADO) for lysine conjugation, or of Moiety B (HOOC-(CH2)16-CO-gGlu-2XADO-EDA-CO-CH2) for cysteine conjugation.

In the mono-conjugated polypeptide conjugate where the CRM residue is lysine residue, the various embodiments of the polypeptide conjugate are listed below, each indicated for the amino acid sequence for the polypeptide portion and the position for the CRM residue: SEQ ID NO: 52 (76K); SEQ ID NO: 55 (68K); SEQ ID NO: 56 (60K); SEQ ID NO: 60 (76K); SEQ ID NO: 61 (68K); and SEQ ID NO: 62 (60K). In certain embodiments, the polypeptide conjugate comprises the polypeptide portion comprising or consisting of an amino acid sequence of SEQ ID NO: 52, and the first CRM residue is 76K. In certain embodiments, the polypeptide conjugate comprises the polypeptide portion comprising or consisting of an amino acid sequence of SEQ ID NO: 60, and the first CRM residue is 76K. Each polypeptide conjugate has Moiety A (HOOC-(CH2)16-CO-gGlu-2XADO) as the CRM.

In the mono-conjugated polypeptide conjugate where the CRM residue is cysteine residue, the various embodiments of the polypeptide conjugate are listed below, each indicated for the amino acid sequence for the polypeptide portion and the position for the CRM residue: SEQ ID NO: 66 (76C); SEQ ID NO: 67 (68C); SEQ ID NO: 68 (60C); SEQ ID NO: 69 (76C); SEQ ID NO: 70 (68C); SEQ ID NO: 71 (60C); SEQ ID NO: 75 (76C); SEQ ID NO: 76 (68C); SEQ ID NO: 77 (60C); SEQ ID NO: 78 (76C); SEQ ID NO: 79 (68C); and SEQ ID NO: 80 (60C). In certain embodiments, the polypeptide conjugate comprises the polypeptide portion comprising or consisting of an amino acid sequence of SEQ ID NO: 57, and is conjugated with the first CRM and the second CRM respectively at 26K and 76K. Each polypeptide conjugate has Moiety B (HOOC-(CH2)16-CO-gGlu-2XADO-EDA-CO-CH2) as the CRM.

In certain embodiments, the polypeptide conjugate provided herein is double-conjugated, i.e. two CRMs are respectively conjugated at two CRM residues, one in the GLP-1 and another in the peptide linker, of the polypeptide portion of the polypeptide conjugate. Herein, the GLP-1 comprises an amino acid sequence selected from the group consisting of: SEQ ID NOS: 3, 4, 6, and 7.

Herein, the polypeptide portion of the polypeptide conjugate can comprise or consist of an amino acid sequence selected from the group consisting of SEQ ID NOs: 51, 53, 54, 57-59 and 63-65, 72-74, 85, and 86. The two CRM residues can be lysine residues or cysteine residues, with one at position 26, and another at a position selected from a group consisting of 68, 76, and 84. The two CRMs are identical, comprising the structure of Moiety A (HOOC-(CH2)16-CO-gGlu-2XADO) for lysine conjugation, or of Moiety B (HOOC-(CH2)16-CO-gGlu-2XADO-EDA-CO-CH2) for cysteine conjugation.

In the double-conjugated polypeptide conjugate where the two CRM residues are both lysine residues, the various embodiments of the polypeptide conjugate are listed below, each indicated for the amino acid sequence for the polypeptide portion and the position for the two CRM residues: SEQ ID NO: 51 (26K, 76K); SEQ ID NO: 53 (26K, 84K); SEQ ID NO: 54 (26K, 68K); SEQ ID NO: 57 (26K, 76K); SEQ ID NO: 58 (26K, 84K); SEQ ID NO: 59 (26K, 68K); SEQ ID NO: 85 (26K, 96K); and SEQ ID NO: 86 (26K, 60K). Each polypeptide conjugate has Moiety A (HOOC-(CH2)16-CO-gGlu-2XADO) as the two CRMs.

In the double-conjugated polypeptide conjugate where the two CRM residues are both cysteine residues, the various embodiments of the polypeptide conjugate are listed below, each indicated for the amino acid sequence for the polypeptide portion and the position for the two CRM residues: SEQ ID NO: 63 (26C, 84C); SEQ ID NO: 64 (26C, 76C); SEQ ID NO: 65 (26C, 68C); SEQ ID NO: 72 (26C, 84C); SEQ ID NO: 73 (26C, 76C); and SEQ ID NO: 74 (26C, 68C). Each polypeptide conjugate has Moiety B (HOOC-(CH2)16-CO-gGlu-2XADO-EDA-CO-CH2) as the two CRMs.

In certain embodiments, the CRM is conjugated to a non-natural amino acid residue in the fusion polypeptide. In certain embodiments, the CRM is conjugated to a non-natural amino acid residue in the polypeptide.

Table 1 below shows the detailed information of certain exemplary polypeptide conjugates, including SEQ ID NOs of the polypeptide portion, the GLP-1, and the peptide linker, and the CRM residue. Mutations in the GLP-1, as well as the repeating sequences and number of repeats in the peptide linker sequences are also shown.

TABLE 1

Exemplary polypeptide conjugate sequences

| Molecule Code (MLC) | Mutations in GLP-1** (SEQ ID NO of the GLP-1) | Repeating sequences & No. of repeats (SEQ ID NO of the peptide linker) | CRM residue(s)# (SEQ ID NO of the polypeptide portion) | CRM |
|---|---|---|---|---|
| 002 | 8Aib,26R, 34R,36G (SEQ ID NO: 5) | (GAQP)9(GQKP) (SEQ ID NO: 43) | 76K (SEQ ID NO: 52) | Moiety A& |
| 009 | 8Aib,26R,34R,36G (SEQ ID NO: 5) | (GAQP)7(GQKP) (SEQ ID NO: 45) | 68K (SEQ ID NO: 55) | Moiety A& |
| 010 | 8Aib,26R,34R,36G (SEQ ID NO: 5) | (GAQP)5(GQKP) (SEQ ID NO: 46) | 60K (SEQ ID NO: 56) | Moiety A& |

TABLE 1-continued

| Exemplary polypeptide conjugate sequences | | | | |
|---|---|---|---|---|
| Molecule Code (MLC) | Mutations in GLP-1** (SEQ ID NO of the GLP-1) | Repeating sequences & No. of repeats (SEQ ID NO of the peptide linker) | CRM residue(s)# (SEQ ID NO of the polypeptide portion) | CRM |
| 011 | 8Aib,26R,34R,36G (SEQ ID NO: 5) | (GAQP)2(GQKP) (SEQ ID NO: 84) | 48K (SEQ ID NO: 88) | Moiety A& |
| 019 | 8Aib,22E,26R 34R,36G (SEQ ID NO: 8) | (GAQP)9(GQKP) (SEQ ID NO: 43) | 76K (SEQ ID NO: 60) | Moiety A& |
| 020 | 8Aib,22E,26R,34R,36G (SEQ ID NO: 8) | (GAQP)7(GQKP) (SEQ ID NO: 45) | 68K (SEQ ID NO: 61) | Moiety A& |
| 021 | 8Aib,22E,26R,34R,36G (SEQ ID NO: 8) | (GAQP)5(GQKP) (SEQ ID NO: 46) | 60K (SEQ ID NO: 62) | Moiety A& |
| 041 | 8Aib,26R 34R,36G (SEQ ID NO: 5) | (GAQP)9(GQCP) (SEQ ID NO: 47) | 76C (SEQ ID NO: 66) | Moiety B&& |
| 042 | 8Aib,26R,34R,36G (SEQ ID NO: 5) | (GAQP)7(GQCP) (SEQ ID NO: 49) | 68C (SEQ ID NO: 67) | Moiety B&& |
| 043 | 8Aib,26R,34R,36G (SEQ ID NO: 5) | (GAQP)5(GQCP) (SEQ ID NO: 50) | 60C (SEQ ID NO: 68) | Moiety B&& |
| 052 | 8G,22E,26R 34R,36G (SEQ ID NO: 9) | (GAQP)9(GQCP) (SEQ ID NO: 47) | 76C (SEQ ID NO: 69) | Moiety B&& |
| 053 | 8G,22E,26R,34R,36G (SEQ ID NO: 9) | (GAQP)7(GQCP) (SEQ ID NO: 49) | 68C (SEQ ID NO: 70) | Moiety B&& |
| 054 | 8G,22E,26R,34R,36G (SEQ ID NO: 9) | (GAQP)5(GQCP) (SEQ ID NO: 50) | 60C (SEQ ID NO: 71) | Moiety B&& |
| 065 | 8Aib, 34R, 36G (SEQ ID NO: 3) | (GAQP)9(GQCP) (SEQ ID NO: 47) | 76C (SEQ ID NO: 75) | Moiety B&& |
| 066 | 8Aib, 34R, 36G (SEQ ID NO: 3) | (GAQP)7(GQCP) (SEQ ID NO: 49) | 68C (SEQ ID NO: 76) | Moiety B&& |
| 067 | 8Aib, 34R, 36G (SEQ ID NO: 3) | (GAQP)5(GQCP) (SEQ ID NO: 50) | 60C (SEQ ID NO: 77) | Moiety B&& |
| 068 | 8Aib, 22E, 34R, 36G (SEQ ID NO: 6) | (GAQP)9(GQCP) (SEQ ID NO: 47) | 76C (SEQ ID NO: 78) | Moiety B&& |
| 069 | 8Aib, 22E, 34R, 36G (SEQ ID NO: 6) | (GAQP)7(GQCP) (SEQ ID NO: 49) | 68C (SEQ ID NO: 79) | Moiety B&& |
| 070 | 8Aib, 22E, 34R, 36G (SEQ ID NO: 6) | (GAQP)5(GQCP) (SEQ ID NO: 50) | 60C (SEQ ID NO: 80) | Moiety B&& |
| 001 | 8Aib,34R,36G (SEQ ID NO: 3) | (GAQP)9(GQKP) (SEQ ID NO: 43) | 26K, 76K (SEQ ID NO: 51) | Moiety A& |
| 004 | 8Aib,34R,36G (SEQ ID NO: 3) | (GAQP)14(GQKP) (SEQ ID NO: 82) | 26K, 96K (SEQ ID NO: 85) | Moiety A& |
| 005 | 8Aib,34R,36G (SEQ ID NO: 3) | (GAQP)11(GQKP) (SEQ ID NO: 44) | 26K, 84K (SEQ ID NO: 53) | Moiety A& |
| 006 | 8Aib,34R,36G (SEQ ID NO: 3) | (GAQP)7(GQKP) (SEQ ID NO: 45) | 26K, 68K (SEQ ID NO: 54) | Moiety A& |
| 007 | 8Aib,34R,36G (SEQ ID NO: 3) | (GAQP)5(GQKP) (SEQ ID NO: 83) | 26K, 60K (SEQ ID NO: 86) | Moiety A& |
| 008 | 8Aib,34R,36G (SEQ ID NO: 3) | (GAQP)2(GQKP) (SEQ ID NO: 84) | 26K, 48K (SEQ ID NO: 87) | Moiety A& |
| 012 | 8Aib,22E,34R,36G (SEQ ID NO: 6) | (GAQP)9(GQKP) (SEQ ID NO: 43) | 26K, 76K (SEQ ID NO: 57) | Moiety A& |
| 015 | 8Aib,22E,34R,36G (SEQ ID NO: 6) | (GAQP)11(GQKP) (SEQ ID NO: 44) | 26K, 84K (SEQ ID NO: 58) | Moiety A& |
| 016 | 8Aib,22E,34R,36G (SEQ ID NO: 6) | (GAQP)7(GQKP) (SEQ ID NO: 45) | 26K, 68K (SEQ ID NO: 59) | Moiety A& |
| 036 | 8Aib,26C,34R,36G (SEQ ID NO: 4) | (GAQP)11(GQCP) (SEQ ID NO: 48) | 26C, 84C (SEQ ID NO: 63) | Moiety B&& |
| 037 | 8Aib,26C,34R,36G (SEQ ID NO: 4) | (GAQP)9(GQCP) (SEQ ID NO: 47) | 26C, 76C (SEQ ID NO: 64) | Moiety B&& |
| 038 | 8Aib,26C, 34R,36G (SEQ ID NO: 4) | (GAQP)7(GQCP) (SEQ ID NO: 49) | 26C, 68C (SEQ ID NO: 65) | Moiety B&& |
| 060 | 8Aib,22E,26C,34R,36G (SEQ ID NO: 7) | (GAQP)11(GQCP) (SEQ ID NO: 48) | 26C, 84C (SEQ ID NO: 72) | Moiety B&& |

TABLE 1-continued

| Exemplary polypeptide conjugate sequences | | | | |
|---|---|---|---|---|
| Molecule Code (MLC) | Mutations in GLP-1** (SEQ ID NO of the GLP-1) | Repeating sequences & No. of repeats (SEQ ID NO of the peptide linker) | CRM residue(s)[#] (SEQ ID NO of the polypeptide portion) | CRM |
| 061 | 8Aib,22E,26C,34R,36G (SEQ ID NO: 7) | (GAQP)9(GQCP) (SEQ ID NO: 47) | 26C, 76C (SEQ ID NO: 73) | Moiety B[&&] |
| 062 | 8Aib,22E,26C,34R,36G (SEQ ID NO: 7) | (GAQP)7(GQCP) (SEQ ID NO: 49) | 26C, 68C (SEQ ID NO: 74) | Moiety B[&&] |

**: Mutations in GLP-1 means mutations relative to SEQ ID NO: 1, wherein the first residue is 7H, and the last residue is 37G;

#: CRM residue(s) means position of the CRM residue counted from N to C in the polypeptide sequence containing GLP-1 (wherein the first residue is 7H) with its C-terminus attached to the peptide linker.

&: Moiety A refers to HOOC-(CH2)16-CO-gGlu-2XADO or

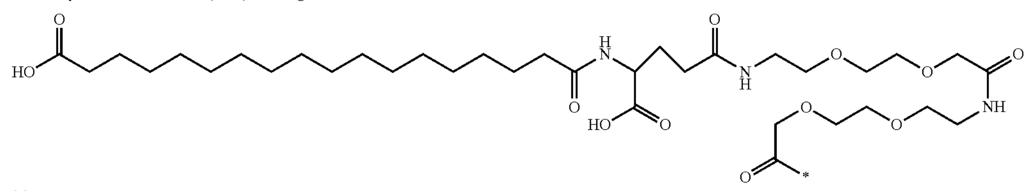

&&: Moiety B refers to HOOC-(CH2)16-CO-gGlu-2XADO-EDA-CO-CH2, or the following structure:

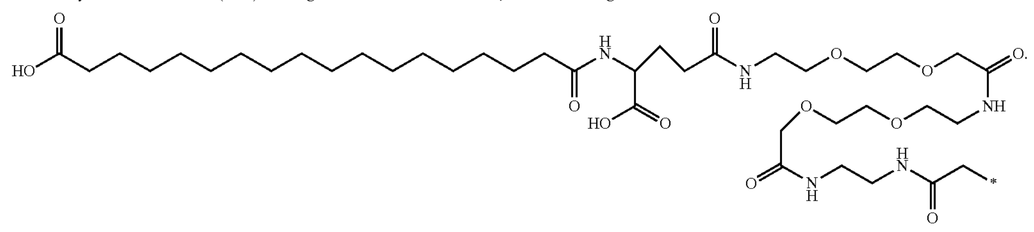

In certain embodiments, the polypeptide conjugate comprises a structure shown below (including the mono-conjugated Molecule 002 and Molecule 019, and the double-conjugated Molecule 012), where the amino acid residues are represented as one letter abbreviations in circles: Molecule 002:

Molecule 002

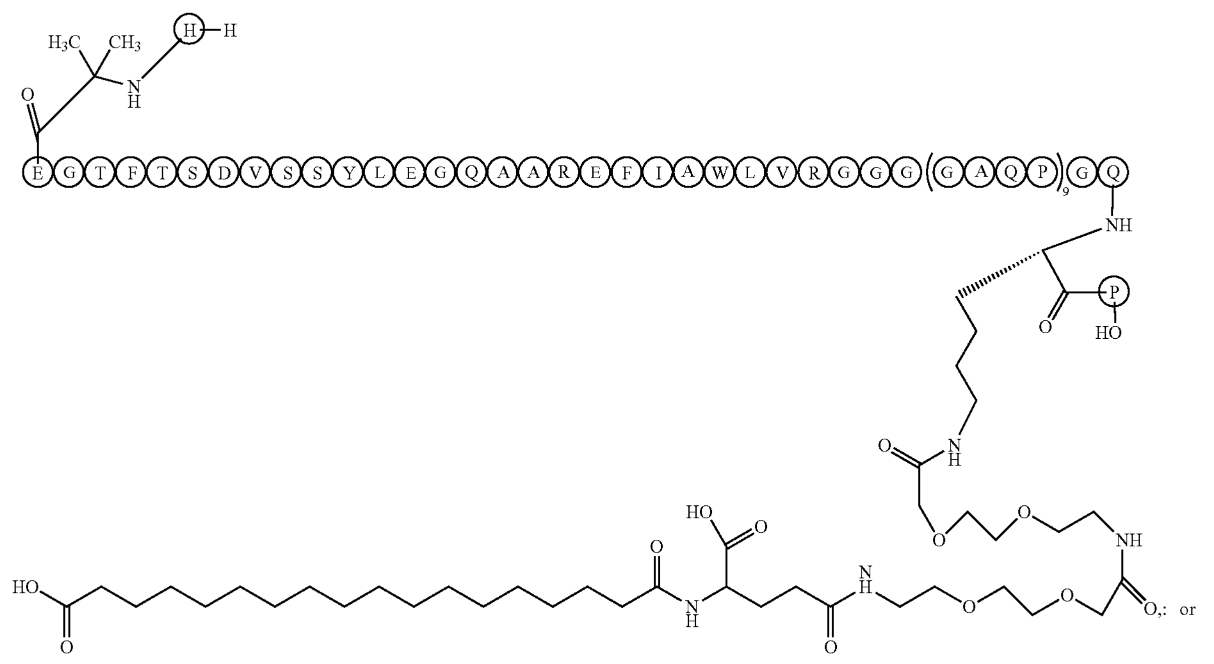

or

-continued

Molecule 019

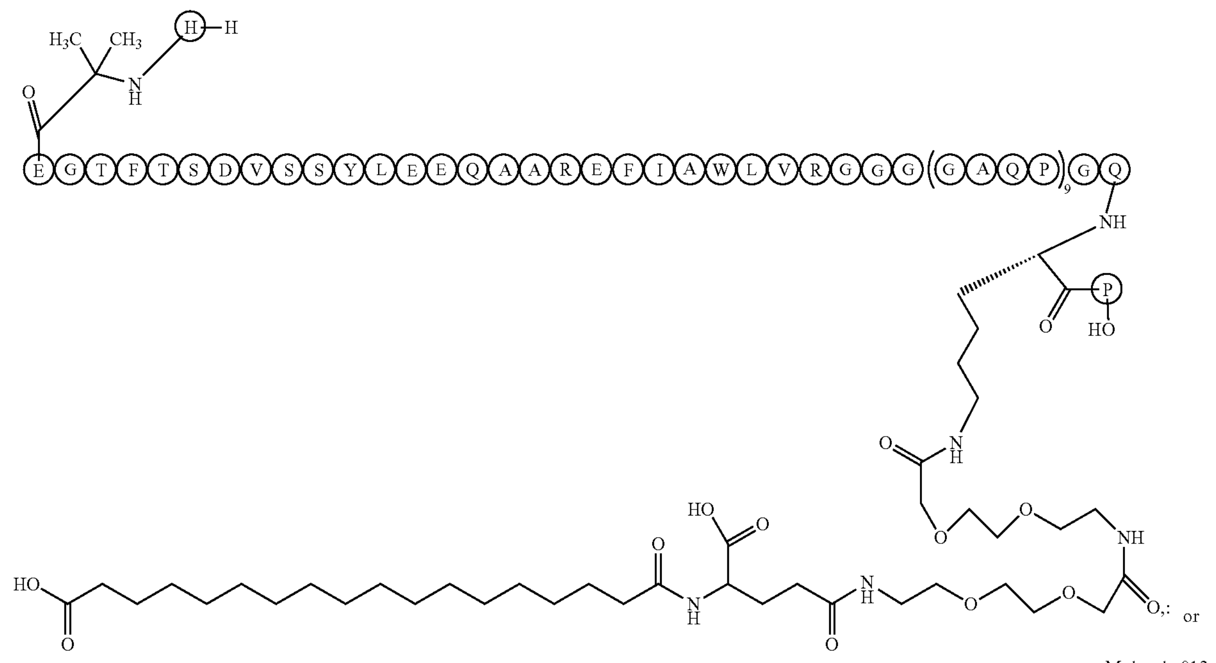

or

Molecule 012:

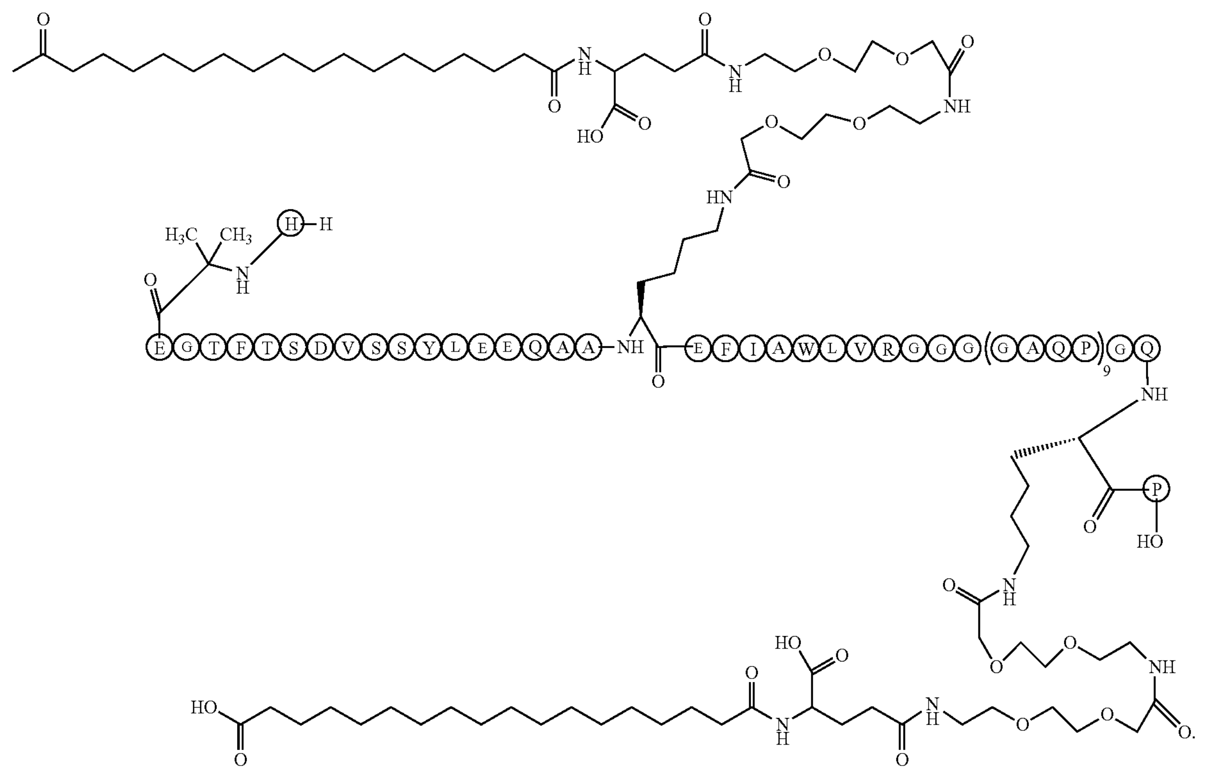

Method of Preparation

The present disclosure provides isolated nucleic acids or polynucleotides that encode the polypeptide portion (or a fragment thereof) of the polypeptide conjugates provided herein.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The nucleic acids or polynucleotides encoding the polypeptide provided herein (or fragment thereof) can be constructed using recombinant techniques. To this end, DNA encoding the GLP-1 receptor agonist (such as GLP-1) and DNA encoding the peptide linker can be obtained and operably linked to allow transcription and expression in a host cell to produce the fusion polypeptide. If needed, polynucleotide sequences encoding for one or more linkers are also operably linked to allow expression of the desired product.

The encoding polynucleotide sequences can be further operably linked to one or more regulatory sequences, optionally in an expression vector, such that the expression or production of the fusion polypeptides or polypeptide complexes is feasible and under proper control.

The encoding polynucleotide sequence(s) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. prokaryotic promoters such as T7, T7lac, Sp6, araBAD, trp, lac, tac, pLm, A3, lac, lpp, npr, pac, syn, trc and T3, or eukaryotic promoters such as SV40, CMV, and EF-1a), and a transcription termination sequence.

Vectors and Host Cells

In another aspect, the present disclosure provides a vector comprising the polynucleotide provided herein.

Vectors comprising the polynucleotide sequence(s) provided herein can be introduced to a host cell for cloning or gene expression. The phrase "host cell" as used herein refers to a cell into which an exogenous polynucleotide and/or a vector has been introduced. In other embodiments, the vectors are extra-chromosomal. The host cells can be isolated if desired. In certain embodiments, the host cell is a prokaryotic cell or eukaryotic cell.

Suitable host cells for cloning or expressing the DNA in the vectors herein are mainly prokaryotes. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. In some embodiments, host cells are eukaryotes, such as yeast and mammalian cells (e.g., immortalized mammalian cells).

A vector comprising the polynucleotide sequence(s) provided herein can be introduced into a host cell using any suitable method known to a skilled person in the art, e.g., transformation, transfection or transduction. In one example, the polynucleotide sequence encoding the GLP-1 polypeptide can be subcloned into an expression vector, which is expressed as inclusion bodies in the host cells. The vector can be a viral vector, and any suitable viral vector can be used in this capacity.

In another aspect, the present disclosure provides a host cell comprising the vector provided herein. The host cell is prokaryotic cell or a eukaryotic cell. Host cells transformed with the above-described expression or cloning vectors can be cultured in conventional nutrient media modified as appropriate for inducing promoters, selecting transformants, or amplifying the cloning vectors.

In another aspect, the present disclosure provides a method of producing the polypeptide conjugates provided herein, comprising culturing the host cell provided herein under a condition that allows expression of the polynucleotide provided herein to obtain the polypeptide portion of the polypeptide conjugate.

For production of the polypeptide portion provided herein, the host cells transformed with the expression vector may be cultured in a variety of media. Commercially available bacteria growth media such as Terrific Broth, LB Broth, LB Agar, M9 minimal media, MagiaMedia Medium, and ImMedia Medium (ThermoFisher) are suitable for culturing the bacterial host cells. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the eukaryotic host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In one aspect, the present disclosure provides a method of expressing the polypeptide portion of the polypeptide conjugates provided herein, comprising culturing the host cell provided herein under the condition at which the polypeptide portion is expressed. In certain embodiments, the polypeptide portion is expressed as a soluble polypeptide.

When using recombinant techniques, the polypeptide provided herein can be produced intracellularly, in the periplasmic space, or directly secreted into the medium. If the product is produced intracellularly, as a first step, the particulate debris, either host cells or lysed fragments, is removed, for example, by centrifugation or ultrafiltration. Carter et al., Bio/Technology 10:163-167 (1992) describe a procedure for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the product is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In certain embodiments, the method further comprises isolating the polypeptide.

The polypeptide provided herein prepared from the cells can be purified using, for example, hydroxylapatite chromatography, gel electrophoresis, dialysis, DEAE-cellulose ion exchange chromatography, ammonium sulfate precipitation, salting out, and affinity chromatography.

Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

In certain embodiments, the method further comprises conjugating the CRM to the polypeptide. The polypeptide can be conjugated at, for example, the lysine residue, the cysteine residue, or the non-natural amino acid by a suitable conjugation reaction.

For example, the polypeptide having one or more CRM residues such as lysine may be reacted with an amino-reactive agent. In certain embodiments, the CRM is conjugated to the lysine residue via an acyl group in an acylation reaction. Exemplary methods of acylation reaction is described in, for example, WO2009083549 and WO2010029159, the content of which is incorporated herein to its entirety. The CRM to be conjugated in an acylation reaction may contain a carboxylic acid group, an α,ω-fatty diacid residue, an activated ester, or an activated N-hydroxy imide ester, among others. Examples of activated esters include, 0-succinimide reagents like N-hydroxysuccinimidyl (NHS) or sulfo-NHS esters and imido ester compounds like Traut's reagent, which can react with the E-amino group of a conjugatable lysine residue to form amide or amidine bonds. Additional examples of suitable amino-reactive agent include, O-acylisourea, N-hydroxy trialzole esters, anhydride, phenyl active esters, P-hydroxamic active esters, acylimidazoles, acylbenzotriazoles, acyl azides, acid hylides, phophonium salts, aminium/uronium salts.

For another example, the polypeptide having one or more CRM residues such as cysteine may be linked to a thiol-reactive agent. In certain embodiments, the CRM is conjugated to the cysteine residue in an alkylation reaction. In certain embodiments, the CRM is conjugated to the conjugatable cysteine residue via a maleimide or an iodoacetamide to form a carbon-sulfur bond. In certain embodiments, the CRM is conjugated to the conjugatable cysteine residue via a disulphide to form a disulfide bond. Additional examples of suitable thiol-reactive group include, dienyl sulfone, -haloacyl, or other thiol-reactive conjugation partner. See, for details, Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671.

For example, the polypeptide having one or more CRM residues such as non-natural amino acid residue (NNAA) can be conjugated to a CRM such that a stable linkage can be formed between the NNAA of the fusion polypeptide and the CRM. For example, NNAAs containing keto group or aldehyde or p3-diketomoieties can react with a hydrazide- or O-alkylhydroxylamine-, hydroxylamine-containing agents to form a hydrazone or an O-alkylated oxime linkage. For another example, NNAAs containing an azide group can react with an alkyne derivative to form a stable triazole linker by copper (I) catalyzed [3+2]cycloaddition (and vice versa). For another example, NNAAs containing an azide group can be ligated with an appropriate water soluble phosphine-containing agent to form an amide linkage by a Staudinger ligation. Further, a thioester moiety in an NNAA can react with an amine-containing agent to form amide linkage. The fusion polypeptides provided herein incorporated with an NNAA can be conjugated with an agent via cycloaddition reactions, such as (4+2) cycloaddition between diene and dienophile (Diels-Alder reaction), (3+2) cycloaddtion via 1, 3-dipolar Huisgen cycloaddition, and (3+2) cycloaddtion via Nitrone-olefin cycloaddition. Cycloaddition methods suitable for antibody conjugation have been described in, for example, WO05003294, US20120004183, WO06009901, WO07130453 and U.S. Pat. No. 6,737,236.

For another example, the polypeptide may be conjugated to biotin, then indirectly conjugated to CRM that is conjugated to avidin. For still another example, the fusion polypeptide or the polypeptide complex may be linked to a coupling agent which further links to the CRM. Examples of the coupling agents include bifunctional moieties such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suherate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and his-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio) pentanoate (SPP) to provide for a disulphide linkage.

Additional methods for the conjugation of CRM to the polypeptides are found, for example, in U.S. Pat. No. 5,208,020; U.S. Pat. No. 6,4411,163; WO2005037992; WO2005081711; and WO2006/034488, which are incorporated herein by reference to the entirety. Specific examples of methods of preparing the conjugates of the present disclosure are also included in the experimental part of the present disclosure.

Pharmaceutical Composition

In another aspect, the present disclosure also provides a pharmaceutical composition comprising the polypeptide conjugate provided herein. In certain embodiments, the pharmaceutical composition is solid composition for oral administration.

Herein, the polypeptide conjugate substantially serves as the active pharmaceutical ingredient (API) in the pharmaceutical composition. In addition to the polypeptide conjugate, the pharmaceutical composition further comprises one or more pharmaceutically acceptable excipients.

The term "pharmaceutically acceptable" indicates that the designated excipient(s) is generally chemically and/or physically compatible with the other ingredients comprising the formulation, and physiologically compatible with the recipient thereof.

A "pharmaceutically acceptable excipient" refers to an ingredient in a pharmaceutical formulation, other than an active ingredient, which is bioactivity acceptable and non-toxic to a subject.

Examples of pharmaceutical acceptable excipients for oral solid formulation may include, antioxidants, fillers, binders, disintegrants, buffers, preservatives, lubricants, flavorings, thickeners, coloring agents, emulsifiers or stabilizers such as sugars and cyclodextrins. Oral solid formulations can include standard carriers such as pharmaceutical grades of mannitol, lactose, starch, magnesium stearate, polyvinyl pyrollidone, sodium saccharine, cellulose, magnesium carbonate, etc.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

In certain embodiments, the polypeptide conjugates described herein is formulated in a form suitable for oral administration. Standard pharmaceutical formulation techniques, such as those described in Remington: The Science and Practice of Pharmacy (D. B. Troy, Editor, 21st Edition, Lippincott, Williams & Wilkins, 2006), may be employed.

Oral Formulation

In another aspect, the pharmaceutical composition provided herein is suitable for oral administration. In another aspect, the pharmaceutical composition provided herein comprises the polypeptide conjugate provided herein and an absorption enhancing excipient.

According to some embodiments, the absorption enhancing excipient comprises a salt, e.g. a sodium salt, a potassium salt, or an ammonium salt, of N-(8-(2-hydroxybenzoyl) amino) caprylic acid. In certain embodiments, the absorption enhancing excipient is sodium N-(8-(2-hydroxybenzoyl) amino) caprylic acid (SNAC). The use of a salt of N-(8-(2-hydroxybenzoyl) amino) caprylic acid, e.g. SNAC, etc., as an absorption enhancing excipient or absorption enhancer has been described in the international application publication number WO2021023855A1.

While SNAC is known to be useful in enhancing absorption of small peptides after oral administration, the absorption-enhancing effect is diminishing for a molecule with a molecular weight of 4 kDa (approximately 36 amino acid residues) or greater. However, it is unexpectedly found in the present disclosure that, the polypeptide conjugates provided herein, despite of having a length much greater than 36 or 40 amino acid residues, can have an enhanced oral absorption when formulated with SNAC in a composition.

According to some embodiments, another of the pharmaceutically acceptable excipients in the pharmaceutical composition disclosed herein includes at least one lubricant, which are selected from the group consisting of magnesium stearate, calcium stearate, zinc stearate, colloidal silica, glyceryl behenate, polyethylene oxide polymers, sodium lauryl sulfate, magnesium lauryl sulfate, sodium oleate, sodium stearyl fumarate, stearic acid, hydrogenated vegetable oil, light mineral oil, silicon dioxide, alkyl sulfate, sodium benzoate, polyethylene glycol, talc, wax, and glyceride. In certain embodiments of the pharmaceutical composition disclosed herein, magnesium stearate is used as the lubricant.

According to some embodiments, the pharmaceutically acceptable excipients in the pharmaceutical composition disclosed herein may optionally include at least one filler, selected from the group consisting of microcrystalline cellulose (MCC), cellulose powder, hydroxymethylcellulose, hydroxyethylcellulose, hydroxypropylcellulose, hydroxypropylmethylcellulose, dibasic calcium phosphate, corn starch, and pregelatinized starch.

According to some embodiments, the pharmaceutically acceptable excipients in the pharmaceutical composition disclosed herein may optionally include at least one binder, selected from the group consisting of povidone, lactose, hydroxypropylcellulose, L-hydroxypropylcellulose, hypromellose (HPMC), methylcellulose polymers, hydroxyethylcellulose, ethylcellulose, sodium carboxymethylcellulose, other cellulose derivatives, sucrose, dextrins, maltodextrins, starches, calcium lactate, calcium carbonate, acacia, sodium alginate, agar, carrageenan, gelatin, guar gum, pectin, and PEG.

The use of lubricants, fillers, and/or binders as mentioned above in a pharmaceutical composition has been described in the international application publication numbers WO2012080471A1, WO2013139694A1, and WO2013139694A1.

According to some embodiments, the pharmaceutical composition provided herein comprises no filler or binder.

According to some embodiments, the pharmaceutical composition provided herein consists of the polypeptide conjugate, sodium N-(8-(2-hydroxybenzoyl) amino) caprylic acid (SNAC), and magnesium stearate.

The present disclosure further provides a pharmaceutical composition, which comprises, and according to certain embodiments: approximately 0.5-100 mg of the polypeptide conjugate; and approximately 50-500 mg of SNAC. In certain embodiments, the pharmaceutical composition is provided in a unit dosage form.

As used herein, the term "unit dosage form", "unit dose form" or alike, refers to a single entity for drug administration, or a physical form in which a drug is produced and dispensed, such as a tablet, a capsule, a sachet, or an injectable. A "unit dosage form" may also be referred to as a "fixed dosage form" (or "fixed dose form") or fixed dosage combination (or fixed dose combination), and are otherwise interchangeable.

In certain embodiments of the pharmaceutical composition, the SNAC constitutes at least 60% w/w (e.g. at least 62%, 65%, 68%, 70%, 72%, 75%, 78%, 80%, 81%, 82%, 83%, 84%, 85%, 86%, 87%, 88%, 89%, 90%, 91%, 92%, 93%, 94%, 95%, 96%, 97, 98%, or 99% etc.) of the unit dosage form.

In certain embodiments of the pharmaceutical composition, the SNAC constitutes from about 60% to about 99%, 60% to about 96%, 60% to about 95%, 60% to about 93%, 60% to about 92%, 60% to about 91%, 60% to about 90%, 60% to about 89%, 60% to about 88%, 60% to about 87%, 60% to about 86%, 60% to about 85%, 60% to about 70%, 80% to about 98% w/w of the unit dosage form.

In certain embodiments of the pharmaceutical composition, the unit dosage form thereof comprises up to 500 mg, up to 450 mg, up to 400 mg, up to 350 mg, up to 300 mg, up to 250 mg, up to 200 mg, up to 150 mg, up to 100 mg, up to 50 mg SNAC.

In certain embodiments of the pharmaceutical composition, the unit dosage form thereof comprises about 50 mg to about 500 mg, about 50 mg to about 450 mg, about 50 mg to about 400 mg, about 50 mg to about 350 mg, about 50 mg to about 300 mg, about 75 mg to about 300 mg, about 100 mg to about 300 mg, about 100 mg to about 500 mg, about 150 mg to about 300 mg, about 200 mg to about 300 mg SNAC.

In certain embodiments of the pharmaceutical composition, the polypeptide conjugate constitutes at least approximately 0.1% w/w (e.g. 0.3%, 0.5%, 0.7%, 0.9%, 1%, 2% etc.) and at most approximately 32% (e.g., 18%, 19%, 20%, etc.) of the unit dosage form.

In certain embodiments of the pharmaceutical composition, the unit dosage form thereof comprises up to 100 mg, up to 90 mg, up to 80 mg, up to 70 mg, up to 60 mg, up to 50 mg, up to 40 mg, up to 30 mg, up to 20 mg, up to 10 mg of the polypeptide conjugate.

In certain embodiments of the pharmaceutical composition, the unit dosage form thereof comprises 0.5-100 mg, 0.5-90 mg, 0.5-80 mg, 0.5-70 mg, 0.5-60 mg, 0.5-50 mg, 0.5-40 mg, 0.5-30 mg, 0.5-20 mg, 0.5-10 mg, 0.5-5 mg, 0.5-2.5 mg, 2.5-5 mg, 2.5-10 mg, 2.5-15 mg, 2.5-20 mg, 5-10 mg, 10-20 mg, 10-30 mg, 10-100 mg, 20-100 mg, or 20-50 mg of the polypeptide conjugate.

In certain embodiments, the pharmaceutical composition further comprises 1-20 mg lubricant, optionally the lubricant is magnesium stearate.

In any of the embodiments of the pharmaceutical composition as mentioned above, the dosage form thereof can be in a form selected from the group consisting of tablets, capsules, sachets, chewing gums, and powders.

In certain embodiments, the dosage form of the pharmaceutical composition is in a form of tablets.

Pharmaceutical Composition for Mono-Conjugated Polypeptide Conjugate

In certain embodiments, the polypeptide conjugate is single-conjugated, and the first CRM is the only one CRM in the conjugate portion of the polypeptide conjugate. Optionally, the first CRM residue is lysine residue, and further optionally, and the first CRM comprises Moiety A (HOOC-(CH2)16-CO-gGlu-2XADO), the Moiety A having the structure of below formula:

In certain embodiments, the SNAC constitutes from about 80% to about 98%, about 81% to about 98%, about 82% to about 98%, about 83% to about 98%, about 84% to about 98%, about 85% to about 98%, about 86% to about 98%, about 87% to about 98%, about 88% to about 98%, about 89% to about 98%, about 90% to about 98% w/w of the unit dosage form.

In certain embodiments, the unit dosage form thereof comprises up to 300 mg, up to 250 mg, up to 200 mg, up to 150 mg, up to 100 mg, or up to 50 mg SNAC.

In certain embodiments, the unit dosage form thereof comprises about 50 mg to about 300 mg, about 75 mg to about 300 mg, about 100 mg to about 300 mg, about 100 mg to about 500 mg, about 150 mg to about 300 mg, about 200 mg to about 300 mg SNAC.

In certain embodiments, the SNAC constitutes from about 91% to about 98% w/w of the excipients in the unit dosage form.

In certain embodiments, the polypeptide conjugate constitutes from about 0.1% w/w to about 20% w/w of the unit dosage form.

In certain embodiments, the polypeptide conjugate constitutes about 0.1% to about 20%, about 0.1% to about 19%, about 0.1% to about 18%, about 0.1% to about 17%, about 0.1% to about 16%, about 0.1% to about 15%, about 0.1% to about 14%, about 0.1% to about 13%, about 0.1% to about 12%, about 0.1% to about 11%, about 0.1% to about 10%, about 0.1% to about 9%, about 0.1% to about 8%, about 0.1% to about 7%, about 0.1% to about 6%, or about 0.1% to about 5% w/w of the unit dosage form.

In certain embodiments, the unit dosage form thereof comprises up to 50 mg, up to 40 mg, up to 30 mg, up to 20 mg, or up to 10 mg of the polypeptide conjugate.

In certain embodiments, the unit dosage form thereof comprises 0.5-50 mg, 0.5-40 mg, 0.5-30 mg, 0.5-20 mg, 0.5-10 mg, 0.5-5 mg, 0.5-2.5 mg, 2.5-5 mg, 2.5-10 mg, 2.5-15 mg, 2.5-20 mg, 5-10 mg, 10-20 mg, 10-100 mg, 10-30 mg, or 20-50 mg of the polypeptide conjugate.

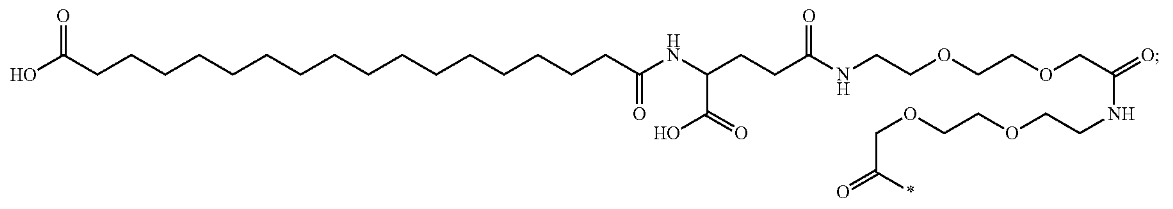 [SMILES: *C(=O)COCCOCCNC(=O)COCCOCCNC(=O)CCC(NC(=O)CCCCCCCCCCCCCCCCC(=O)O)C(=O)O]

and the unit dosage form comprises: approximately 0.5-50 mg (e.g. 0.5-10 mg, 0.5-2.5 mg, 2.5-5 mg, 5-10 mg, 10-20 mg, or 20-50 mg) of the polypeptide conjugate; and approximately 50-300 mg (e.g. 100-300 mg) of SNAC. In certain embodiments, the pharmaceutical composition further comprises 1-10 mg lubricant.

In certain embodiments of the pharmaceutical composition, the polypeptide portion of the polypeptide conjugate comprises an amino acid sequence of SEQ ID NO: 60, and is conjugated with the first CRM at 76K.

In certain embodiments of the pharmaceutical composition, the polypeptide portion of the polypeptide conjugate comprises an amino acid sequence of SEQ ID NO: 52, and is conjugated with the first CRM at 76K.

In certain embodiments, the SNAC constitutes at least 80% w/w (e.g. at least 80%, 89.7%, 81%, 82%, 83%, 84%, 85%, 86%, 87%, 88%, 89%, 90%, 91%, 92%, 93%, 94%, 95%, 96%, 97, 97.3%, 98%) of the unit dosage form.

In certain embodiments, the unit dosage form comprises 1-10 mg magnesium stearate.

In certain embodiments, the unit dosage form comprises approximately 0.5-50 mg of the polypeptide conjugate, approximately 50-300 mg of SNAC, and approximately 1-10 mg magnesium stearate.

In certain embodiments, the unit dosage form comprises: approximately 0.5-10 mg of the polypeptide conjugate, approximately 50-300 mg of SNAC, and approximately 1-10 mg magnesium stearate.

In certain embodiments, the unit dosage form comprises: approximately 10-20 mg of the polypeptide conjugate, approximately 100-300 mg of SNAC, and approximately 1-10 mg magnesium stearate.

In certain embodiments, the unit dosage form comprises: approximately 20-50 mg of the polypeptide conjugate, approximately 200-300 mg of SNAC, and approximately 1-10 mg magnesium stearate.

In certain embodiments, the unit dosage form comprises approximately 10-20 mg of the polypeptide conjugate, and approximately 100-300 mg of SNAC.

In certain embodiments, the unit dosage form comprises approximately 0.5 mg, 1 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg of the polypeptide conjugate.

In certain embodiments, the unit dosage form comprises approximately 20-50 mg of the polypeptide conjugate, and approximately 100-300 mg or 200-300 mg of SNAC.

According to some embodiments, when assayed in a standard disintegration test, the unit dosage form of the pharmaceutical composition completes disintegration in less than approximately 13 min 14 sec (e.g. 13 min, 12 min, 11 min, 10 min, 9 min, etc.).

According to some embodiments, when the unit dosage form is assayed in 500 mL medium of phosphate buffer with pH 6.8 containing 0.05% Brij 35 at 37° C., more than approximately 32.3% (e.g. 33%, 35%, 40%, etc.) of the polypeptide conjugate is dissolved at 5 min.

According to some embodiments, when the unit dosage form is assayed in 500 mL medium of phosphate buffer with pH 6.8 containing 0.05% Brij 35 at 37° C., more than approximately 72.1% (e.g. 73%, 75%, 80%, etc.) of the polypeptide conjugate is dissolved at approximately 15 min.

According to some embodiments, when the unit dosage form is assayed in 500 mL medium of phosphate buffer with pH 6.8 containing 0.05% Brij 35 at 37° C., more than approximately 38.7% (e.g. 39%, 40%, 50%, etc.) of the SNAC is dissolved at approximately 5 min.

According to some embodiments, when the unit dosage form is assayed for oral exposure in beagle dogs, more than approximately 78.7% (e.g. 79%, 80%, 82%, 85%, etc.) of the SNAC is dissolved at approximately 15 min.

Pharmaceutical Composition for Double-Conjugated Polypeptide Conjugate

In certain embodiments of the pharmaceutical composition, the polypeptide conjugate is double-conjugated, and the conjugate portion of the polypeptide conjugate further comprises a second CRM conjugated to a second CRM residue in the polypeptide portion. Optionally, the second CRM residue is lysine residue, and further optionally, each of the first CRM and the second CRM comprises Moiety A (HOOC-(CH2)16-CO-gGlu-2XADO), the Moiety A having the structure of below formula:

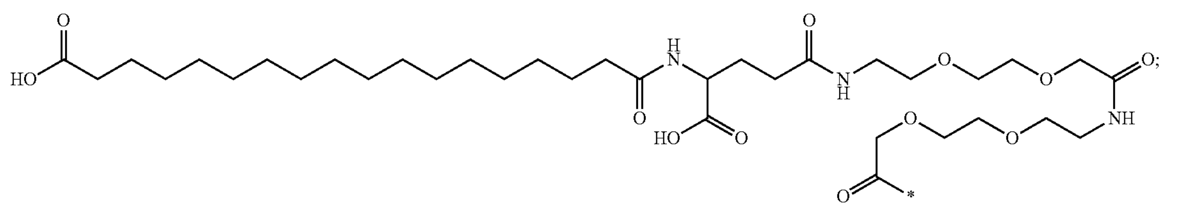 [SMILES: *C(=O)COCCOCCNC(=O)COCCOCCNC(=O)CCC(NC(=O)CCCCCCCCCCCCCCCCC(=O)O)C(=O)O]

wherein a dosage form of the pharmaceutical composition comprises: approximately 10-100 mg (e.g. 10-20 mg, 20-30 mg, 20-40 mg, 20-50 mg, 50-70 mg, or 80-100 mg, etc.) of the polypeptide conjugate; and approximately 50-500 mg (e.g. 50-100 mg, 100-200 mg, 250-500 mg, etc.) of SNAC. In some embodiments, the pharmaceutical composition further comprises 1-20 mg lubricant.

In some embodiments of the pharmaceutical composition, the polypeptide portion of the polypeptide conjugate comprises an amino acid sequence of SEQ ID NO: 57, and is conjugated with the first CRM and the second CRM respectively at 26K and 76K.

In some embodiments, the SNAC constitutes from about 60% to about 96%, about 62% to about 96%, about 65% to about 96%, about 66% to about 96%, about 67% to about 96%, about 68% to about 96%, about 70% to about 96%, about 72% to about 96%, about 75% to about 96%, about 78% to about 96%, about 80% to about 96%, about 86% to about 96%, about 87% to about 96%, w/w of the unit dosage form.

In some embodiments, the unit dosage form thereof comprises up to 500 mg, up to 450 mg, up to 400 mg, up to 350 mg, up to 300 mg, up to 250 mg, up to 200 mg, up to 150 mg, up to 100 mg SNAC.

In some embodiments, the unit dosage form thereof comprises about 100 mg to about 500 mg, about 100 mg to about 450 mg, about 100 mg to about 400 mg, about 100 mg to about 350 mg, about 100 mg to about 300 mg SNAC.

In some embodiments, the SNAC constitutes from about 91% to about 98% w/w of the excipients in the unit dosage form.

In some embodiments, the polypeptide conjugate constitutes at least 1% w/w and at most 32% w/w of the unit dosage form.

In some embodiments, the unit dosage form thereof comprises up to 100 mg, up to 90 mg, up to 80 mg, up to 70 mg, up to 60 mg, up to 50 mg, up to 40 mg, up to 30 mg, up to 20 mg, up to 10 mg of the polypeptide conjugate.

In some embodiments, the unit dosage form thereof comprises 10-100 mg, 10-90 mg, 10-80 mg, 10-70 mg, 10-60 mg, 10-50 mg, 10-40 mg, 20-100 mg, 20-90 mg, 20-80 mg, 20-70 mg, 20-60 mg, 20-50 mg, 20-40 mg of the polypeptide conjugate.

In some embodiments, the unit dosage form comprises 1-20 mg magnesium stearate.

In some embodiments, the unit dosage form thereof comprises: approximately 10-100 mg of the polypeptide conjugate; approximately 100-500 mg of SNAC, and approximately 1-20 mg magnesium stearate.

In some embodiments, the unit dosage form comprises: approximately 10-20 mg of the polypeptide conjugate, approximately 100-300 mg of SNAC, and approximately 1-20 mg magnesium stearate.

In some embodiments, the unit dosage form comprises: approximately 20-40 mg of the polypeptide conjugate, approximately 200-300 mg of SNAC, and approximately 1-20 mg magnesium stearate.

In some embodiments, the unit dosage form comprises: approximately 20-50 mg of the polypeptide conjugate, approximately 200-300 mg of SNAC, and approximately 1-20 mg magnesium stearate.

In some embodiments, the unit dosage form comprises: approximately 40-50 mg of the polypeptide conjugate, approximately 200-300 mg of SNAC, and approximately 1-20 mg magnesium stearate.

In some embodiments, the unit dosage form comprises: approximately 50-100 mg of the polypeptide conjugate, approximately 300-500 mg of SNAC, and approximately 1-20 mg magnesium stearate.

In some embodiments, the unit dosage form comprises approximately 0.5 mg, 1 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, or 100 mg of the polypeptide conjugate.

In some embodiments, the unit dosage form comprises approximately 10-20 mg (e.g. 10-15 mg, or 15-20 mg) of the polypeptide conjugate and approximately 50-300 mg of the SNAC, optionally 100-300 mg (e.g. approximately 50-100 mg, 100-200 mg, 200-300 mg, etc.) of the SNAC.

In some embodiments, the unit dosage form comprises approximately 10 mg, 11 mg, 12 mg, 13 mg, 14 mg, 15 mg, 16 mg, 17 mg, 18 mg, 19 mg, or 20 mg of the polypeptide conjugate.

In some embodiments, the unit dosage form comprises approximately 20-50 mg of the polypeptide conjugate and approximately 100-300 mg or optionally, 200-300 mg of the SNAC.

In some embodiments, the unit dosage form comprises approximately 20 mg, 25 mg, 30 mg, 35 mg, 40 mg, 45 mg, or 50 mg of the polypeptide conjugate.

In some embodiments, the unit dosage form comprises approximately 50-100 mg of the polypeptide conjugate and approximately 100-500 mg or optionally, 200-500 mg, or optionally 300-500 mg of the SNAC.

In some embodiments, the unit dosage form comprises approximately 50 mg, 55 mg, 60 mg, 65 mg, 70 mg, 75 mg, 80 mg, 85 mg, 90 mg, 95 mg or 100 mg of the polypeptide conjugate.

Herein according to some embodiments of the pharmaceutical composition, when the dosage form is assayed in a standard disintegration test, the dosage form completes disintegration in less than 11 min, or preferably less than 10 min, 9 min, 8 min, 7 min, or 6 min.

Herein according to some embodiments of the pharmaceutical composition, when the dosage form is assayed in 500 mL medium of phosphate buffer with pH 6.8 containing 0.05% Brij 35 at 37° C., more than 40%, preferably more than 50%, 75%, or 80% of the polypeptide conjugate is dissolved at 5 min.

Herein according to some embodiments of the pharmaceutical composition, when the dosage form is assayed in 500 mL medium of phosphate buffer with pH 6.8 containing 0.05% Brij 35 at 37° C., more than 82%, preferably more than 85%, 90%, or 95% of the polypeptide conjugate is dissolved at 15 min.

Herein according to some embodiments of the pharmaceutical composition, when the unit dosage form is assayed in 500 mL medium of phosphate buffer with pH 6.8 containing 0.05% Brij 35 at 37° C., more than approximately 37.4% (e.g. 37.4%, 38%, 40%, etc.) of the SNAC is dissolved at approximately 5 min.

Herein according to some embodiments of the pharmaceutical composition, when the unit dosage form is assayed for oral exposure in beagle dogs, more than approximately 82.1% (e.g. 82.1%, 83%, 85%, etc.) of the SNAC is dissolved at approximately 15 min.

Method of Treatment

In another aspect, the present disclosure provides a method of preventing or treating a metabolic disorder in a subject in need thereof, comprising administering a therapeutically effective amount of the polypeptide conjugate or a pharmaceutical composition provided herein.

Therapeutic methods are also provided, comprising: administering a therapeutically effective amount of the polypeptide conjugate provided herein to a subject in need thereof, thereby treating or preventing a condition or a disorder. In certain embodiments, the subject has been identified as having a disorder or condition likely to respond to the polypeptide conjugate provided herein.

In certain embodiments, the metabolic disorder is diabetes, obesity, overweight, non-alcoholic steatohepatitis (NASH), cardiovascular like dyslipidemia, atherosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC), or Alzheimer's disease.

In certain embodiments, the condition diabetes includes all forms of diabetes, such as hyperglycemia, type 2 diabetes, impaired glucose tolerance, type 1 diabetes, non-insulin dependent diabetes, MODY (maturity onset diabetes of the young), gestational diabetes, and/or an elevated level of HbA1C.

In certain embodiments, the condition diabetes includes diabetic complications such as angiopathy.

In certain embodiments, the present disclosure provides a method of preventing or treating Alzheimer's disease in a subject in need thereof, comprising administering a therapeutically effective amount of the polypeptide conjugate or a pharmaceutical composition provided herein. The term "Alzheimer's disease" as used herein is intended to encompass to all forms of and stages of Alzheimer's disease. Alzheimer's disease is a progressive, degenerative brain disorder that gradually impairs memory, cognitive function, and behavior. There are five stages of Alzheimer's disease, which include preclinical Alzheimer's disease, mild cognitive impairment caused by Alzheimer's disease, mild dementia resulting from Alzheimer's disease, moderate dementia linked to Alzheimer's disease, and severe dementia associated with Alzheimer's disease. The term "dementia" is used to refer to a collection of symptoms that significantly impact intellectual and social capabilities, ultimately interfering with daily functioning. There are the two predominant forms of the Alzheimer's disease: Familial Alzheimer's disease and Sporadic or Late onset Alzheimer's disease. Familial Alzheimer's disease is typically caused by inherited genetic mutations, including mutations in one of three genes: APP, PSEN1 or PSEN2. This form of the disease is a rare and devastating illness with onset potentially occurring in mid-life. The second and far more common form of the disease is Sporadic or Late onset Alzheimer's disease, which is the most common form and occurs without any known genetic cause. In some embodiments, the subject has or suffer from Alzheimer's disease may have the symptoms selected from the group of cognitive deficits including memory impairment, language dysfunction, and visuospatial skills; functional impairment that may span occupational and social issues (e.g., activities of daily living); and behavioral symptoms including depression, anxiety, aggression and psychosis may also appear as the disease progresses in severity.

In certain embodiments, the subject has preclinical Alzheimer's disease, mild cognitive impairment caused by Alzheimer's disease, mild dementia resulting from Alzheimer's disease, moderate dementia linked to Alzheimer's disease, or severe dementia associated with Alzheimer's disease.

In certain embodiments, the subject has Familial Alzheimer's disease or Sporadic Alzheimer's disease.

It has been reported that conjugated GLP-1 agonist, for example, semaglutide, can be useful for treating Alzheimer's disease, see for example, published U.S. Patent Application US2022/0280612A1, which is incorporated herein to its entirety. It has been reported that GLP-1 agonist semaglutide reduced measures of neuro-inflammation which may affect cognition and function in animal studies relevant to Alzheimer's disease. Furthermore, real-world evidence suggests a possible link between a reduced risk of dementia and treatment with GLP-1 agonists. In subjects who received GLP-1 agonist treatment, the rate of developing dementia was significantly lower.

The present disclosure shows the polypeptide conjugate provided herein are effective in treating Alzheimer's disease. In certain embodiments, the polypeptide conjugate provided herein are effective in improving cognitive function such as memory and attention, and/or delay the onset or progression of Alzheimer's disease. In certain embodiments, the polypeptide conjugate provided herein are more effective than semaglutide in treating Alzheimer's disease.

In another aspect, the present disclosure provides a method of managing body weight in a subject in need thereof, comprising administering a therapeutically effective amount of the polypeptide conjugate provided herein.

In another aspect, the present disclosure provides a method of reducing food intake in a subject in need thereof, comprising administering a therapeutically effective amount of the polypeptide conjugate provided herein.

In another aspect, the present disclosure provides a method of reducing body weight in a subject in need thereof, comprising administering a therapeutically effective amount of the polypeptide conjugate provided herein.

In certain embodiments, the condition or metabolic disorder that can be treated or ameliorated using the polypeptide conjugate provided herein, includes a condition where a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL.

In certain embodiments, the condition or metabolic disorder that can be treated or ameliorated using the polypeptide conjugate provided herein, includes a condition where a human subject has a body mass index (BMI) of at least or higher than 25, 26, 27, 28, 29, 30, 31, 32, 33, 34, 35, 36, 37, 38, 39 or 40. In certain embodiments, the human subject has an BMI ranging from 25 to 30, 26 to 30, 27 to 30, 28 to 30, 25 to 29, or 25 to 28.

The therapeutically effective amount of the polypeptide conjugate provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements. The therapeutically effective amount can be an amount of the fusion polypeptide, the polypeptide complex and the conjugate provided herein, that elicits a biological or medicinal response in a tissue system, animal, or human being sought by a researcher, medical doctor, or other clinician, which includes alleviation or amelioration of the symptoms of the disease or disorder being treated, i.e., an amount that supports an observable level of one or more desired biological or medicinal response, for example lowering blood glucose, insulin, triglyceride, or cholesterol levels; reducing body weight; or improving glucose tolerance, energy expenditure, or insulin sensitivity.

In certain embodiments, the polypeptide conjugate provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the polypeptide conjugate provided herein is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

In certain embodiments, the polypeptide conjugate provided herein may be administered orally to the subject (e.g. human) at a dosing regimen that is, or is no more frequently than, twice daily, once daily, once every 2 days, once every 3 days, once weekly, once every two weeks, once every three weeks, or once monthly. In certain embodiments, the polypeptide conjugate provided herein may be administered to the subject (e.g. human) at a dosing interval of once weekly, once every two weeks, once every three weeks, or once monthly. Therapeutic efficacy with low dosing frequency have the potential to improve a patient's adherence and long-term treatment success. The currently available treatment semaglutide is dosed once weekly. Without wishing to be bound by any theory, it is believed that certain polypeptide conjugate provided herein have significantly extended half life and are suitable for less frequent dosing than semaglutide for treating a metabolic condition, for example, less frequent than once weekly dosing (e.g. once every 8 days, once every 9 days, once every 10 days, once every 11 days, once every 12 days, once every 13 days, once every 14 days, once every 18 days, once every three weeks, once every 24 days, once every 4 weeks, or once every month). In certain embodiments, the dosing regimen is a continuous dosing regimen selected from twice-weekly dosing, once-weekly dosing, once bi-weekly dosing, once every three weeks dosing, once monthly dosing, or once every two months dosing. In certain embodiments, the dosing regimen has a dosing interval ranging from about once every 3 days to about once per month, or from about once weekly to about once per month.

Dosage regimens may be adjusted to provide the optimum desired response (e.g., a therapeutic response). For example, a single dose may be administered, or several divided doses may be administered over time.

The pharmaceutical composition provided herein may be administered orally.

The polypeptide conjugate may be administered alone or in combination with one or more additional therapeutic means or agents.

In certain embodiments, when used for treating a metabolic disease, the polypeptide conjugate provided herein may be administered in combination with any other therapeutic agent for use in the treatment of a metabolic disease or any medical disorder that related. "Administered in combination" as used herein includes administration simultaneously as part of the same pharmaceutical composition, simultaneously as separate compositions, or at different timings as separate compositions. A composition administered prior to or after another agent is considered to be administered "in combination" with that agent as the phrase is used herein, even if the composition and the second agent are administered via different routes. Where possible, additional therapeutic agents administered in combination with the fusion polypeptide, the polypeptide complex or the conjugate provided herein are administered according to the schedule listed in the product information sheet of the additional therapeutic agent, or according to the Physicians' Desk Reference (Physicians' Desk Reference, 70th Ed (2016)) or protocols well known in the art. A non-limiting list of examples of compounds that can be administered in combination with a pharmaceutical composition comprising the polypeptide conjugates provided herein, include rosiglitizone, pioglitizone, repaglinide, nateglitinide, metformin, exenatide, stiagliptin, pramlintide, glipizide, glimeprirideacarbose, and miglitol.

Kit

Also provided are kits for practicing the disclosed methods. Such kits can comprise a pharmaceutical composition such as those described herein, including nucleic acids encoding the polypeptide conjugate provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of the polypeptide conjugate provided herein or a mutant form thereof; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, diabetes, obesity, non-alcoholic steatohepatitis (NASH), cardiovascular like dyslipidemia, atherosclerosis, alcoholic steatohepatitis (ASH), diabeticnephropathy, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC), or Alzheimer's disease.

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded. Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

Example 1: Recombinant Expression and Purification of GLP-1 Proteins

The GLP-1 fusion polypeptide listed in Table 1 (i.e., SEQ ID NOs: 51-80, 85-88) were produced from bacterial *E. coli* expression system, using BL21(DE3) derivative strain. The DNA coding for the tagged GLP-1 fusion polypeptides was codon optimized for *E. coli* expression, de novo synthesized and subcloned into PET derivative expression vectors (Novagen). Amino acid substitutions were accomplished by modification of the corresponding genetic codes. Overexpression of the tagged GLP-1 fusion polypeptides was induced with 0.5 mM isopropyl b-d-thiogalactoside (IPTG) when the cell density reached an OD600 of 2.0 in Terrific Broth (TB) medium. The cells were harvested after protein induction at 37° C. for 20-22 hours. Cells were harvested and lysed in 20 mM Tris pH8.0, 0.15M NaCl buffer by cell disruptor (900 bar, for twice). The soluble fractions, containing the tagged GLP-1 fusion polypeptides, were collected and by centrifugation (8,000×g, for 30 min). After removing tag by protease, the GLP-1 fusion polypeptides were purified by reverse phase chromatography. The samples in each step were characterized by LC/MS to confirm the correct molecular weight.

Example 2: Incorporation of Non-Proteogenic Amino Acid in Recombinant Protein The N-terminal His-Aib-Glu-Gly tetrapeptide or His-Aib dipeptide was dissolved in organic solvent and was added into a solution of GLP-1 fusion polypeptides in organic solvent. The reaction was stirred at room temperature for 3 h. Then the piperidine was added into the reaction solution to remove Fmoc-protecting group.

Example 3: Preparation of GLP-1 Polypeptide Conjugates

To a solution of the GLP-1 fusion polypeptides obtain in Example 2 in NaOH was added with CRM reagent (e.g. HOOC-(CH2)16-CO-gGlu-2XADO, HOOC-(CH2)16-CO-gGlu-2XADO-EDA-CO-CH2, etc.) in organic solvent dropwise. The reaction was stirred at room temperature for 1 h. Then the product was applied to reverse phase chromatography. This provided the GLP-1 polypeptide conjugates as listed in Table 1 as shown above.

The GLP-1 polypeptide conjugates were detected and characterized by LC-MS method with Waters BioAccord LC-MS system, or by UPLC with Waters Acquity UPLC system, using conditions optimized for different conjugates, following the supplier's manuals.

Example 4a: In Vitro Activities

Method: The in vitro GLP-1 activities were measured using a BHK cell line overexpressing human GLP-1 receptor and CRE luciferase reporter with or without 1% human serum albumin (HSA). Tested GLP-1 polypeptide conjugates were measured at 1 nM or 100 nM as top concentration when in the absence or presence of 1% HSA with 3-fold serial dilutions. After cells were treated with molecules for 4 hours, luciferase activities were measured by Steadylite plus kit (Perkin Elmer, 6066751).

The activity of each GLP-1 polypeptide conjugate was represented by EC50, derived from non-linear regression analysis.

Conclusion: Almost all molecules (i.e. GLP-1 polypeptide conjugates) show comparable or even better potency than semaglutide in the assay without HSA supplement. However, different molecules exhibited different degrees of reduction in GLP-1 activity (i.e. increased $EC_{50}$) in the presence of 1% HSA. Data in Table 2a and 2b suggested that linker length, fatty acid position and number of conjugated fatty acid moieties could be relevant to GLP-1 activities. As shown in Table 2, the molecules (whether mono-acylation or double-acylation) having a short linker length (i.e. 12 amino acid residues) had significantly reduced GLP1-activity, as compared with those molecules with longer linker lengths. As the distance increased between the C-terminal residue of GLP-1 and the CRM residue (i.e. lysine in the linker), the GLP-1 activity of the molecules in the presence of HSA seemed to steadily improve.

As shown in Table 2a, mono-acylated Molecules 002, 010 and 011 showed much higher activity than semaglutide in the presence of 1% HSA. For double-acylated Molecules 012, 016, 004, 006, 007, 005, 001 and 061, all showed relatively lower GLP-1 activity in the presence of 1% HSA than semaglutide but were still in an acceptable range.

TABLE 2a

In vitro activities of GLP-1 polypeptide conjugates. To measure in vitro GLP-1 activity, a BHK cell line overexpressing human GLP-1 receptor was used.

| Molecule Code. | Linker length (aa) | Fatty acid number | Fatty acid position | GLP-1 activity ($EC_{50}$, pM) | GLP-1 activity ($EC_{50}$, pM, 1% HSA) |
|---|---|---|---|---|---|
| Semaglutide | 0 | Mono | GLP-1 | 4.2 | 243.8 |
| 001 | 40 | Double | GLP-1 and linker | 2.8 | 1036 |
| 002 | 40 | Mono | Linker | 1.1 | 8.6 |
| 005 | 48 | Double | GLP-1 and linker | 5.0 | 1537 |
| 006 | 32 | Double | GLP-1 and linker | 4.0 | 1387 |
| 007 | 24 | Double | GLP-1 and linker | 4.7 | 3238 |
| 008 | 12 | Double | GLP-1 and linker | 4.6 | 8732 |
| 004 | 60 | Double | GLP-1 and linker | 3.0 | 984.4 |
| 012 | 40 | Double | GLP-1 and linker | 2.1 | 1051 |
| 016 | 32 | Double | GLP-1 and linker | 2.1 | 1459 |
| 010 | 24 | Mono | Linker | 1.7 | 22.9 |
| 011 | 12 | Mono | Linker | 3.7 | 43.9 |
| 061 | 40 | Double | GLP-1 and linker | 4.4 | 2213 |

Example 4b: In Vitro Activities

Method: The in vitro GLP-1 activities were measured using a CHO cell line overexpressing human GLP-1 receptor and GRE luciferase reporter with or without 1% human serum albumin (HSA). Tested GLP-1 polypeptide conjugates were measured at 30 nM or 600 nM as top concentration when in the absence or presence of 1% HSA with 3-fold serial dilutions. After cells were treated with molecules for 5 hours, luciferase activities were measured by Bright-Glo Luciferase Assay System (Promega, E2620). The activity of each GLP-1 polypeptide conjugate was represented by EC50, derived from non-linear regression analysis.

Conclusion: As shown in Table 2b, mono-acylated Molecules 002 (1006) and 019 (1023) showed much higher activity than semaglutide in the presence of 1% HSA.

TABLE 2b

In vitro activities of GLP-1 polypeptide conjugates. To measure in vitro GLP-1 activity, a CHO cell line overexpressing human GLP-1 receptor was used.

| Molecule Code. | Linker length (aa) | Fatty acid number | Fatty acid position | GLP-1 activity ($EC_{50}$, nM) | GLP-1 activity ($EC_{50}$, nM, 1% HSA) |
|---|---|---|---|---|---|
| Semaglutide | 0 | Mono | GLP-1 | 0.33 | 23.8 |
| 002 | 40 | Mono | Linker | 0.12 | 3.47 |
| 019 | 40 | Mono | Linker | 0.07 | 2.16 |

Example 5: In Vivo Activities in C57 Lean Mice

Method: 10 week old male C57BL/6 mice were injected subcutaneously with protein once on Day1. Body weight was measured daily and five animals were used for each treatment group. Body weight was monitored for each individual animal. % BW loss=100*(BW on Day n−BW on Day 1)/(BW on Day 1). Data are indicated as mean values and standard error (SEM). The area under the curve for body weight loss (%) from 0 until 8 days (AUC ΔBW 0-8d) was calculated.

Figure 1B:
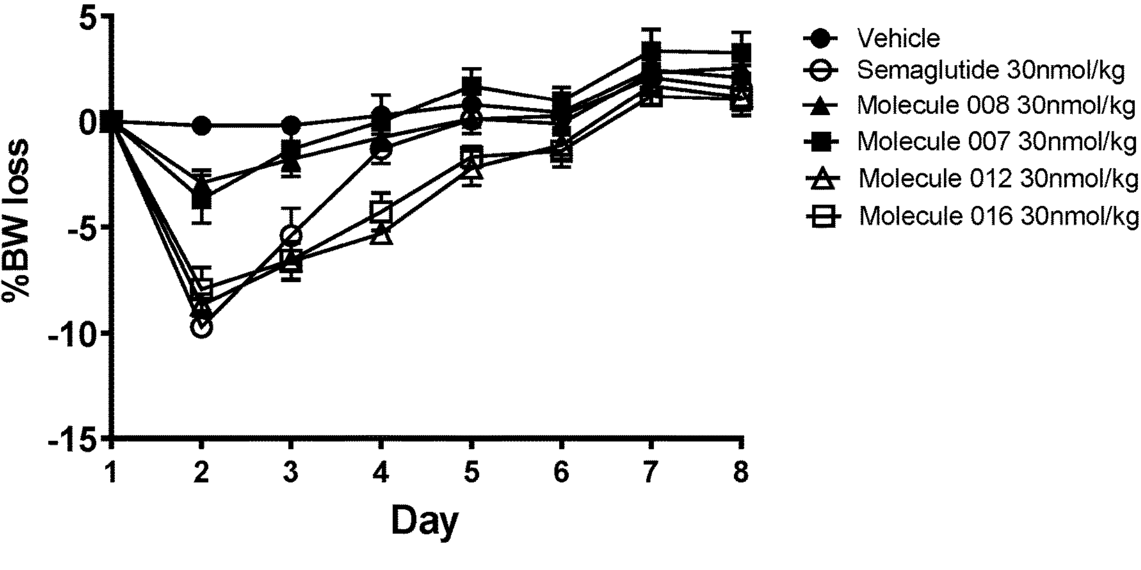

Conclusion: Molecules 001 and 012 showed dose dependent efficacy on body weight control (FIGS. 1A and Table 3). As shown in FIG. 1D and Table 3, Molecules 007 and 008 have less efficacy than Molecules 012 and 016 which is consistent with the in vitro activity data. Molecules 001, 016 and 012 with double fatty acids exhibited more sustainable efficacy than semaglutide, suggesting Molecules 001, 016 and 012 may have longer half-life (FIGS. 1A and 1B).

TABLE 3

The area under the curve for body weight loss (%) from 0 until 8 days (AUC ΔBW 0-8 d) in C57 lean mice studies.

| Studies | Group | AUC ΔBW 0-8 d (day*%) |
|---|---|---|
| Study 1 (FIG. 1A) | Semaglutide 30 nmol/kg | −9.3 |
| | Molecule 012 30 nmol/kg | −13.6 |
| | Molecule 012 100 nmol/kg | −28.3 |
| | Molecule 001 100 nmol/kg | −25.9 |
| Study 2 (FIG. 1B) | Semaglutide 30 nmol/kg | −13.2 |
| | Molecule 008 30 nmol/kg | −1.85 |
| | Molecule 007 30 nmol/kg | −2.63 |
| | Molecule 012 30 nmol/kg | −21.6 |
| | Molecule 016 30 nmol/kg | −20.1 |

Example 6a: In Vivo Activities in db/db Mice

Method: 10 week old male db/db mice were injected subcutaneously with GLP-1 polypeptide conjugate once.

Fasting glucose was measured on different times and three animals were used for each group. Delta blood glucose is glucose subtracted by baseline level. Data are indicated as mean values and standard error (SEM).

Figure 2A:
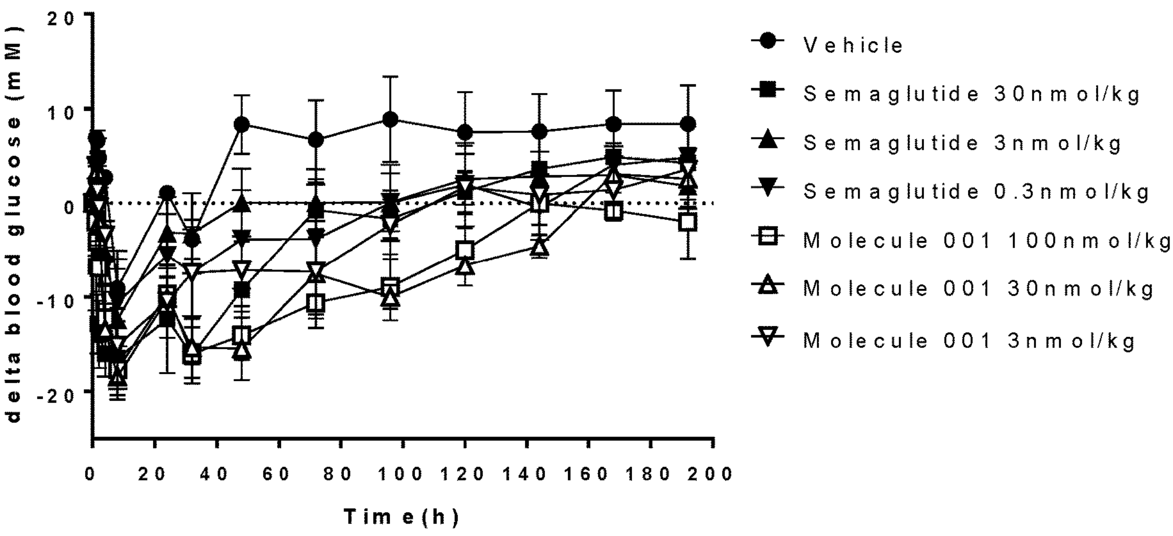
Figure 2B:
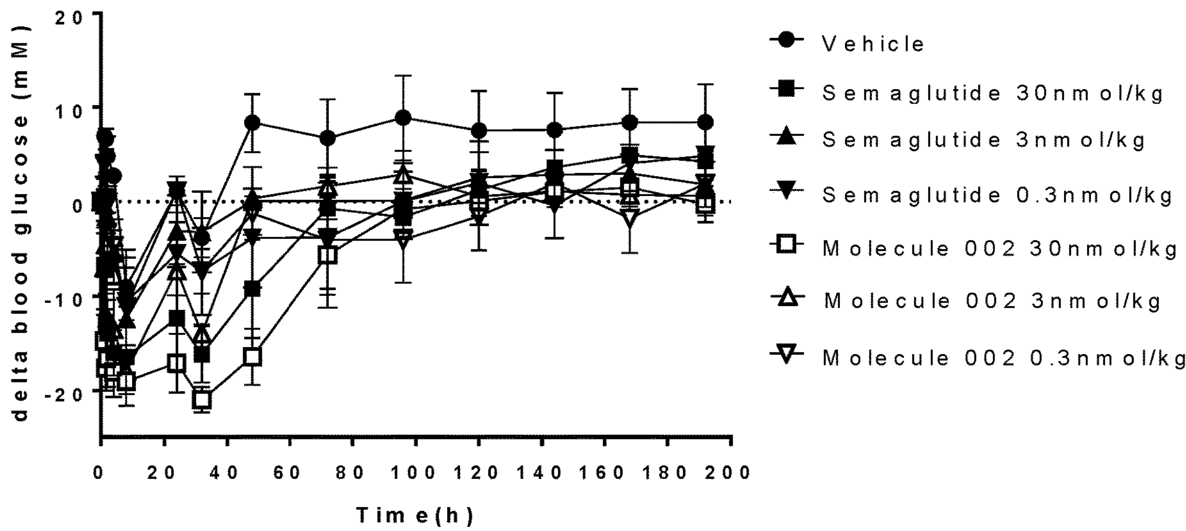

Conclusion: Both Molecules 001 and 002 showed dose dependent efficacy on glucose control (FIGS. 2A and 2B). Molecule 001 with double fatty acids exhibited more sustainable efficacy than semaglutide, suggesting Molecule 001 may have longer half-life.

Method: 10 weeks old male db/db mice were injected subcutaneously with GLP-1 polypeptide conjugate once. Non-Fasting glucose was measured on different times and five animals were used for each group. Delta blood glucose is glucose subtracted by baseline level. Data are indicated as mean values and standard error (SEM). The area under the curve for delta blood glucose from 0 until 192 hours (AUCΔBG 0-192h) was calculated.

Conclusion: Molecule 012 showed dose dependent efficacy on glucose control (FIGS. 2C, Table 4). Molecule 012 with double fatty acids exhibited more sustainable efficacy than semaglutide.

TABLE 4

The area under the curve for non-fasting delta blood glucose (%) from 0 until 192 hours (AUC ΔBG 0-192 h) in db/db mice for FIG. 2C.

| Group | AUC ΔBG 0-192 h (hr*mmol/L) |
|---|---|
| Semaglutide 3 nmol/kg | −317.0 |
| Semaglutide 10 nmol/kg | −583.4 |
| Semaglutide 30 nmol/kg | −527.1 |
| Molecule 012 3 nmol/kg | −424.5 |
| Molecule 012 10 nmol/kg | −1004.5 |
| Molecule 012 30 nmol/kg | −1447.0 |

Example 6b: In Vivo Activities in db/db Mice

Method: 10 week old male db/db mice were injected subcutaneously with Molecule 019 once. Random blood glucose was measured on different times and five animals were used for each group. Delta blood glucose is glucose subtracted by baseline level. Data are indicated as mean values and standard error (SEM).

Conclusion: Molecule 019 showed dose dependent efficacy on glucose control (FIGS. 2D and 2E) and significantly higher potency than semaglutide.

Example 7: Pharmacokinetic Measurement

Method: 6-8 week old male C57BL/6 mice were administrated in a single subcutaneous dose of 30 nmol/kg protein (n=3/group). Plasma samples were collected pre-dose (−5 min), 0.5 hr, 1 hr, 2 hr, 4 hr, 6 hr, 8 hr, 12 hr, 24 hr, 48 hr, 72 hr, 96 hr, 120 hr, 144 hr, 168 hr and 192 hr after the injection. The concentrations of GLP-1 polypeptide conjugates in the plasma were measured by ELISA assay. Based on the graph showing plasma concentration of each GLP-1 polypeptide conjugate versus time after subcutaneous injection, the pharmacokinetic parameters were calculated by WinNonlin.

Conclusion: Molecule 001 and 012 showed longer half-life than semaglutide and Molecule 002 in mouse (Table 5), consistent with in vivo efficacies.

TABLE 5

Pharmacokinetic parameters of GLP-1 polypeptide conjugates in mice. Pharmacokinetic data were analyzed by WinNonlin software. Tmax, Cmax, $T_{1/2}$, AUC were calculated for each molecule.

| PK parameters | Unit | Semaglutide | Molecule 001 | Molecule 002 | Molecule 012 |
|---|---|---|---|---|---|
| $T_{max}$ | hr | 6.7 | 32 | 4 | 24 |
| $C_{max}$ | nmol/L | 43.1 | 172.0 | 86.5 | 134 |
| Terminal $t_{1/2}$ | hr | 7.4 | 30.1 | 7.2 | 28.2 |
| $AUC_{tau}$ | hr*nmol/L | 614.7 (Tau = 24 h) | 12256 (Tau = 168 h) | 1507 (Tau = 48 h) | 7752 (tau = 192 h) |

Method: 6-8 weeks male SD rats were administrated in a single subcutaneous dose of 15 nmol/kg GLP-1 polypeptide conjugate (n=3/group) and a single intravenous dose of 15 nmol/kg GLP-1 polypeptide conjugate (n=3/group), respectively. Plasma samples were collected pre-dose (-5 min), 0.5 hr, 1 hr, 2 hr, 4 hr, 6 hr, 8 hr, 24 hr, 32 hr, 48 hr, 72 hr, 96 hr, 120 hr, 144 hr, 168 hr, 192 hr, 216 hr and 240 hr after subcutaneous administration. Plasma samples were collected pre-dose (-5 min), 0.083 hr, 0.25 hr, 0.5 hr, 1 hr, 2 hr, 4 hr, 6 hr, 8 hr, 24 hr, 32 hr, 48 hr, 72 hr, 96 hr and 120 hr after intravenous administration The concentrations of the polypeptide conjugates in the plasma were measured by LC-MS/MS method. Based on the graph showing plasma concentration of each polypeptide conjugate versus time after subcutaneous injection, the pharmacokinetic parameters were calculated by WinNonlin.

Conclusion: As shown in Table 6, Molecules 001 and 012 showed longer half-life than semaglutide, which was reported to have a $T_{1/2}$ of 12 hrs (s.c. administration, as reported in non-clinical reviews from FDA) in rat.

TABLE 6

Pharmacokinetic parameters of GLP-1 polypeptide conjugates in rats. Pharmacokinetic data were analyzed by WinNonlin software. Tmax, Cmax, $T_{1/2}$, AUC were calculated for each molecule.

| PK parameters | Unit | Molecule 001 i.v. | Molecule 001 s.c. | Molecule 012 i.v. | Molecule 012 s.c. |
|---|---|---|---|---|---|
| $T_{max}$ | hr | NA | 24 | NA | 26.7 |
| $C_{max}$ (C0 for iv) | nmol/L | 317 | 56.2 | 231 | 52.0 |
| Terminal $t_{1/2}$ | hr | 26.9 | 25.8 | 26.9 | 26.9 |
| $AUC_{tau}$ | hr*nmol/L | 4485 (Tau = 120 h) | 2887 (Tau = 192 h) | 4140 (Tau = 120 h) | 2954 (Tau = 192 h) |
| F | % | NA | 64 | NA | 71 |

NA: not available.

Method: 10-month old male Bama minipigs were administrated with a single subcutaneous dose of 5 nmol/kg GLP-1 polypeptide conjugate (n=2/group) and a single intravenous dose of 5 nmol/kg protein (n=2/group), respectively. Plasma samples for Molecule 012 and semaglutide group were collected pre-dose (−5 min), 0.5 hr, 1 hr, 3 hr, 8 hr, 24 hr, 48 hr, 72 hr, 96 hr, 168 hr, 336 hr, 504 hr and 672 hr after subcutaneous administration. Plasma samples for Molecule 012 and semaglutide group were collected pre-dose (−5 min), 0.083 hr, 0.5 hr, 1 hr, 3 hr, 8 hr, 24 hr, 48 hr, 72 hr, 96 hr, 168 hr, 336 hr and 504 hr after intravenous administration. For semaglutide group, the concentrations of GLP-1 polypeptide conjugates in the plasma were measured by ELISA assay. For Molecule 012 group, the concentrations of proteins in the plasma were measured by LC-MS/MS method. Based on the graph showing plasma concentration of each GLP-1 polypeptide conjugate versus time after administration, the pharmacokinetic parameters were calculated by WinNonlin.

Conclusion: Molecule 012 showed longer half-life than semaglutide in minipigs (Table 7)

TABLE 7

Pharmacokinetic parameters of GLP-1 polypeptide conjugates in minipigs. Pharmacokinetic data were analyzed by WinNonlin software. Tmax, Cmax, $T_{1/2}$, AUC were calculated for each molecule.

| PK parameters | Unit | Semaglutide i.v. | Semaglutide s.c. | Molecule 012 i.v. | Molecule 012 s.c. |
|---|---|---|---|---|---|
| $T_{max}$ | hr | NA | 16 | NA | 60 |
| $C_{max}$ (C0 for iv) | nmol/L | 188 | 54.9 | 236 | 71.4 |
| Terminal $t_{1/2}$ | hr | 53.0 | 62.8 | 136 | 147 |
| $AUC_{tau}$ | hr*nmol/L | 6643 (Tau = 336 h) | 5658 (Tau = 336 h) | 19617 (Tau = 504 h) | 16830 (Tau = 672 h) |
| F | % | NA | 85 | NA | 86 |

Example 8a: Efficacy Study in Disease Models

Selected molecules are assessed in disease animal models (such db/db mice) to determine body weight, food intake, glucose efficacy with dose responses in chronic studies. Some biomarkers are also measured, including fasting insulin, plasma triglyceride, cholesterol, liver triglyceride, and inflammatory biomarkers (ALT, AST and CRP).

Method: 22 week old DIO male C57BL/6 mice (~50 g) were injected once every other day (Q2D) subcutaneously with designated GLP-1 polypeptide conjugates (i.e., Molecule 012) for 25 days. Food intake and body weight were measured twice a week and fasting blood glucose was measured once a week. Five animals were used for each treatment group. Body weight and fasting blood glucose was monitored for each individual animal, but food intake for each group animals was measured together. Day 1 and Day 25 are first day and last day of molecule dosage. Data are indicated as mean values and standard error (SEM) or pooled values. Statistical analysis was performed by One-way ANOVA. Body weight reduction on Day 25 is calculated by −1*(% BW loss −% BW loss of vehicle group); Cumulative food intake reduction is calculated by −100*(cumulative food intake-cumulative food intake of vehicle)/cumulative food intake of vehicle.

Figure 3A:
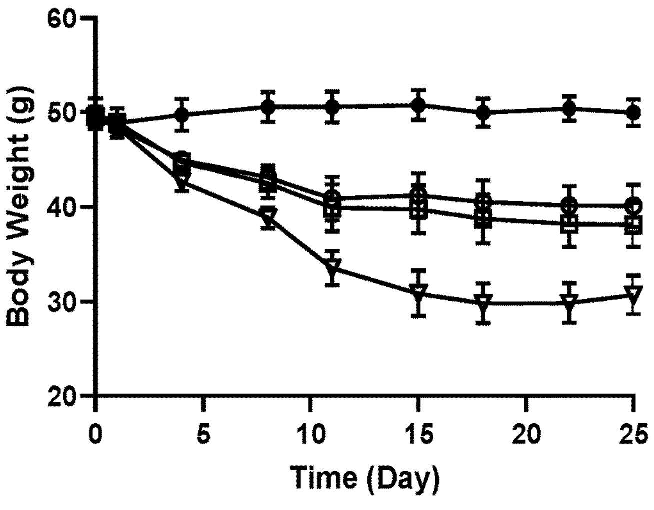
FIGS. 3A and 3B show in vivo efficacy in Diet Induced Obese (DIO) mice. To evaluate the effects of the respective GLP-1 polypeptide conjugates on body weight, food intake and glucose levels, 22-week old DIO mice (C57BL/6 mice on high fat diet for 13 weeks) were administered every other day subcutaneously with different concentrations of the designated GLP-1 polypeptide conjugates for 25 days.
Figure 3B:
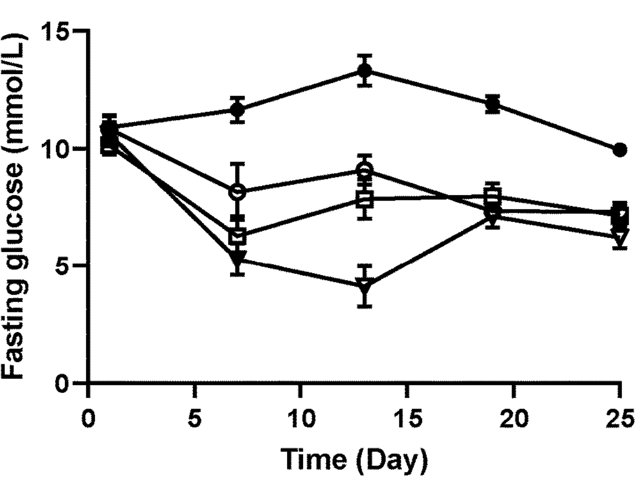

Conclusion: in DIO study, as shown in FIG. 3A, 3B and Table 8, Molecule 012 showed dose dependent efficacy on body weight reduction, food intake reduction and blood glucose control.

TABLE 8

Food intake and body weight reduction in DIO mice at Day 25

| Group | Cumulative food intake reduction (% reduction compared to vehicle) (Day 25) | Body weight reduction (% reduction compared to vehicle) (Day 25) |
|---|---|---|
| Molecule 012 10 nmol/kg, Q2D | 35 | 18.42 |
| Molecule 012 30 nmol/kg, Q2D | 37 | 23.0 |
| Molecule 012 100 nmol/kg, Q2D | 51 | 37.6 |

Example 8b: Efficacy Study in Disease Models

Selected molecules are assessed in Alzheimer' disease animal models (APP/PS1, APPswe/PSEN1dE9 mice) to determine cognitive function (Morris water maze and Y-maze), brain Aβ plaque deposition, and hippocampal pyramidal neuron number with dose responses in studies.

To assess the cognitive function of the animals, the Morris water maze and Y-maze tests were utilized. The effects of the molecules on beta-amyloid plaque deposition in the cortex and hippocampus, which are regions of the brain affected in Alzheimer's disease, were also measured. Furthermore, the number of pyramidal neurons in the hippocampus was assessed as a measure of the drug's potential neuroprotective effects. These methods allowed for a comprehensive evaluation of the efficacy of the molecules in mitigating the pathological changes associated with Alzheimer's disease in a preclinical setting.

Method: 6 months old APP/PS1 male mice were injected once day (QD) or once every other day (Q2D) subcutaneously with designated GLP-1 polypeptide conjugates (Molecule 012) for 10 weeks. 15 animals were used for each treatment group. Body weight and food intake was monitored every week. Cognitive function behavior experiments were conducted after dosing including Morris water maze and Y-maze. Brain tissue was taken for immunohistochemical staining to evaluate the Ap content in cortex and hippocampus. The number of hippocampal pyramidal neuron was measured by HE staining. Data are indicated as mean values and standard error (SEM). Statistical analysis was performed by One-way ANOVA. Semaglutide was used as a positive control.

Conclusion: in APP/PS1 study, as shown in FIGS. 5A, 5B, 5C, 5D and 5E, Molecule 012 showed dose dependent efficacy on cognitive function improvement, brain Ap plaque deposition reduction, and hippocampal pyramidal neuron protection. The molecule 012 was found to be effective in increasing quadrant occupancy, which refers to the percentage of time spent in the target quadrant during a navigation task, and increasing alternation percentage, which refers to the frequency of alternating between different locations during a maze task. Additionally, the molecule 012 was observed to reduce Ap plaque deposition in both the cortex and hippocampus regions of the brain, which are typically affected in Alzheimer's disease. The number of neurons in the hippocampus, a region critical for memory, was also improved by the molecule 012. These findings suggest that the molecule 012 has a positive impact on cognitive function and reduce the pathological changes associated with Alzheimer's disease. Molecule 012 showed significantly better efficacy than semaglutide in treating Alzheimer's disease in the animal studies.

Example 8c: Efficacy Study in Disease Models

Selected molecules are assessed in a Alzheimer' disease animal model for sporadic Alzheimer's dementia, which is the senescence-accelerated mouse prone 8 (SAMP8) model. SAMP8 mice exhibit age-related cognitive decline and neuropathological changes similar to those observed in human Alzheimer's disease, including beta-amyloid plaque deposition and neuroinflammation. They also display behavioral abnormalities and reduced synaptic plasticity.

7 months old SAMP8 mice were injected once every other day (Q2D) subcutaneously with designated GLP-1 polypeptide conjugates (Molecule 012) for 16 weeks, at 30 nmol/kg, 100 nmol/kg and 300 nmol/kg, respectively. 15 animals were used for each treatment group. Body weight and food intake was monitored every week. Cognitive function behavior experiments were conducted after dosing including Morris water maze and Y-maze. Brain tissue was taken for immunohistochemical staining to evaluate the Ap content in cortex and hippocampus. The number of hippocampal pyramidal neuron was measured by HE staining. Data are indicated as mean values and standard error (SEM). Statistical analysis was performed by One-way ANOVA. Semaglutide and Donepezil were used as positive controls.

Molecule 012 shows dose dependent efficacy on cognitive function improvement, brain Aβ plaque deposition reduction, and hippocampal pyramidal neuron protection in SAMP8 mice. Molecule 012 also shows significantly better efficacy than the positive controls in treating Alzheimer's disease in SAMP8 mice.

Example 9a: PK Study in Non-Human Primates

Pharmacokinetics of selected molecules are assessed in monkeys. Both subcutaneous and intravenous injections are performed.

Method: 3-5 years old male cynomolgus monkeys were administrated in a single subcutaneous dose of 5 nmol/kg GLP-1 polypeptide conjugate (n=2/group). Plasma samples for semaglutide group were collected pre-dose (-5 min), 2 hr, 4 hr, 6 hr, 8 hr, 24 hr, 48 hr, 72 hr, 96 hr, 120 hr, 144 hr, 216 hr, 288 hr, 360 hr, 432 hr and 504 hr after the injection. Plasma samples for Molecule 012 group were collected pre-dose (-5 min), 0.5 hr, 1 hr, 2 hr, 4 hr, 6 hr, 8 hr, 24 hr, 48 hr, 96 hr, 120 hr, 144 hr, 168 hr, 192 hr, 216 hr, 288 hr, 432 hr and 504 hr after the injection. For semaglutide group, the concentrations of proteins in the plasma were measured by ELISA assay. For Molecule 012 group, the concentrations of GLP-1 polypeptide conjugates in the plasma were measured by LC-MS/MS method. Based on the graph showing plasma concentration of each protein versus time after subcutaneous injection, the pharmacokinetic parameters were calculated by WinNonlin.

Conclusion: Molecule 012 showed longer half-life than semaglutide and Molecule 002 in monkey (Table 9a)

TABLE 9a

Pharmacokinetic parameters of GLP-1 polypeptide conjugates in cynomolgus monkeys. Pharmacokinetic data were analyzed by WinNonlin software. Tmax, Cmax, $T_{1/2}$, AUC were calculated for each molecule.

| PK parameters | Unit | Semaglutide | Molecule 012 |
|---|---|---|---|
| $T_{max}$ | hr | 7 | 24 |
| $C_{max}$ | nmol/L | 48.1 | 58.0 |
| Terminal $t_{1/2}$ | hr | 65 | 122 |
| $AUC_{tau}$ | hr*nmol/L | 2876<br>(Tau = 96 h) | 10989<br>(Tau = 504 h) |

Example 9b: PK Study in Non-Human Primates

Method: 3-5 years old male cynomolgus monkeys were administrated in a single intravenous dose of 4 nmol/kg and 5 nmol/kg for semaglutide and Molecule 019 (n=2/group), respectively. Plasma samples for semaglutide group were collected pre-dose (-5 min), 0.083 hr, 1 hr, 2 hr, 4 hr, 8 hr, 24 hr, 36 hr, 48 hr, 72 hr, 96 hr, 120 hr, 144 hr, and 168 hr after the injection. Plasma samples for Molecule 012 group were collected pre-dose (-5 min), 0.083 hr, 0.25 hr, 0.5 hr, 1 hr, 2 hr, 4 hr, 8 hr, 12 hr, 24 hr, 36 hr, 48 hr, 72 hr, 96 hr, 120 hr, 144 hr, and 168 hr after the injection. The concentrations of proteins in the plasma were measured by LC-MS/MS method. Based on the graph showing plasma concentration of each protein versus time after intravenous administration, the pharmacokinetic parameters were calculated by WinNonlin.

Conclusion: Molecule 019 showed similar half-life with semaglutide in monkeys (Table 9b), which potentially supports once weekly dosing in human. Further in view of the potent GLP-1 activity (10-fold higher than semaglutide) of Molecule 019, it is expected that Molecule 019 is a promising candidate that not only provides better efficacy than semaglutide but also supports a desirable once-weekly dosing frequency (or potentially even less frequent).

TABLE 9b

Pharmacokinetic parameters of GLP-1 polypeptide conjugates in cynomolgus monkeys. Pharmacokinetic data were analyzed by WinNonlin software. $C_0$, $T_{1/2}$ and AUC were calculated for each molecule.

| PK parameters | Unit | Semaglutide | Molecule 019 |
|---|---|---|---|
| $C_0$ | nmol/L | 85.1 | 176.5 |
| Vz | L/kg | 0.09 | 0.06 |
| Cl | mL/min/kg | 0.026 | 0.015 |
| Terminal $t_{1/2}$ | hr | 42.8 | 49.0 |
| $AUC_{tau}$ | hr*nmol/L | 2402 (t = 168 hr) | 5302 (t = 168 hr) |

Example 10: Immunogenicity Assessment

Selected GLP-1 polypeptide conjugates are also assessed for immunogenicity by in silico (iTope and TCED methods) and ex vivo (EpiScreen) methods.

Example 11: Human Serum Albumin Binding

Method: Binding of molecules to serum albumin was characterized by surface plasmon resonance in a Biacore 8K instrument. Serum albumin from different species was covalently bound to CM5 sensor chips surface until 4000 RU was reached. The chip was blocked by 1M ethanolamine with flowrate of 10 μL/min for 420 s. Each molecule sample was diluted and injected at a flow rate of 30 μL/min to allow for binding to chip-bound albumin for 120 s and for dissociation for 300 s. Binding buffer without molecule was sent over the chip at the flow rate of 20 seconds to allow spontaneous dissociation of bound molecule for 30 seconds.

Conclusion: Molecules 004, 001, 006 and 012 showed higher binding affinity of human serum albumin (see Table 10) than semaglutide, Molecule 019 and Molecule 002 which is consistent with the PK data.

TABLE 10

Human serum albumin binding affinity

| | KD (μM) | Rmax (RU) |
|---|---|---|
| Semaglutide | 2.82 | 55.2 |
| Molecule 004 | 0.716 | 546.0 |
| Molecule 001 | 0.697 | 498.3 |
| Molecule 006 | 0.746 | 398.6 |
| Molecule 012 | 0.376 | 207.3 |
| Molecule 002 | 9.11 | 307.8 |
| Molecule 019 | 10.1 | 146.3 |

Example 12: Preparation of Tablet Composition

Method:

Spray dried compounds preparation: The GLP-1 polypeptide conjugates can be prepared according to the methods described in Example 1, 2 and 3 as provided herein, followed by buffer exchanging to 50-70% w/w ethanol using reverse phase C4 column. The spray dried GLP-1 polypeptide conjugates were obtained by feeding the solution into spray dryers.

Dry granulation: Dry granulation was performed by roller compaction with a roller speed at 6-10 rpm and roller compaction force at 25-55 bar with a gap of 0.6-1.0 mm. The comminution speed is set at 100-150 rpm followed by a mesh 0.5-1.5 mm screen. Prior to dry granulation, the compositions are blended using blender Kai chuang tong he KCLD-10 mixer.

Tablet compression: The tablets are compressed on a standard compression rotary tablet press with a press speed at 10-20 rpm. The compression forces is set at 6-15 kg. Precompression was performed before the main compression to remove the entrapped air.

Test composition A1 and B1: The SNAC, Magnesium stearate and MCC were blended prior to dry granulation. The obtained granules were called SNAC granules. GLP-1 polypeptide conjugates (i.e. Molecule 012 or Molecule 019), povidone and MCC were blended prior to dry granulation. The obtained granules were called GLP-1 granules. Then the SNAC granules and GLP-1 granules were blended with additional Magnesium stearate and then compressed into tablets.

Test composition A2: The SNAC, Magnesium stearate and MCC were blended prior to dry granulation. The obtained granules (called SNAC granules) were blended with GLP-1 polypeptide conjugate and additional Magnesium stearate prior to tablet compression.

Test composition A3, A5-A17, A19 B2-B14, B17-B21: The SNAC, Magnesium stearate were blended prior to dry granulation. The obtained granules (called SNAC granules) were blended with GLP-1 polypeptide conjugate and with additional Magnesium stearate prior to tablet compression.

Test composition A4 and A18, B15 and B16: The SNAG, Magnesium stearate and GLP-1 polypeptide conjugate were blended prior to dry granulation. The obtained granules subsequently subjected to tablet compression.

Tables 11A and 11B respectively summarize the different embodiments of the pharmaceutical composition for Molecule 012 (Table 11A) and Molecule 019 (Table 11B).

TABLE 11A

Composition of Molecule 012 Tablets

| Composition | Test A1 Tablet (mg) | Test A1 Proportion (%) | Test A2 Tablet (mg) | Test A2 Proportion (%) | Test A3 Tablet (mg) | Test A3 Proportion (%) |
|---|---|---|---|---|---|---|
| SNAC | 300 | 67 | 300 | 72.0 | 300 | 83.4 |
| Magnesium stearate | 9.7 (7.7*) | 2.2 | 9.7 (7.7*) | 2.3 | 9.7 (7.7*) | 2.7 |
| MCC | 80 (57*) | 17.8 | 57 | 13.7 | / | / |
| Molecule 012 | 50 | 11.2 | 50 | 12.0 | 50 | 13.9 |
| Povidone | 8 | 1.8 | / | 1 | 1 | / |
| Total | 447.7 | 100 | 414.7 | 100 | 359.7 | 100 |

| Composition | Test A4 Tablet (mg) | Test A4 Proportion (%) | Test A5 Tablet (mg) | Test A5 Proportion (%) | Test A6 Tablet (mg) | Test A6 Proportion (%) |
|---|---|---|---|---|---|---|
| SNAC | 300 | 83.9 | 250 | 80.7 | 100 | 62.6 |
| Magnesium stearate | 7.7 (7.7*) | 2.2 | 9.7 (6.4*) | 3.1 | 9.7 (2.6*) | 6.1 |
| Molecule 012 | 50 | 13.9 | 50 | 16.2 | 50 | 31.3 |
| Total | 357.7 | 100 | 309.7 | 100 | 159.7 | 100 |

| Composition | Test A7 Tablet (mg) | Test A7 Proportion (%) | Test A8 Tablet (mg) | Test A8 Proportion (%) | Test A9 Tablet (mg) | Test A9 Proportion (%) |
|---|---|---|---|---|---|---|
| SNAC | 500 | 88.8 | 100 | 80.7 | 250 | 90.5 |
| Magnesium stearate | 12.8 (12.8*) | 2.3 | 3.9 (2.6*) | 3.1 | 6.4 (6.4*) | 2.3 |
| Molecule 012 | 50 | 8.9 | 20 | 16.2 | 20 | 7.2 |
| Total | 562.8 | 100 | 123.9 | 100 | 276.4 | 100 |

| Composition | Test A10 Tablet (mg) | Test A10 Proportion (%) | Test A11 Tablet (mg) | Test A11 Proportion (%) | Test A12 Tablet (mg) | Test A12 Proportion (%) |
|---|---|---|---|---|---|---|
| SNAC | 500 | 93.8 | 100 | 88.8 | 250 | 93.8 |
| Magnesium stearate | 12.8 (12.8*) | 2.4 | 2.6 (2.6*) | 2.3 | 6.4 (6.4*) | 2.4 |
| Molecule 012 | 20 | 3.8 | 10 | 8.9 | 10 | 3.8 |
| Total | 532.8 | 100 | 112.6 | 100 | 266.4 | 100 |

| Composition | Test A13 Tablet (mg) | Test A13 Proportion (%) | Test A14 Tablet (mg) | Test A14 Proportion (%) | Test A15 Tablet (mg) | Test A15 Proportion (%) |
|---|---|---|---|---|---|---|
| SNAC | 500 | 95.6 | 100 | 45.6 | 250 | 67.7 |
| Magnesium stearate | 12.8 (12.8*) | 2.4 | 19.4 (2.6*) | 8.8 | 19.4 (6.4*) | 5.2 |
| Molecule 012 | 10 | 1.9 | 100 | 45.6 | 100 | 27.1 |
| Total | 522.8 | 100 | 219.4 | 100 | 369.4 | 100 |

| Composition | Test A16 Tablet (mg) | Test A16 Proportion (%) | Test A17 Tablet (mg) | Test A17 Proportion (%) | Test A18 Tablet (mg) | Test A18 Proportion (%) |
|---|---|---|---|---|---|---|
| SNAC | 500 | 80.7 | 50 | 80.6 | 100 | 81.6 |
| Magnesium stearate | 19.4 (12.8*) | 3.1 | 2 (1.3*) | 3.2 | 2.6 (2.6*) | 2.1 |
| Molecule 012 | 100 | 16.2 | 10 | 16.2 | 20 | 16.3 |
| Total | 619.4 | 100 | 62 | 100 | 122.6 | 100 |

TABLE 11A-continued

| Composition of Molecule 012 Tablets | | |
|---|---|---|
| | Test A19 | |
| Composition | Tablet (mg) | Proportion (%) |
| SNAC | 300 | 86.3 |
| Magnesium stearate | 7.7 (7.7*) | 2.2 |
| Molecule 012 | 40 | 11.5 |
| Total | 347.7 | 100 |

Note:
*the amounts included in the SNAC granules

TABLE 11B

| Composition of Molecule 019 Tablets | | | | | | |
|---|---|---|---|---|---|---|
| | Test B1 | | Test B2 | | Test B3 | |
| Composition | Tablet (mg) | Proportion (%) | Tablet (mg) | Proportion (%) | Tablet (mg) | Proportion (%) |
| SNAC | 300 | 74.5 | 100 | 93.0 | 100 | 96.5 |
| Magnesium stearate | 9.7 (7.7*) | 2.4 | 2.6 (2.6*) | 2.4 | 2.6 (2.6*) | 2.5 |
| MCC | 80 (57*) | 19.9 | / | / | / | / |
| Molecule 019 | 5 | 1.2 | 5 | 4.6 | 1.0 | 1.0 |
| Povidone | 8 | 2.0 | / | / | / | / |
| Total | 402.7 | 100.0 | 107.6 | 100 | 103.6 | 100 |
| | Test B4 | | Test B5 | | Test B6 | |
| Composition | Tablet (mg) | Proportion (%) | Tablet (mg) | Proportion (%) | Tablet (mg) | Proportion (%) |
| SNAC | 100 | 95.1 | 100 | 88.8 | 100 | 80.7 |
| Magnesium stearate | 2.6 (2.6*) | 2.5 | 2.6 (2.6*) | 2.3 | 3.9 (2.6*) | 3.1 |
| Molecule 019 | 2.5 | 2.4 | 10 | 8.9 | 20 | 16.2 |
| Total | 105.1 | 100 | 112.6 | 100 | 123.9 | 100 |
| | Test B7 | | Test B8 | | Test B9 | |
| Composition | Tablet (mg) | Proportion (%) | Tablet (mg) | Proportion (%) | Tablet (mg) | Proportion (%) |
| SNAC | 100 | 62.6 | 300 | 95.9 | 300 | 91.5 |
| Magnesium stearate | 9.7 (2.6*) | 6.1 | 7.7 (7.7*) | 2.5 | 7.7 (7.7*) | 2.4 |
| Molecule 019 | 50 | 31.3 | 5 | 1.6 | 20 | 6.1 |
| Total | 159.7 | 100 | 312.7 | 100 | 327.7 | 100 |
| | Test B10 | | Test B11 | | Test B12 | |
| Composition | Tablet (mg) | Proportion (%) | Tablet (mg) | Proportion (%) | Tablet (mg) | Proportion (%) |
| SNAC | 300 | 83.4 | 50 | 88.8 | 50 | 95.6 |
| Magnesium stearate | 9.7 (7.7*) | 2.7 | 1.3 (1.3*) | 2.3 | 1.3 (1.3*) | 2.5 |
| Molecule 019 | 50 | 13.9 | 5 | 8.9 | 1 | 1.9 |
| Total | 359.7 | 100 | 56.3 | 100 | 52.3 | 100 |

TABLE 11B-continued

Composition of Molecule 019 Tablets

| Composition | Test B13 Tablet (mg) | Test B13 Proportion (%) | Test B14 Tablet (mg) | Test B14 Proportion (%) | Test B15 Tablet (mg) | Test B15 Proportion (%) |
|---|---|---|---|---|---|---|
| SNAC | 50 | 92.9 | 50 | 80.7 | 100 | 93.0 |
| Magnesium stearate | 1.3 (1.3*) | 2.4 | 2.0 (1.3*) | 3.2 | 2.6 (2.6*) | 2.4 |
| Molecule 019 | 2.5 | 4.7 | 10 | 16.1 | 5 | 4.6 |
| Total | 53.8 | 100 | 62.0 | 100 | 107.6 | 100 |

| Composition | Test B16 Tablet (mg) | Test B16 Proportion (%) | Test B17 Tablet (mg) | Test B17 Proportion (%) | Test B18 Tablet (mg) | Test B18 Proportion (%) |
|---|---|---|---|---|---|---|
| SNAC | 300 | 83.9 | 300 | 97.2 | 300 | 94.4 |
| Magnesium stearate | 7.7 (7.7*) | 2.2 | 7.7 (7.7*) | 2.5 | 7.7 (7.7*) | 2.4 |
| Molecule 019 | 50 | 13.9 | 1 | 0.3 | 10 | 3.2 |
| Total | 357.7 | 100 | 308.7 | 100.00 | 317.7 | 100 |

| Composition | Test B19 Tablet (mg) | Test B19 Proportion (%) | Test B20 Tablet (mg) | Test B20 Proportion (%) | Test B21 Tablet (mg) | Test B21 Proportion (%) |
|---|---|---|---|---|---|---|
| SNAC | 200 | 93.0 | 200 | 88.8 | 200 | 85.1 |
| Magnesium stearate | 5.1 (5.1*) | 2.4 | 5.1 (5.1*) | 2.3 | 5.1 (5.1*) | 2.2 |
| Molecule 019 | 10 | 4.6 | 20 | 8.9 | 30 | 12.8 |
| Total | 215.1 | 100 | 225.1 | 100 | 235.1 | 100 |

Note:
*the amounts included in the SNAC granules

Example 13: Disintegration Test

Method: The standard disintegration test were performed using TDTF ZB-3A disintegration apparatus according to the Chinese Pharmacopeia 2020. There are 2 basket racks containing 6 tubes for each basket in the disintegration apparatus. The tablets were placed in the tubes and the disintegration was monitored automatically by the camera on the top of the basket. The basket is immersed in the beaker containing 800 mL purified water at 37° C. Time for complete disintegration was measured. The results are reported as an average of 3 tablets. Table 3 shows the results for the test compositions described in Example 12.

Conclusion: For the Molecule 012, the test compositions A3, A5, A8, A9, A11, A12, A17 and A18 exhibited significantly faster disintegration than test composition A1, A2, A7, A10, A13 and A16 (see Table 12A). For the Molecule 019, the test compositions B2-B6, B8-B16, B18 and B19 displayed significantly faster disintegration than test composition B1 (see Table 12B).

TABLE 12A

Disintegration Tests for Molecule 012 Compositions

| Composition | Test A1 | Test A2 | Test A3 | Test A5 | Test A7 |
|---|---|---|---|---|---|
| Disintegration time | 10 min 40 s | 11 min 30 s | 8 min 30 s | 9 min 30 s | 15 min 36 s |
| **Composition** | **Test A8** | **Test A9** | **Test A10** | **Test A11** | **Test A12** |
| Disintegration time | 6 min 30 s | 8 min 40 s | 14 min 40 s | 5 min 30 s | 7 min 20 s |
| **Composition** | **Test A13** | **Test A16** | **Test A17** | **Test A18** | **Test A19** |
| Disintegration time | 14 min 30 s | 20 min 04 s | 5 min 50 s | 7 min 30 s | 9 min 32 s |

TABLE 12B

| Disintegration Tests for Molecule 019 Compositions | | | | | | |
|---|---|---|---|---|---|---|
| Composition | Test B1 | Test B2 | Test B3 | Test B4 | Test B5 | Test B6 |
| Disintegration time | 13 min 14 s | 5 min 08 s | 4 min 52 s | 4 min 53 s | 5 min 56 s | 6 min 12 s |
| Composition | Test B8 | Test B9 | Test B10 | Test B11 | Test B12 | Test B13 |
| Disintegration time | 7 min 52s | 8 min 14 s | 9 min 45 s | 3 min 52 s | 3 min 49 s | 4 min 05 s |
| Composition | Test B14 | Test B15 | Test B16 | Test B18 | Test B19 | |
| Disintegration time | 4 min 04 s | 5 min 24 s | 10 min 40 s | 9 min 06s | 8 min 26s | |

Example 14. Dissolution Testing

Method: The dissolution test was performed using Hanson ELITE 8 dissolution apparatus in accordance with Chinese Pharmacopoeia 2020. The 500 mL medium of phosphate buffer with pH 6.8 containing 0.05% Brij 35 was used at 37° C. The paddle rotation speed was set at 70 rpm. The samples were collected at predefined intervals. The GLP-1 and SNAG concentration were determined using RP-UPL methods with UV detection at 215 nm and 335 nm, respectively.

Figure 4A:
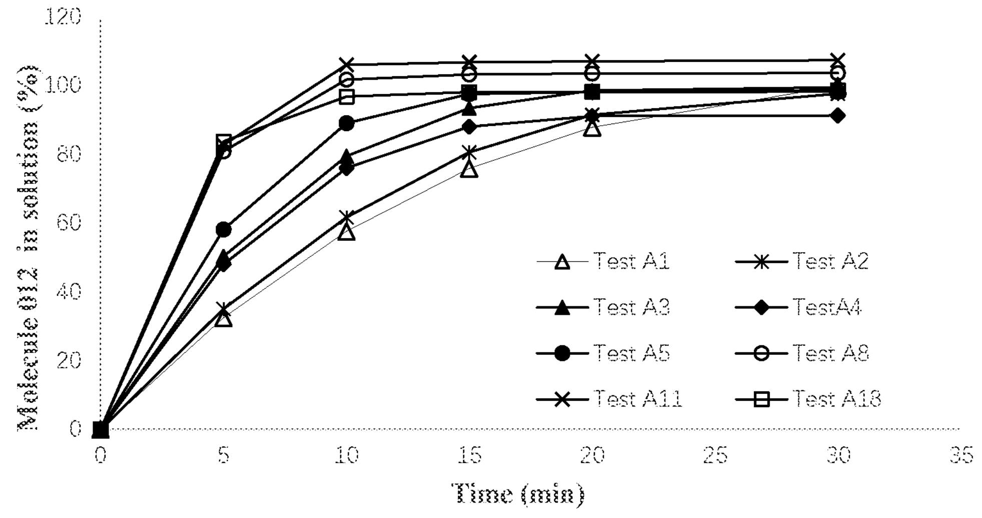
FIGS. 4A-4D respectively how the dissolution profiles of the GLP-1 (FIG. 4A) and SNAC (FIG. 4B) of different pharmaceutical compositions for Molecule 012.
Figure 4B:
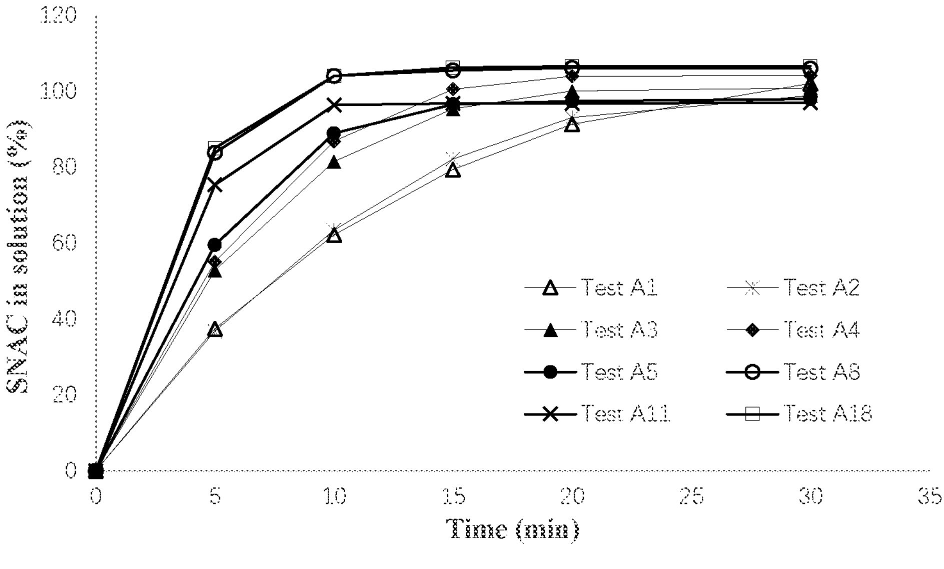
Figures 4C, 4D:
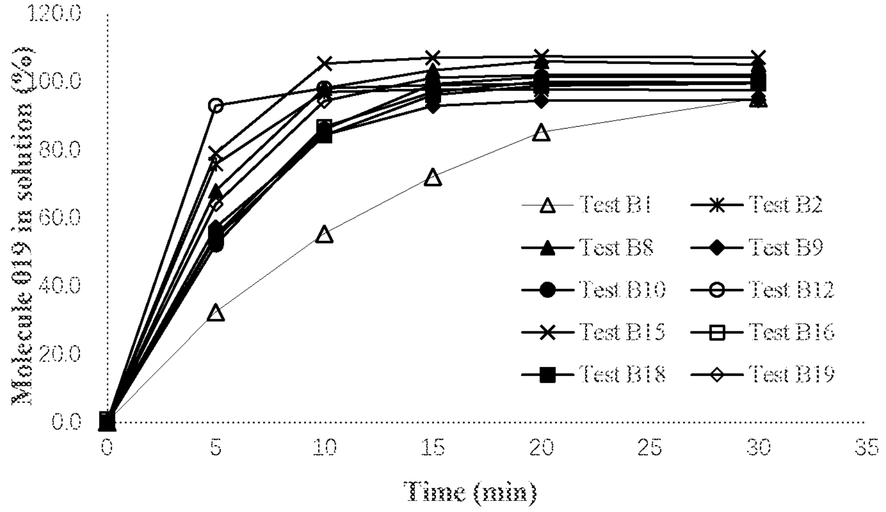
Figure 5A:
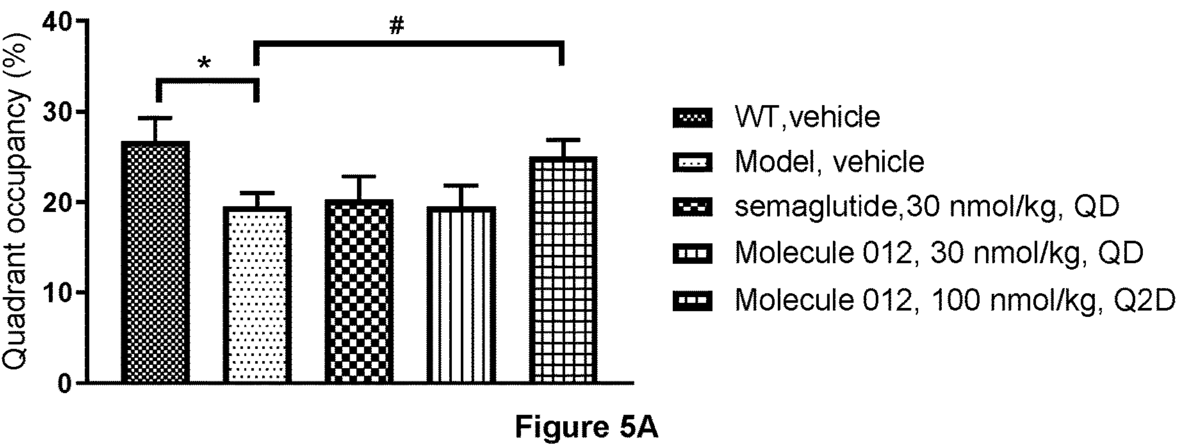
FIGS. 5A-5E show in vivo efficacy in Alzheimer' disease (APP/PS1, APPswe/PSEN1dE9) mice. To evaluate the effects of the respective GLP-1 polypeptide conjugates on cognitive function (Morris water maze and Y-maze), brain Aβ plaque deposition, and hippocampal pyramidal neuron number, 6 months old APP/PS1 male mice were administered once day (QD) or every other day (Q2D) subcutaneously with different concentrations of the designated GLP-1 polypeptide conjugate (Molecule 012) for 10 weeks.
Figure 5B:
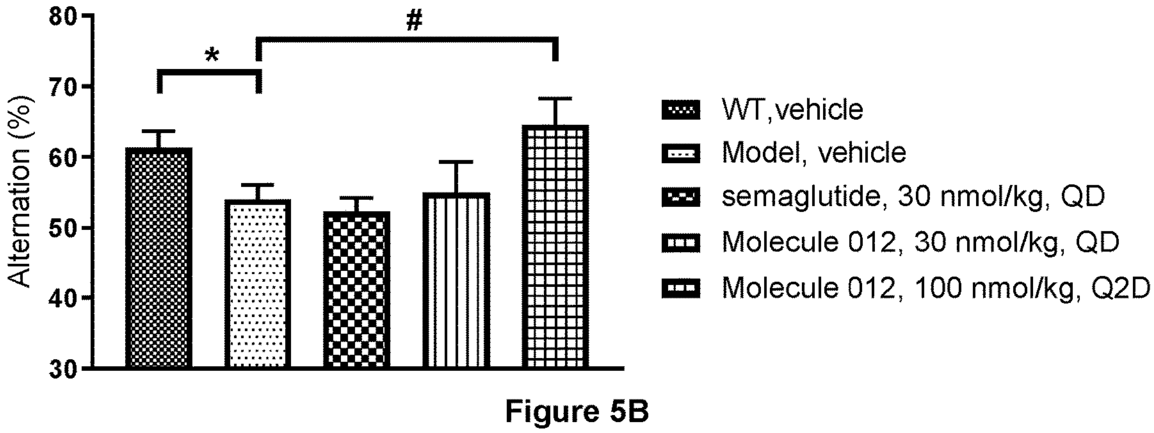
Figure 5C:
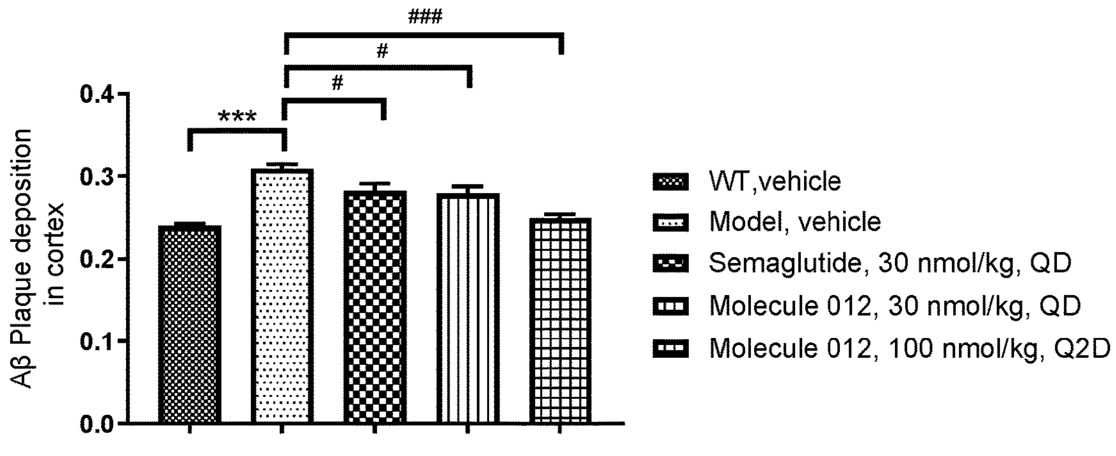
Figure 5D:
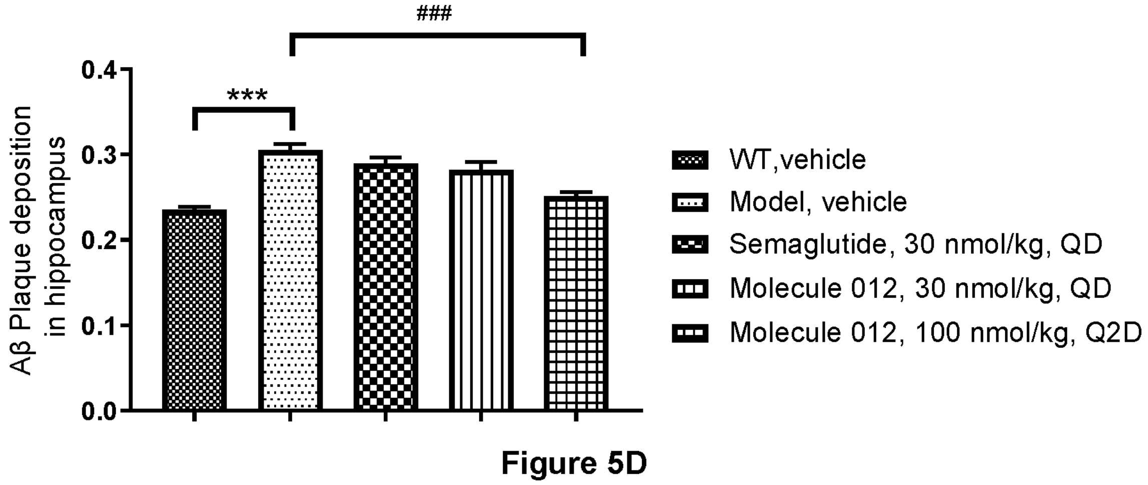
Figure 5E:
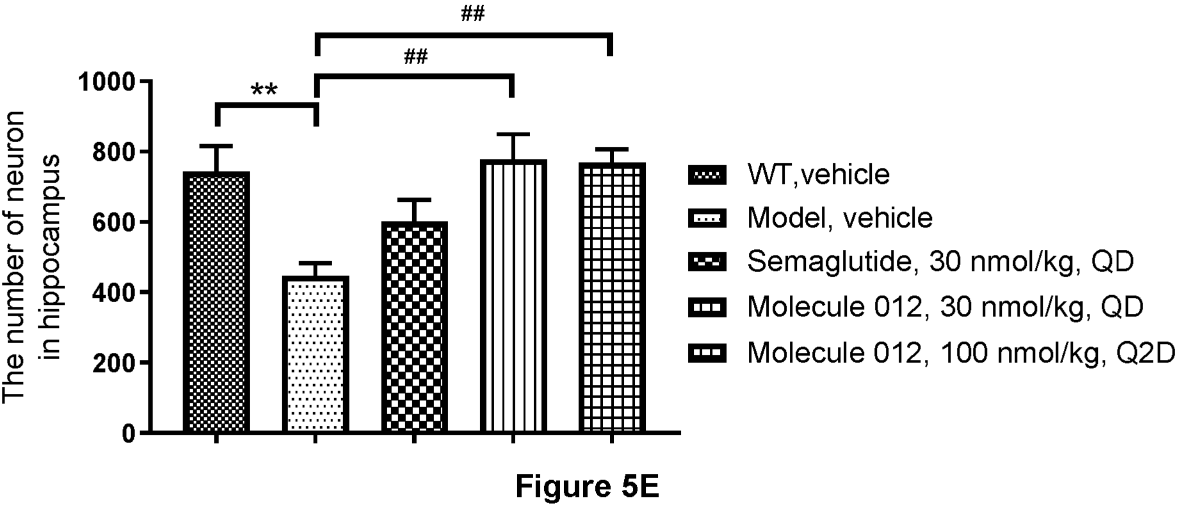

Conclusion: For the Molecule 012, the test composition A3, A4, A, A8, A11, A18 and A19 showed significantly faster release of Molecule 012 and SNAG compared to test composition A1 and A2 (see Table 13A and FIGS. 4A and 4B). For the Molecule 019, all the test composition B2, B8, B9, B10, B12, B15, B16, B18 and B19 showed significantly faster release of Molecule 019 and SNAG compared to test composition B (see Table 13B and FIGS. 48 and 4D).

TABLE 13A

| GLP-1 polypeptide conjugate and SNAC in solution (%) | | | | | |
|---|---|---|---|---|---|
| | SNAC | Molecule 012 | Molecule 012 in solution (%) | | |
| Composition | (mg) | (mg) | 5 min | 15 min | 30 min |
| Test A1 | 300 | 50 | 32.4 | 75.8 | full release |
| Test A2 | 300 | 50 | 35.0 | 80.6 | full release |
| Test A3 | 300 | 50 | 50.3 | 93.4 | full release |
| Test A4 | 300 | 50 | 48.0 | 88.0 | full release |
| Test A5 | 250 | 50 | 58.1 | 97.5 | full release |
| Test A8 | 100 | 20 | 80.8 | full release | full release |
| Test A11 | 100 | 10 | 82.7 | full release | full release |
| Test A18 | 100 | 20 | 83.7 | full release | full release |
| Test A19 | 300 | 40 | 42.9 | 88.8 | full release |
| | SNAC | Molecule 012 | SNAC in solution (%) | | |
| Composition | (mg) | (mg) | 5 min | 15 min | 30 min |
| Test A1 | 300 | 50 | 37.4 | 79.3 | full release |
| Test A2 | 300 | 50 | 36.8 | 82.1 | full release |
| Test A3 | 300 | 50 | 52.8 | 95.3 | full release |
| Test A4 | 300 | 50 | 55.1 | full release | full release |
| Test A5 | 250 | 50 | 59.5 | 96.5 | full release |
| Test A8 | 100 | 20 | 83.8 | full release | full release |
| Test A11 | 100 | 10 | 75.3 | full release | full release |
| Test A18 | 100 | 20 | 85.0 | full release | full release |
| Test A19 | 300 | 40 | 46.7 | 92.6 | full release |

TABLE 13B

| GLP-1 polypeptide conjugate and SNAC in solution (%) | | | | | |
|---|---|---|---|---|---|
| | SNAC | Molecule 019 | Molecule 019 in solution (%) | | |
| Composition | (mg) | (mg) | 5 min | 15 min | 30 min |
| Test B1 | 300 | 5 | 32.3 | 72.1 | full release |
| Test B2 | 100 | 5 | 75.8 | full release | full release |
| Test B8 | 300 | 5 | 68.0 | full release | full release |
| Test B9 | 300 | 20 | 57.3 | full release | full release |
| Test B10 | 300 | 50 | 52.2 | 99.2 | full release |
| Test B12 | 50 | 1 | 93.0 | 99.0 | full release |
| Test B15 | 100 | 5 | 79.0 | full release | full release |
| Test B16 | 300 | 50 | 54.9 | 96.9 | full release |
| Test B18 | 300 | 10 | 54.2 | 96.1 | full release |
| Test B19 | 200 | 10 | 64.0 | full release | full release |

TABLE 13B-continued

| GLP-1 polypeptide conjugate and SNAC in solution (%) | | | | | |
|---|---|---|---|---|---|
| | SNAC | Molecule 019 | SNAC in solution (%) | | |
| Composition | (mg) | (mg) | 5 min | 15 min | 30 min |
| Test B1 | 300 | 5 | 38.7 | 78.7 | full release |
| Test B2 | 100 | 5 | 79.0 | full release | full release |
| Test B8 | 300 | 5 | 66.4 | full release | full release |
| Test B9 | 300 | 20 | 62.2 | full release | full release |
| Test B10 | 300 | 50 | 51.6 | 94.1 | full release |
| Test B12 | 50 | 1 | full release | full release | full release |
| Test B15 | 100 | 5 | 78.5 | full release | full release |
| Test B16 | 300 | 50 | 57.6 | 98.4 | full release |
| Test B18 | 300 | 10 | 53.8 | 94.1 | full release |
| Test B19 | 200 | 10 | 63.3 | 98.7 | full release |

Example 15. Oral Exposure in Beagle Dogs

Method: Male beagle dogs (N=4, 1-5 years, weight 7.5-15 kg) were fasted overnight before dosing and from 0 to 4 h after dosing. The dogs are restricted to water 1 hour before dosing until 4 hours after dosing, otherwise have ad libitum access to water. The test compositions as provided in Tables 11A and 11B were peroral (p.o.) administrated to dogs. Blood samples were taken at predefined time points: pre-dose (-5 min) 0.25 hr, 0.5 hr, 0.75 hr, 1 hr, 1.5 hr, 2 hr, 2.5 hr, 3 hr, 4 hr, 6 hr, 8 hr, 12 hr and 24 hr post dose. The blood samples were collected into the tubes containing EDTA and kept on ice. Then the plasma was isolated from whole blood by centrifugation and stored at −20° C. The concentrations of GLP-1 polypeptide conjugate in the plasma were measured by LC-MS/MS method. Individual plasma concentration-time profiles were analyzed by a non-compartmental model in WinNonlin v. 6.3 or Phoenix v.6.2 (Pharsight Inc., Mountain View, CA, USA). The GLP-1 polypeptide conjugate exposure measured at t=30 min was determined and normalized by (dose/kg body weight). The area under the plasma concentration versus time curve for the first 30 min (AUC, [time×concentration]) was calculated (by the Pharsight programme) after oral administration and normalized by ((dose/kg body weight)×100) to obtain the dose corrected exposure. The average values obtained are provided in Table 14A, and all values are expressed as geometric means.

Conclusion: As shown in Table 14A for Molecule 012, the test composition A8 showed almost 4-fold increase in exposure during the first 30 min compared to test composition A1. The test composition A19 showed 8-fold increase in exposure during the first 30 min compared to test composition A1.

For Molecule 019, the test composition B2 and B8 also showed significant increase in exposure during the first 30 min compared to test composition B1 (data not shown), which is similar to the trend observed in dissolution and disintegration test results shown in Examples 13 and 14. As shown in Table 14B, the test composition B2 and B8 showed a dose corrected AUC 0-30 min of about 0.772 and 0.600 (nmol/L x h)/(nmol/kg)×100, respectively, which demonstrated a very good oral absorption profile. All the test compositions B2-B18 are useful for Molecule 019 and can provide a better oral absorption profile than the reference composition B1.

TABLE 14A

| Average exposure in beagle dogs after oral administration of tested compositions. | | | | |
|---|---|---|---|---|
| Composition | SNAC mg/ GLP-1 mg | Dose corrected AUC 0-30 min (nmol/L × h)/ (nmol/kg) × 100 | dose corrected exposure t = 30 min (nmol/L)/ (nmol/kg) | No. of dog |
| Test A1 | 300/50 | 0.046 | 0.002 | 3 |
| Test A8 | 100/20 | 0.182 | 0.005 | 4 |
| Test A19 | 300/40 | 0.371 | 0.019 | 5 |

TABLE 14B

| Average exposure in beagle dogs after oral administration of tested compositions. | | | | |
|---|---|---|---|---|
| Composition | SNAC mg/ GLP-1 mg | Dose corrected AUC 0-30 min (nmol/L × h)/ (nmol/kg) × 100 | dose corrected exposure t = 30 min (nmol/L)/ (nmol/kg) | No. of dog |
| Test B2 | 100/5 | 0.772 | 0.031 | 10 |
| Test B8 | 300/5 | 0.600 | 0.033 | 5 |

The invention claimed is:

1. A pharmaceutical composition comprising a polypeptide conjugate and an absorption enhancing excipient, wherein:

the polypeptide conjugate comprises a polypeptide portion and one clearance-reducing moiety (CRM) conjugated to a lysine (K) residue on the polypeptide portion, wherein the polypeptide portion comprises the amino acid sequence of SEQ ID NO: 52, 55, 56, 60, 61, or 62:

wherein the CRM has the structure of below formula:

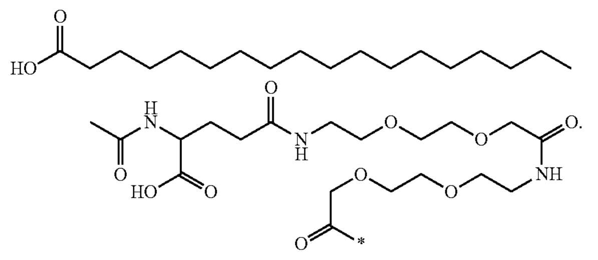

wherein "*" represents the point of attachment to a reactive group of the lysine residue on the polypeptide portion:

wherein the absorption enhancing excipient comprises sodium N-(8-(2-hydroxybenzoyl) amino) caprylic acid (SNAC); and wherein the pharmaceutical composition is a unit dosage form comprising approximately 0.5-50 mg of the polypeptide conjugate, approximately 50-300 mg of SNAC, and approximately 1-10 mg magnesium stearate.

2. The pharmaceutical composition of claim 1, wherein the unit dosage form comprises:

a) approximately 0.5-10 mg of the polypeptide conjugate, approximately 50-300 mg of SNAC, and approximately 1-10 mg magnesium stearate;

b) approximately 10-20 mg of the polypeptide conjugate, approximately 100-300 mg of SNAC, and approximately 1-10 mg magnesium stearate; or c) approximately 20-50 mg of the polypeptide conjugate, approximately 200-300 mg of SNAC, and approximately 1-10 mg magnesium stearate.

3. The pharmaceutical composition of claim 1, wherein the polypeptide conjugate comprises SEQ ID NO: 52 or 60 and has one of the structures shown below:

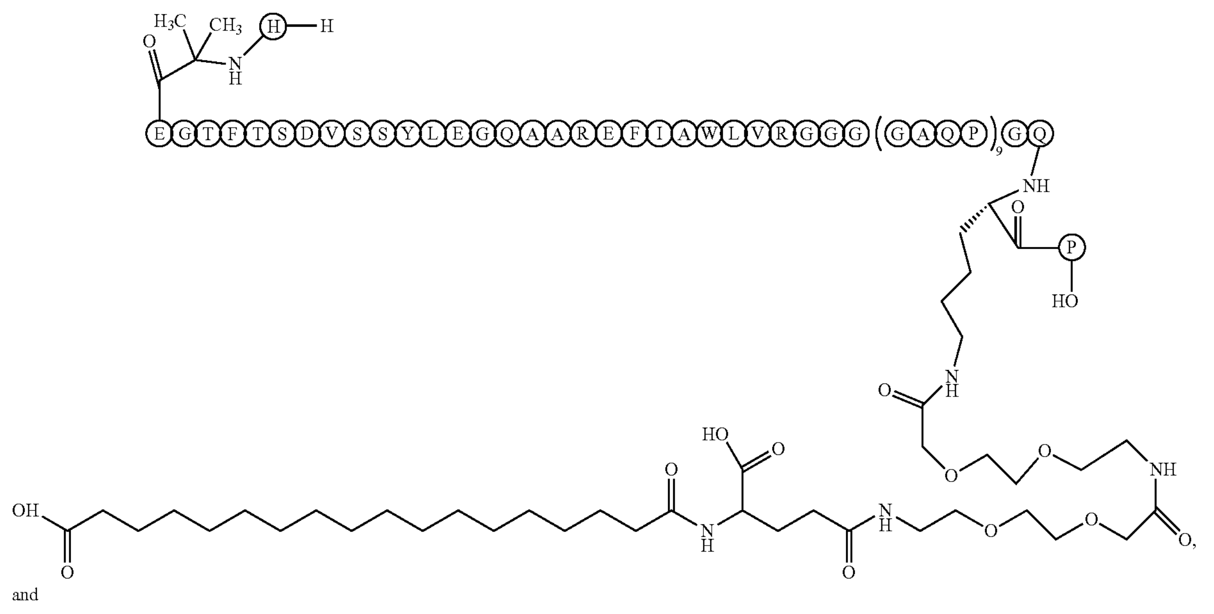

and

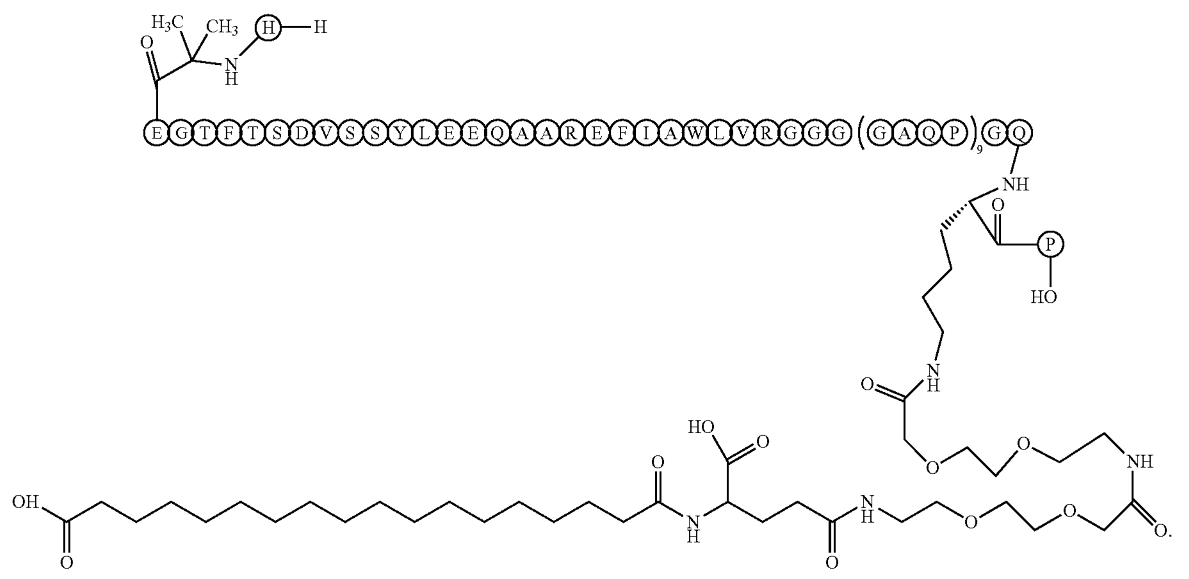

4. A pharmaceutical composition comprising a polypeptide conjugate and an absorption enhancing excipient, wherein:

the polypeptide conjugate comprises a polypeptide portion and two clearance-reducing moieties (CRM) conjugated to lysine (K) residues on the polypeptide portion, wherein the polypeptide portion comprises the amino acid sequence of SEQ ID NO: 51, 53, 54, 57, 58, 59, 85, or 86;

wherein the CRM has the structure of below formula:

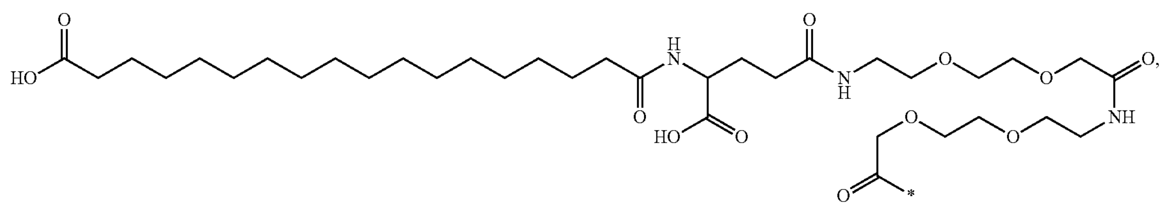 [SMILES: *C(=O)COCCOCCNC(=O)COCCOCCNC(=O)CCC(NC(=O)CCCCCCCCCCCCCCCCC(=O)O)C(=O)O]

wherein "*" represents the point of attachment to a reactive group of the lysine residue on the polypeptide portion:

wherein the absorption enhancing excipient comprises SNAC; and wherein the pharmaceutical composition is a unit dosage form comprising approximately 10-100 mg of the polypeptide conjugate, approximately 100-500 mg of SNAC, and approximately 1-20 mg magnesium stearate.

5. The pharmaceutical composition of claim 4, wherein the unit dosage form comprises:

a) approximately 10-20 mg of the polypeptide conjugate, approximately 100-300 mg of SNAC, and approximately 1-20 mg magnesium stearate;

b) approximately 20-40 mg of the polypeptide conjugate, approximately 200-300 mg of SNAC, and approximately 1-20 mg magnesium stearate;

c) approximately 20-50 mg of the polypeptide conjugate, approximately 200-300 mg of SNAC, and approximately 1-20 mg magnesium stearate;

d) approximately 40-50 mg of the polypeptide conjugate, approximately 200-300 mg of SNAC, and approximately 1-20 mg magnesium stearate; or e) approximately 50-100 mg of the polypeptide conjugate, approximately 300-500 mg of SNAC, and approximately 1-20 mg magnesium stearate.

6. The pharmaceutical composition of claim 4, wherein the polypeptide conjugate comprises SEQ ID NO: 57 and has the structure shown below:

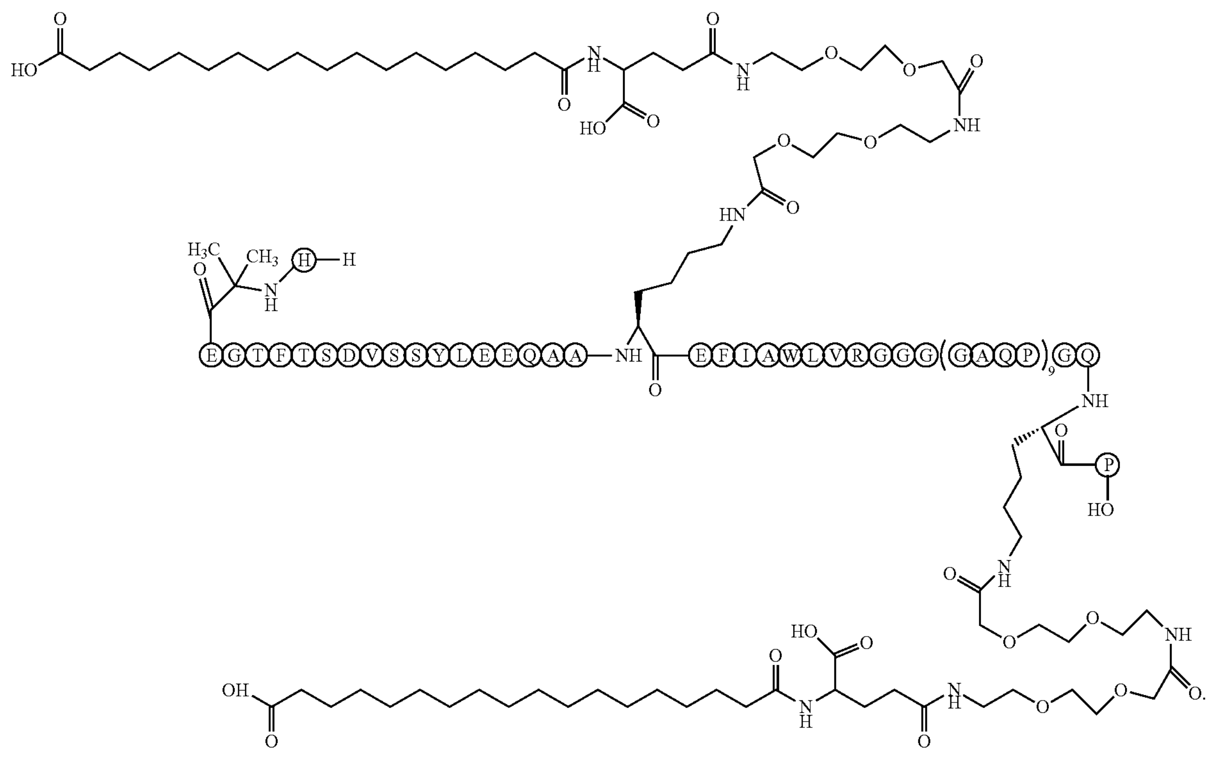

7. A method of treating a metabolic disorder in a subject in need thereof, wherein the method comprises administering to the subject the pharmaceutical composition of claim 1, and wherein the metabolic disorder is diabetes, obesity, overweight, non-alcoholic steatohepatitis (NASH), dyslipidemia, atherosclerosis, alcoholic steatohepatitis (ASH), diabetic nephropathy, gestational diabetes, metabolic syndrome, nonalcoholic fatty liver disease (NAFLD), end-stage liver disease, hepatic steatosis, liver cirrhosis, primary biliary cirrhosis (PBC), or Alzheimer's disease.

8. The method of claim 7, wherein the diabetes is one or more conditions selected from the group consisting of hyperglycemia, type 2 diabetes, impaired glucose tolerance, type 1 diabetes, non-insulin dependent diabetes, maturity onset diabetes of the young (MODY), gestational diabetes, and elevated level of hemoglobin A1C (HbA1c).

9. A method of managing body weight or reducing food intake or reducing body weight in a subject in need thereof, wherein the method comprises administering to the subject the pharmaceutical composition of claim 1.

* * * * *